United States Patent
Sharma

(10) Patent No.: US 10,576,278 B2
(45) Date of Patent: *Mar. 3, 2020

(54) SYSTEM AND METHOD FOR ELECTRICAL STIMULATION OF ANORECTAL STRUCTURES TO TREAT URINARY DYSFUNCTION

(71) Applicant: Virender K. Sharma, Paradise Valley, AZ (US)

(72) Inventor: Virender K. Sharma, Paradise Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/686,563

(22) Filed: Aug. 25, 2017

(65) Prior Publication Data

US 2018/0043157 A1 Feb. 15, 2018

Related U.S. Application Data

(63) Continuation-in-part of application No. 15/075,164, filed on Mar. 20, 2016, now Pat. No. 9,782,583,
(Continued)

(51) Int. Cl.
*A61N 1/36* (2006.01)
*A61N 1/372* (2006.01)
(Continued)

(52) U.S. Cl.
CPC ....... *A61N 1/36007* (2013.01); *A61N 1/0512* (2013.01); *A61N 1/0524* (2013.01);
(Continued)

(58) Field of Classification Search
CPC .................................................. A61N 1/36007
See application file for complete search history.

(56) References Cited

U.S. PATENT DOCUMENTS 3,628,538 A 12/1971 Vincent
3,866,613 A 2/1975 Kenny
(Continued)

FOREIGN PATENT DOCUMENTS

FR 2655548 6/1991
WO 2000019939 4/2000
(Continued)

OTHER PUBLICATIONS

Examination report for Chinese Patent Application No. 2013800205096, dated Nov. 4, 2016.
(Continued)

*Primary Examiner* — Joseph M Dietrich
(74) *Attorney, Agent, or Firm* — Novel IP

(57) ABSTRACT

A system and method for treating anorectal and/or genitourinary dysfunction includes implanting, in a minimally invasive manner, an electro-medical device for stimulation of two or more anatomical or histological structures of the anorectal region and/or genitourinary region. Electrodes operably connected to the device are positioned proximate the target anatomical or histological structures. The device provides either the same or different stimulation algorithms to each anatomical or histological structure, which may be the same or different. The varied stimulation parameters, such as pulse width, pulse amplitude, and pulse frequency, are defined such that after an application of the electrical pulses, an abdominal leak pressure, an abdominal leak volume, or a urine volume increases or a number of incontinent episodes or a mean incontinence volume per episode decreases relative to said parameters prior to the application of the electrical pulses.

18 Claims, 51 Drawing Sheets

Related U.S. Application Data which is a continuation-in-part of application No. 14/201,659, filed on Mar. 7, 2014, now Pat. No. 9,950,160, which is a continuation-in-part of application No. 13/400,868, filed on Feb. 21, 2012, now Pat. No. 8,706,234.

(60) Provisional application No. 62/379,612, filed on Aug. 25, 2016, provisional application No. 62/136,389, filed on Mar. 20, 2015.

(51) Int. Cl.
*A61N 1/05* (2006.01)
*A61N 1/375* (2006.01)

(52) U.S. Cl.
CPC ....... *A61N 1/3606* (2013.01); *A61N 1/36171* (2013.01); *A61N 1/36175* (2013.01); *A61N 1/37205* (2013.01); *A61N 1/37235* (2013.01); *A61N 1/3756* (2013.01)

(56) References Cited

U.S. PATENT DOCUMENTS

| | | | |
|---|---|---|---|
| 3,910,281 | A | 10/1975 | Kletschka |
| 3,938,502 | A | 2/1976 | Bom |
| 4,106,511 | A | 8/1978 | Erlandsson |
| 4,153,059 | A | 5/1979 | Fravel |
| 4,222,377 | A | 9/1980 | Burton |
| 4,406,288 | A | 9/1983 | Horwinski |
| 4,571,749 | A | 2/1986 | Fischell |
| 4,580,578 | A | 4/1986 | Barsom |
| 4,607,639 | A | 8/1986 | Tanagho |
| 4,731,083 | A | 3/1988 | Fischell |
| 4,739,764 | A | 4/1988 | Lue |
| 4,785,828 | A | 11/1988 | Maurer |
| 5,484,445 | A | 1/1996 | Knuth |
| 5,540,658 | A | 7/1996 | Evans |
| 5,562,717 | A | 10/1996 | Tippey |
| 5,702,428 | A | 12/1997 | Tippey |
| 5,861,014 | A | 1/1999 | Familoni |
| 5,927,282 | A | 7/1999 | Lenker |
| 5,954,714 | A | 9/1999 | Saadat |
| 5,984,854 | A | 11/1999 | Ishikawa |
| 6,002,964 | A | 12/1999 | Feler |
| 6,097,984 | A | 8/2000 | Douglas |
| 6,112,123 | A | 8/2000 | Kelleher |
| 6,131,575 | A | 10/2000 | Lenker |
| 6,135,945 | A | 10/2000 | Sultan |
| 6,238,389 | B1 | 5/2001 | Paddock |
| 6,240,315 | B1 | 5/2001 | Mo |
| 6,243,607 | B1 | 6/2001 | Mintchev |
| 6,428,467 | B1 | 8/2002 | Benderev |
| 6,449,511 | B1 | 9/2002 | Mintchev |
| 6,591,137 | B1 | 7/2003 | Fischell |
| 6,612,977 | B2 | 9/2003 | Staskin |
| 6,658,297 | B2 | 12/2003 | Loeb |
| 6,659,936 | B1 | 12/2003 | Furness |
| 6,735,474 | B1 | 5/2004 | Loeb |
| 6,749,607 | B2 | 6/2004 | Edwards |
| 6,826,428 | B1 | 11/2004 | Chen |
| 6,837,886 | B2 | 1/2005 | Collins |
| 6,845,776 | B2 | 1/2005 | Stack |
| 6,901,295 | B2 | 5/2005 | Sharma |
| 6,905,496 | B1 | 6/2005 | Ellman |
| 6,911,003 | B2 | 6/2005 | Anderson |
| 6,915,165 | B2 | 7/2005 | Forsell |
| 6,947,792 | B2 | 9/2005 | Ben-Haim |
| 6,960,203 | B2 | 11/2005 | Xiao |
| 7,025,762 | B2 | 4/2006 | Johnston |
| 7,054,689 | B1 | 5/2006 | Whitehurst |
| 7,087,053 | B2 | 8/2006 | Vanney |
| 7,120,498 | B2 | 10/2006 | Imran |
| 7,310,557 | B2 | 12/2007 | Maschino |
| 7,738,961 | B2 | 6/2010 | Sharma |
| 7,765,006 | B2 | 7/2010 | Martino |
| 7,765,007 | B2 | 7/2010 | Martino |
| 8,007,507 | B2 | 8/2011 | Waller |
| 8,160,709 | B2 | 4/2012 | Soffer |
| 8,447,403 | B2 | 5/2013 | Sharma |
| 8,447,404 | B2 | 5/2013 | Sharma |
| 8,538,534 | B2 | 9/2013 | Soffer |
| 8,543,210 | B2 | 9/2013 | Sharma |
| 8,594,811 | B2 | 11/2013 | Chen |
| 8,628,554 | B2 | 1/2014 | Sharma |
| 8,706,234 | B2 | 4/2014 | Sharma |
| 8,712,529 | B2 | 4/2014 | Sharma |
| 8,712,530 | B2 | 4/2014 | Sharma |
| 8,761,903 | B2 | 6/2014 | Chen |
| 8,798,753 | B2 | 8/2014 | Sharma |
| 8,831,729 | B2 | 9/2014 | Policker |
| 8,868,190 | B2 | 10/2014 | Guez |
| 9,020,597 | B2 | 4/2015 | Sharma |
| 9,037,244 | B2 | 5/2015 | Sharma |
| 9,037,245 | B2 | 5/2015 | Sharma |
| 9,061,147 | B2 | 6/2015 | Sharma |
| 9,079,028 | B2 | 7/2015 | Sharma |
| 9,782,583 | B2 | 10/2017 | Sharma |
| 9,950,160 | B2 | 4/2018 | Sharma |
| 2001/0041831 | A1 | 11/2001 | Starkweather |
| 2002/0161382 | A1 | 10/2002 | Neisz |
| 2002/0165589 | A1 | 11/2002 | Imran |
| 2002/0177846 | A1 | 11/2002 | Mulier |
| 2003/0014086 | A1 | 1/2003 | Sharma |
| 2003/0028232 | A1 | 2/2003 | Camps |
| 2003/0040808 | A1 | 2/2003 | Stack |
| 2003/0088145 | A1 | 5/2003 | Scott |
| 2003/0109935 | A1 | 6/2003 | Geitz |
| 2003/0120321 | A1 | 6/2003 | Bumm |
| 2003/0195600 | A1 | 10/2003 | Tronnes |
| 2003/0216729 | A1 | 11/2003 | Marchitto |
| 2004/0037986 | A1 | 2/2004 | Houston |
| 2004/0039453 | A1 | 2/2004 | Anderson |
| 2004/0044376 | A1 | 3/2004 | Flesler |
| 2004/0059393 | A1 | 3/2004 | Policker |
| 2004/0073453 | A1 | 4/2004 | Nenov |
| 2004/0167583 | A1 | 8/2004 | Knudson |
| 2004/0186544 | A1 | 9/2004 | King |
| 2004/0193229 | A1 | 9/2004 | Starkebaum |
| 2004/0220682 | A1 | 11/2004 | Levine |
| 2004/0230188 | A1 | 11/2004 | Cioanta |
| 2004/0236382 | A1 | 11/2004 | Dinsmoor |
| 2004/0236385 | A1 | 11/2004 | Rowe |
| 2004/0243152 | A1 | 12/2004 | Taylor |
| 2005/0095168 | A1 | 5/2005 | Centanni |
| 2005/0192642 | A1 | 9/2005 | Forsell |
| 2005/0216069 | A1 | 9/2005 | Cohen |
| 2005/0251219 | A1 | 11/2005 | Evans |
| 2005/0256587 | A1 | 11/2005 | Egan |
| 2006/0036237 | A1 | 2/2006 | Davison |
| 2006/0036293 | A1 | 2/2006 | Whitehurst |
| 2006/0064037 | A1 | 3/2006 | Shalon |
| 2006/0106442 | A1 | 5/2006 | Richardson |
| 2006/0116736 | A1 | 6/2006 | DiLorenzo |
| 2006/0161217 | A1 | 7/2006 | Jaax |
| 2006/0167498 | A1 | 7/2006 | DiLorenzo |
| 2006/0200217 | A1 | 9/2006 | Wessman |
| 2006/0206160 | A1 | 9/2006 | Cigaina |
| 2006/0218011 | A1 | 9/2006 | Walker |
| 2007/0016274 | A1 | 1/2007 | Boveja |
| 2007/0021650 | A1 | 1/2007 | Rocheleau |
| 2007/0100367 | A1 | 5/2007 | Quijano |
| 2007/0106337 | A1 | 5/2007 | Errico |
| 2007/0162085 | A1 | 7/2007 | DiLorenzo |
| 2007/0238942 | A1 | 10/2007 | Baylor |
| 2007/0282410 | A1 | 12/2007 | Cross |
| 2008/0021512 | A1 | 1/2008 | Knudson |
| 2008/0058887 | A1 | 3/2008 | Griffin |
| 2008/0058891 | A1 | 3/2008 | Ben-Haim |
| 2008/0065136 | A1 | 3/2008 | Young |
| 2008/0097466 | A1 | 4/2008 | Levine |
| 2008/0154191 | A1 | 6/2008 | Gobel |
| 2008/0195171 | A1 | 8/2008 | Sharma |
| 2008/0208355 | A1 | 8/2008 | Stack |

(56) References Cited

U.S. PATENT DOCUMENTS

| | | |
|---|---|---|
| 2008/0255678 A1 | 10/2008 | Cully |
| 2008/0281267 A1 | 11/2008 | Mehier |
| 2008/0300449 A1 | 12/2008 | Gerber |
| 2009/0005867 A1 | 1/2009 | Lefranc |
| 2009/0030475 A1 | 1/2009 | Brynelsen |
| 2009/0036945 A1 | 2/2009 | Chancellor |
| 2009/0054950 A1 | 2/2009 | Stephens |
| 2009/0069803 A1 | 3/2009 | Starkebaum |
| 2009/0131993 A1 | 5/2009 | Rousso |
| 2009/0132001 A1 | 5/2009 | Soffer |
| 2009/0204063 A1 | 8/2009 | Policker |
| 2009/0222058 A1 | 9/2009 | Craggs |
| 2009/0222060 A1 | 9/2009 | Boyd |
| 2009/0264951 A1 | 10/2009 | Sharma |
| 2009/0281553 A1 | 11/2009 | Kalloo |
| 2010/0076254 A1* | 3/2010 | Jimenez .......... A61F 2/0045 600/30 |
| 2010/0094270 A1 | 4/2010 | Sharma |
| 2010/0114082 A1 | 5/2010 | Sharma |
| 2010/0114083 A1 | 5/2010 | Sharma |
| 2010/0256775 A1 | 10/2010 | Belhe |
| 2010/0324432 A1 | 12/2010 | Bjorling |
| 2011/0004266 A1 | 1/2011 | Sharma |
| 2011/0071589 A1 | 3/2011 | Starkebaum |
| 2011/0213437 A9 | 9/2011 | Armstrong |
| 2011/0307075 A1 | 12/2011 | Sharma |
| 2012/0232610 A1 | 9/2012 | Soffer |
| 2012/0265103 A1 | 10/2012 | Policker |
| 2013/0006231 A1 | 1/2013 | Sharma |
| 2013/0013084 A1 | 1/2013 | Birk |
| 2013/0030503 A1 | 1/2013 | Yaniv |
| 2013/0178912 A1 | 7/2013 | Sharma |
| 2013/0218229 A1 | 8/2013 | Sharma |
| 2013/0231660 A1 | 9/2013 | Edwards |
| 2013/0289446 A1 | 10/2013 | Stone |
| 2014/0088664 A1 | 3/2014 | Sharma |
| 2014/0194917 A1 | 7/2014 | Sharma |
| 2014/0200568 A1 | 7/2014 | Sharma |
| 2014/0222106 A1 | 8/2014 | Sharma |
| 2014/0228911 A1 | 8/2014 | Sharma |
| 2014/0243593 A1 | 8/2014 | Goode |
| 2014/0276336 A1 | 9/2014 | Sharma |
| 2014/0309708 A1 | 10/2014 | Sharma |
| 2015/0018924 A1 | 1/2015 | Sharma |
| 2015/0057718 A1 | 2/2015 | Sharma |
| 2015/0066109 A1 | 3/2015 | Glasberg |
| 2015/0119646 A1 | 4/2015 | Sharma |
| 2015/0119869 A1 | 4/2015 | Sharma |
| 2015/0119952 A1 | 4/2015 | Sharma |
| 2015/0126990 A1 | 5/2015 | Sharma |
| 2015/0224310 A1 | 8/2015 | Sharma |
| 2015/0297885 A1 | 10/2015 | Goode |
| 2016/0303370 A1 | 10/2016 | Sharma |

FOREIGN PATENT DOCUMENTS

| | | |
|---|---|---|
| WO | 2000019940 | 4/2000 |
| WO | 2006092007 | 9/2006 |
| WO | 2008100974 A2 | 8/2008 |
| WO | 2009094609 | 7/2009 |
| WO | 2009114008 | 9/2009 |
| WO | 2010042461 | 4/2010 |
| WO | 2010042686 | 4/2010 |
| WO | 2011109739 | 9/2011 |
| WO | 2011159271 | 12/2011 |
| WO | 2012142539 | 10/2012 |
| WO | 2012151449 | 11/2012 |
| WO | 2012167213 | 12/2012 |
| WO | 2013033673 | 3/2013 |
| WO | 2013126930 | 8/2013 |
| WO | 2014032030 | 2/2014 |
| WO | 2014113724 | 7/2014 |
| WO | 2014153267 | 9/2014 |
| WO | 2015034867 | 3/2015 |
| WO | 2015077425 | 5/2015 |
| WO | 2015077435 | 5/2015 |
| WO | 2016154076 | 9/2016 |
| WO | 2016154076 A2 | 9/2016 |
| WO | 2018039552 A1 | 3/2018 |

OTHER PUBLICATIONS

Non-Final Rejection for U.S. Appl. No. 14/201,659, dated Oct. 10, 2014.
Non-Final Rejection for U.S. Appl. No. 13/400,868, dated Jan. 3, 2013.
Office Action dated May 15, 2015 for U.S. Appl. No. 14/201,659.
International Search Report for PCT/US2009/059609, dated Mar. 5, 2010.
International Search Report for PCT/US2012/040639, dated Dec. 18, 2012.
International Search Report for PCT/US2010/038444, dated Sep. 16, 2010.
International Search Report for PCT/US2009/59947, dated Feb. 12, 2010.
International Search Report for PCT/US2013/035031, dated Jun. 24, 2015.
International Search Report for PCT/US2014/012131, dated Jul. 30, 2014.
International Search Report for PCT/US2014/029846, dated Apr. 2, 2015.
International Search Report for PCT/US2009/031935, dated Jun. 15, 2009.
International Search Report for PCT/US2008/053780, dated Jun. 8, 2009.
International Search Report for PCT/US2008/056479, dated Aug. 20, 2008.
International Search Report for PCT/2011/027243, dated Jul. 8, 2011.
International Search Report for PCT/US2012/033695, dated Aug. 7, 2012.
International Search Report for PCT/US2012/053576, dated Dec. 24, 2012.
International Search Report for PCT/US2013/056520, dated Apr. 4, 2014.
International Search Report for PCT/US2012/036408, dated Aug. 17, 2012.
International Search Report for PCT/US2014/066565, dated Mar. 12, 2015.
International Search Report for PCT/US2014/053793, dated Mar. 27, 2015.
International Search Report for PCT/US2014/066578, dated Mar. 19, 2015.
Jameison, GG et al. "Laparoscopic Nissen Fundoplication". Annals of Surgery, vol. 220. No. 2, p. 139 (1994).
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Office Action dated Feb. 25, 2016 for U.S. Appl. No. 14/201,659.
Extended European Search Report for EP13752300.7, dated May 25, 2016.
Office Action dated Aug. 24, 2016 for U.S. Appl. No. 14/201,659.
Office Action dated Apr. 19, 2017 for U.S. Appl. No. 14/201,659.
Notice of Allowance dated Dec. 15, 2017 for U.S. Appl. No. 14/201,659.
Office Action dated Jan. 27, 2017 for U.S. Appl. No. 15/075,164.
International Search Report for PCT/US2016/023327, dated Jan. 12, 2017.
Noelting et al. "Normal Values for High-Resolution Anorectal Manometry in Healthy Women: Effects of Age and Significance of Rectoanal Gradient". Am J Gastroenterol. Oct. 2012; 107(10): 1530-1536.
Seong et al. "Comparative analysis of summary scoring systems in measuring fecal incontinence". J Korean Surg Soc. 2011; 81:326-331.

(56) References Cited

OTHER PUBLICATIONS

Rust et al. "The GRISS: A Psychometric Instrument for the Assessment of Sexual Dysfunction". Articles of Sexual Behavior, vol. 15, No. 2, 1986, 157-165.
Infrasca, R. "Sexual Dysfunction Questionnaire: scale development and psychometric validation". Giorn Ital Psicopat 2011; 17:253-260.
Althof et al. "Outcome Measurement in Female Sexual Dysfunction Clinical Trials: Review and Recommendations". Journal of Sex & Marital Therapy, 31: 153-166, 2005.
Janssen et al. "Promis Sexual Function and Satisfaction Measures User Manual". nihpromis.org; Jul. 8, 2015, 1-15.
Rosen et al. "The International Index of Erectile Function (IIEF)". Sample; 1997. 1-5.
Ghoniem et al. "Evaluation and outcome measures in the treatment of female urinary stress incontinence: International Urogynecological Association (IUGA) guidelines for research and clinical practice". Int Urogynecol J (2008) 19:5-33.
Gill et al. "Urodynamic Studies for Urinary Incontinence". http://emedicine.medscape.com/article/1988665overview#a4; Mar. 17, 2016, 1-14.
Notice of Allowanace dated May 31, 2017 for U.S. Appl. No. 15/075,164.
International Search Report for PCT/US2017/048594, dated Dec. 26, 2017.

* cited by examiner

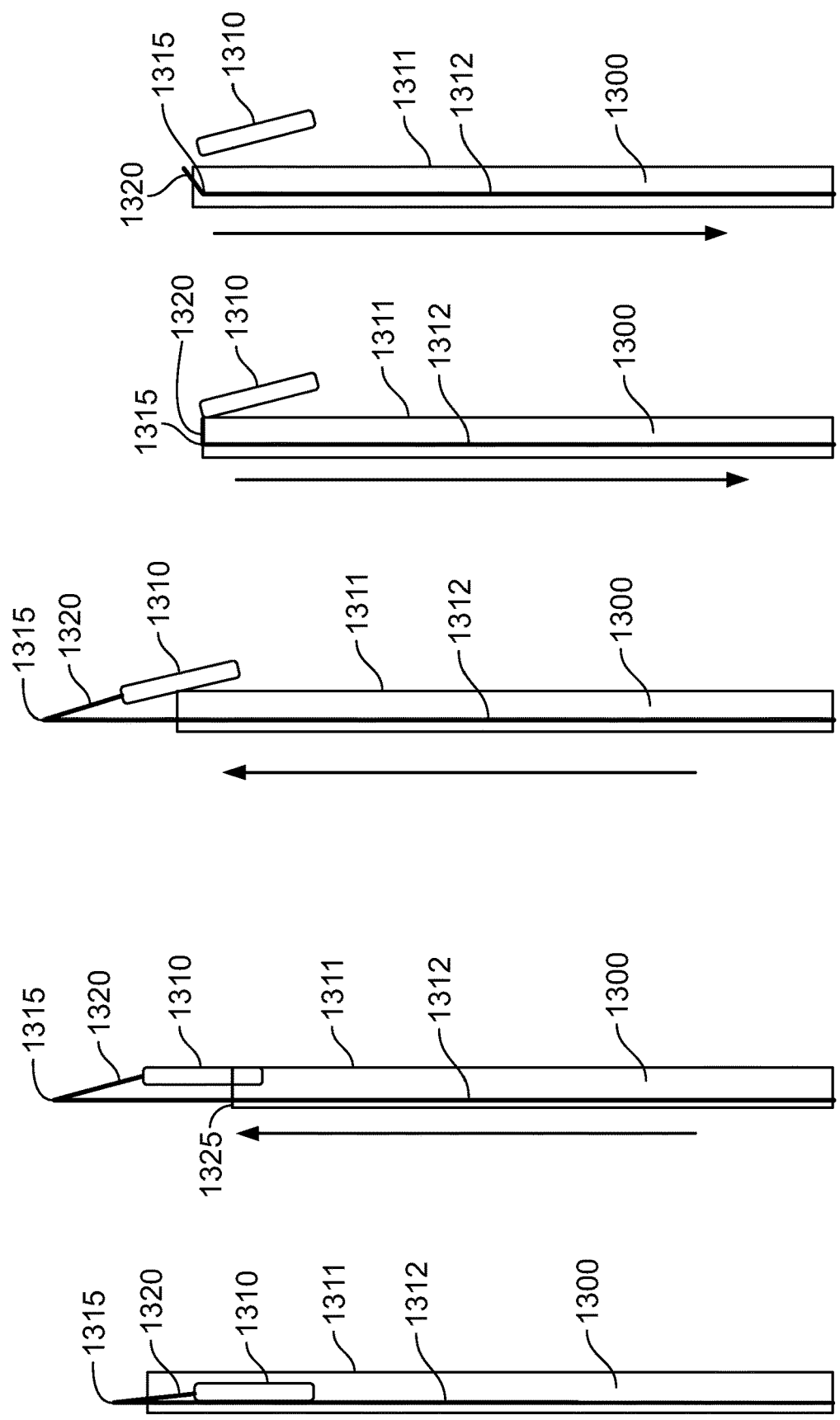

APPENDIX 1
Sexual Dysfunction Questionnaire (SDQ). Questionario sulle Disfunzioni Sessuali (QDS)

Gender  M  F    Age ___    Education ___    Date _/_/_

| | Always | Often | Sometimes | Rarely | Never |
|---|---|---|---|---|---|
| 1) I am satisfied with my sex life | 1 | 2 | 3 | 4 | 5 |
| 2) I have sexual fantasies | 1 | 2 | 3 | 4 | 5 |
| 3) I have sexual dreams | 1 | 2 | 3 | 4 | 5 |
| 4) I like to talk about things that concern sexuality | 1 | 2 | 3 | 4 | 5 |
| 5) I like to tell jokes involving sex | 1 | 2 | 3 | 4 | 5 |
| 6) I feel uninhibited towards sexuality | 1 | 2 | 3 | 4 | 5 |
| 7) I like to keep sexuality hidden | 5 | 4 | 3 | 2 | 1 |
| 8) I speak about sexuality with my partner | 1 | 2 | 3 | 4 | 5 |
| 9) I live sexuality in rigid manner | 5 | 4 | 3 | 2 | 1 |
| 10) I would live better without sexuality | 5 | 4 | 3 | 2 | 1 |
| 11) My sex life is planned | 5 | 4 | 3 | 2 | 1 |
| 12) I avoid situations that arouse my sexuality | 5 | 4 | 3 | 2 | 1 |
| 13) Sexuality creates worry for me | 1 | 2 | 3 | 4 | 5 |
| 14) I like watching movies or scenes involving sex | 1 | 2 | 3 | 4 | 5 |
| 15) I like to talk during sex | 1 | 2 | 3 | 4 | 5 |
| 16) I reach orgasm during sex | 1 | 2 | 3 | 4 | 5 |
| 17) During sex I "let go" | 5 | 4 | 3 | 2 | 1 |
| 18) Sexuality scares me | 1 | 2 | 3 | 4 | 5 |
| 19) I like to have an active role in my sexuality | 5 | 2 | 3 | 4 | 5 |

FIG. 21

| Fecal Incontinence | Improvement* |
|---|---|
| 2201 Patient Perception Score (Visual Analog Score 1-100) | ≥ 5% |
| 2202 Rothenberg | > 5% |
| 2203 Wexner | > 5% |
| 2204 Vaizey | > 5% |
| 2205 Fecal Incontinence Severity Index (FISI) | > 5% |
| 2206 Internal Anal Sphincter Resting Pressure | ≥ 5% or >33 mm Hg |
| 2207 External Anal Sphincter Resting Pressure | ≥ 5% |
| 2208 Anal Sphincter Squeeze Pressure | ≥ 5% or > 99 mm Hg |
| 2209 Stress Testing (Abdominal Leak-point Pressure) | ≥ 5% or > 60 cm H2O |
| 2210 Stress Testing (Abdominal Leak-point Volume) | ≥ 5% or > 50 cc |
| 2211 Anal High Pressure Zone | ≥ 5% or > 2.4 cm |
| 2212 Anal Squeeze Duration | ≥ 5% or > 3 sec |
| 2213 First Sensation Volume | ≥ 5% or > 20 ml |
| 2214 Desire to Defecate Volume | ≥ 5% or > 40 ml |
| 2215 Urgency Volume | ≥ 5% or > 60 ml |
| 2216 Balloon Expulsion Time | ≥ 5% or < 3 min |
| 2217 Rectal Pressure During Evacuation | ≥ 5% or > 5mm Hg |
| 2218 Anal Pressure During Evacuation | ≥ 5% or < 5mm Hg |
| 2219 Quality of Life (SF6, SF12) | ≥ 5% |

FIG. 22

Table 1. Summary of summary scoring systems in measuring fecal incontinence: frequency, type, and impact components

| Variable | Category number | Frequency — 2301 | | Type — 2302 | | | | 2303 — Impact components | |
|---|---|---|---|---|---|---|---|---|---|
| | | Lowest[a] | Highest | Gas | Liquid | Solid | Others | Pad usage | Lifestyle alteration |
| Rothenberger 2300 | 4 | Less than 1/mo | More than 1/wk | + | + | + | - | - | + |
| Wexner 2300 | 5 | Less than 1/mo | More than 1/day | + | + | + | - | + | + |
| Vaizey 2300 | 5 | 1/mo | Every day | + | + | + | + Urgency | + | + |
| FISI | 6 | 1-3/mo | More than 2/day | + | + | + | + Mucus | - | - |

FISI, Fecal Incontinence Severity Index.
a) Other than "never".

FIG. 23A

Table 2. Summary of summary scoring systems in measuring fecal incontinence; score

| Variable | 2310 — Range | Score 2312 — Weight |
|---|---|---|
| Rothenberger | 0-30 | Scores for gas incontinence are 1-3; liquid incontinence 4-6; solid incontinence 7-9; lifestyle alteration 10-12. |
| Wexner | 0-20 | All Categories are given equal weights. |
| Vaizey | 0-24 | Gas, liquid, solid incontinence and lifestyle alteration are given equal weights. Others are scored variably. |
| FISI | 0-61 | Weights were already determined by patients. |

FISI, Fecal Incontinence Severity Index.

FIG. 23B

3201 — Provide a device comprising at least a first electrode and a second electrode operably connected to a stimulus generator configured to receive at least one stimulation signal from a controller

3202 — Implant the device in an anorectal and a genitourinary region of the patient

3203 — Position the first electrode in electrical communication with a first target tissue within the anorectal region of the patient

3204 — Position the second electrode in electrical communication with a second target tissue within the genitourinary region of the patient, wherein the second target tissue is distinct and different from the first target tissue

3205 — Cause said controller to generate a first stimulation signal based on a first programmed algorithm and a second stimulation signal based on a second algorithm, that are transmitted to the stimulus generator

3206 — Stimulus generator in response to the first stimulation signal, generates a first stimulation pulse that is transmitted to the first target tissue via the first electrode and in response to the second stimulation signal, generates a second stimulation pulse that is transmitted to the second target tissue via the second electrode, wherein the first electrical stimulation pulse is optimized to stimulate an anorectal tissue of said patient and the second electrical stimulation pulse is optimized to stimulate a genitourinary tissue of said patient

FIG. 32

SYSTEM AND METHOD FOR ELECTRICAL STIMULATION OF ANORECTAL STRUCTURES TO TREAT URINARY DYSFUNCTION

CROSS-REFERENCE

The present application is a continuation-in-part application of U.S. patent application Ser. No. 15/075,164, entitled "System and Method For Electrical Stimulation of Anorectal Structures To Treat Urinary Dysfunction" and filed on Mar. 20, 2016, which relies on U.S. Patent Provisional Application No. 62/136,389, entitled "System and Method For Electrical Stimulation of Anorectal Structures To Treat Anal and Urinary Dysfunction" and filed on Mar. 20, 2015, for priority. U.S. patent application Ser. No. 15/075,164 is also a continuation-in-part application of U.S. patent application Ser. No. 14/201,659, entitled "System and Method for Electrical Stimulation of Anorectal Structures to Treat Anal Dysfunction" and filed on Mar. 7, 2014, which is a continuation application of U.S. patent application Ser. No. 13/400,868, of the same title, filed on Feb. 21, 2012, and issued as U.S. Pat. No. 8,706,234 on Apr. 22, 2014.

The present application further relies on U.S. Patent Provisional Application No. 62/379,612, entitled "System and Method For Electrical Stimulation of Anorectal Structures To Treat Urinary Dysfunction" and filed on Aug. 25, 2016, for priority.

All of the aforementioned patent applications are incorporated herein by reference in their entirety.

FIELD

The present specification relates generally to a method and apparatus for electrical stimulation of the gastrointestinal tract. More particularly, the present specification relates to a method and apparatus for treating anal dysfunction by electrically stimulating the submucosa or muscularis mucosa or the muscularis propria of the rectum or anal sphincter. The present specification also relates to a method and apparatus for treating a urinary dysfunction by electrically stimulating the submucosa or muscularis mucosa or the muscularis propria of the rectum, anal sphincter or other ano-rectal structure.

BACKGROUND

Fecal incontinence refers to the involuntary loss of gas or liquid stool (minor incontinence) or the involuntary loss of solid stool (major incontinence). Surveys indicate that fecal incontinence affects between 2 and 7 percent of the general population, although the true incidence may be much higher since many people are hesitant to discuss the problem with a healthcare provider.

Minor fecal incontinence affects men and women equally, but women are almost twice as likely as men to report major incontinence. Fecal incontinence is also more common in older adults. It is particularly common in nursing home residents, with studies suggesting that almost half of all residents are incontinent. Fecal incontinence can undermine self-confidence, create anxiety, and lead to social isolation; however, fecal incontinence is a treatable condition. Treatment can lessen symptoms in most cases and can often completely cure incontinence.

Continence requires the normal function of both the lower digestive tract and the nervous system. The anal sphincters, along with the pelvic muscles that surround the end of the digestive tract, ensure controlled movement of digestive tract contents. There are many possible causes of fecal incontinence. In most cases, incontinence results from some combination of these causes. Three types of treatment are commonly used for fecal incontinence: medical therapy, biofeedback, and surgery. Medical therapy includes medication and certain measures that can reduce the frequency of incontinence and firm up the stools, which can reduce or eliminate episodes of fecal leakage. Often, basic measures will improve minor incontinence, but more aggressive measures may be needed to control frequent or severe episodes of leakage. Bulking substances that promote bulkier stools may help control diarrhea by thickening the stools. Methylcellulose (a form of fiber) is one type of bulking substance that is commonly used. Increasing dietary fiber may also help to bulk stools. Anti-diarrheal medications such as loperamide and diphenoxylate reduce the frequency of stools and are helpful in treating fecal incontinence. Loperamide can also increase the tone (tightness) of the anal sphincter muscle. When taken before meals, anticholinergic medications (such as the prescription drug hyoscyamine), by reducing contractions in the colon, can decrease the incontinence that occurs after meals in some people.

Biofeedback is a safe and noninvasive way of retraining muscles. During biofeedback training, sensors are used to help the patient identify and contract the anal sphincter muscles which help maintain continence. This is usually done in a healthcare provider or physical therapist's office. Biofeedback can be successful, although results can be variable. The people most likely to benefit from this type of therapy are those who can contract the anal sphincter muscle and have some sensation when they need to have a bowel movement. The effects of biofeedback may begin to decline six months after the initial training and retraining may be helpful.

Sacral nerve electrical stimulation can eliminate leakage in 40 to 75 percent of people whose anal sphincter muscles are intact. An electrode is surgically inserted near a nerve in the sacrum (low back). It is not entirely clear how sacral nerve stimulation works. The treatment is invasive, requiring surgical implantation. Some patients develop complications from the surgery, including pain, device malfunction, or infection, which may require that the device be removed or replaced. At present, this treatment is generally reserved for people with an intact or repaired anal sphincter who have not shown improvement with other treatments.

Electrical stimulation of the anal sphincter involves using a mild electrical current to stimulate the anal sphincter muscles to contract, which can strengthen the muscles over time. The electrical current is applied using a small probe, which the patient inserts inside the rectum for a few minutes every day for 8 to 12 weeks. A controlled trial suggested that electrical stimulation is only a modest benefit, possibly from increasing sensation in the anal area; this treatment, however, is inexpensive, non-invasive, and has few to no side effects. It may, however, be uncomfortable for patients who understandably may not like frequently inserting the stimulator device.

Several different surgical procedures can help alleviate fecal incontinence. Surgical repair can reduce or resolve incontinence, particularly for women who develop a tear in the external anal sphincter during childbirth and in people with injury of the sphincter due to surgery or other causes. Surgery cures fecal incontinence in 80 percent of women with childbirth-related sphincter tears.

In people who have irreparable damage of the sphincters, muscles can be transferred from other areas of the body, usually the leg or buttock, and surgically placed around the anal canal. These muscles mimic the action of the damaged sphincters. Muscle transfer surgery can restore continence in up to 73 percent of people with otherwise irreparable damage. An alternative to a transferred muscle is a synthetic anal cuff that can be inflated to hold back feces and deflated to allow bowel movements. However, this type of procedure is only performed in specialized centers. Complications can occur even when these surgeries are performed by experts.

Colostomy is a surgical procedure in which the colon is surgically attached to the abdominal wall. Stool is collected in a bag that fits snugly against the skin. This eliminates leakage of stool from the rectum. Variations on the procedure may allow the person to control bowel emptying. Colostomy is usually a last resort, after other treatments have failed. It may also be considered for people with intolerable symptoms who are not candidates for any other therapy.

Onuf's nucleus is a distinct group of neurons located in the ventral portion of the anterior horn of the sacral region of the human spinal cord. Onuf's nucleus is involved in the maintenance of micturition and defecatory continence, as well as muscular contraction during orgasm. The nucleus contains motor neurons and is the origin of the pudendal nerve. The sacral region of the spinal cord comprises the fourth segment of vertebrae in the spinal cord. This small group of neural cells is located between S1 and S2 or S2 and S3 and can extend to the caudal end of the first sacral segment or to the middle part of the third sacral segment. Onuf's nucleus is found almost symmetrically on both sides of the ventral horn. The nucleus is arranged in a neuropil and averages approximately 300-500 neurons in both the left and right ventral horns in animals. Humans average 625 neurons total across both sides of the spine which measures about 4-6 mm on each side. Onuf's nucleus is comprised of motoneurons which are characterized by their multipolarity and large Nissl bodies. Onuf's nucleus is the origin of innervation for the striated muscles of the rectum and urethral sphincter. The neurons of Onuf's nucleus are responsible for controlling external sphincter muscles of the anus and urethra in humans. Onuf s nucleus may also control the ischiocavernosus and bulbocavernosus muscles which function in penile erection and ejaculation in males. The dorsomedial subnucleus innervates the rectal striated sphincter and the ventrolateral subgroup connects to the urethral striated sphincter. The motor neurons of Onuf s nucleus innervate striated musculature (rhabdosphincter muscle) which is controlled voluntarily. Neurons in Onuf s nucleus lack autonomic dense core vesicles even though they receive the same synaptic endings as alpha-motor neurons. Onuf s nucleus cells have the same cytoskeletal abnormalities as alpha-motor neurons in motor neuron disease/amyotrophic lateral sclerosis. Diseases characterized by disturbances in urination and defecation affect autonomic and Onuf s nucleus cells similarly. Both cell types are spared by amyotrophic lateral sclerosis. Onuf s nucleus cells are anatomically linked with the sacral parasympathetic motor neurons and have many peptidergic nerve terminals. Cells in Onuf s nucleus resemble autonomic neurons and do not receive afferents from adjacent neurons.

The motoneurons in Onuf s nucleus contain a dense array of serotonin (5-HT) and norepinephrine (NE) receptors and transmitters and are activated by glutamate. When the 5-HT and NE receptors are stimulated, the guarding reflex occurs to prevent voiding of the bladder caused by unexpected abdominal pressure.

There are three layers of muscle that are known to control urine flow through the urethra: an inner band of longitudinal smooth muscle; a middle band of circular smooth muscle; and an external band of striated muscle called the rhabdosphincter. The urethra is controlled by the sympathetic, parasympathetic, and somatic divisions of the peripheral nervous system. The sympathetic innervation comes from the sympathetic preganglionic neurons located in the upper lumbar spinal cord along the hypogastric nerve and terminates in the longitudinal and circular smooth muscle layers in the urethra. The parasympathetic nerve supply comes from the parasympathetic preganglionic neurons in the sacral spinal cord and also terminates in the longitudinal and circular smooth muscle layers. Finally, the somatic nerve supply arises from the urethral sphincter motor neurons in Onuf s nucleus. The pudendal nerve that extends from Onuf s nucleus connects directly to the rhabdosphincter muscle to control micturition.

The sympathetic storage reflex or pelvic-to-hypo-gastric reflex is initiated when the bladder swells. Stretch receptors cause postganglionic neurons to release norepinephrine (NE). NE causes the bladder to relax and the urethra to contract, thus preventing urine loss. The somatic storage reflex or the pelvic-to-pudendal or guarding reflex is initiated when one laughs, sneezes, or coughs, which causes increased bladder pressure. Glutamate is the primary excitatory transmitter for the reflex. Glutamate activates N-methyl-D-aspartame (NMDA) and α-amino-3-hydroxy-5-methyl-4-isoxazolepropionic acid (AMPA) receptors which produce action potentials. These action potentials activate the release of acetylcholine causing the rhabdosphincter muscle fibers to contract. When the guarding reflex does not function normally, stress urinary incontinence occurs.

Parasympathetic and sympathetic nervous systems form a pelvic plexus at the lateral side of the rectum before reaching the bladder and sphincter. Sympathetic pathways originate from T11-L2 (sympathetic nucleus; intermediolateral column of gray matter), inhibiting the bladder body and exciting the bladder base and proximal urethral sphincter. Parasympathetic nerves emerge from S2-4 (parasympathetic nucleus; intermediolateral column of gray matter), exciting the bladder and relaxing the urethra. Sacral somatic pathways emerge from S2-4 (Onuf s nucleus; ventral horn) forming the pudendal nerve and providing innervation to the striated urethral sphincter. The pudendal nerve from S2-4 excites the distal striated urethral sphincter. Efferent action includes the parasympathetic postganglionic neurons located in the detrusor wall layer as well as in the pelvic plexus which release the excitatory transmitter acetylcholine. Activation of pelvic nerves induces contraction of the bladder body, which contributes to emptying of the bladder. Sympathetic input provides a noradrenergic excitatory and inhibitory input to the bladder and urethra. Activation of hypogastric nerves induces relaxation of the bladder body and contraction of the bladder outlet and urethra, which contribute to urine storage in the bladder. Activation of the pudendal nerve causes the contraction of the striated urethral sphincter. Afferent axons in the pelvic, hypogastric, and pudendal nerves also transmit sensory information from the lower urinary tract to the spinal cord. Pelvic nerve afferents consist of myelinated A-delta fibers mediating normal micturition sensitive to gradual distention of the urinary bladder and unmyelinated C-fibers that, under normal conditions, do not respond to bladder distention. In various pathological conditions, including spinal cord injury, chemoreceptors and mechanosensitive nociceptors from the bladder and urethra become hyperactive and can cause hyperreflexic bladder and urinary incontinence.

Efferent parasympathetic axons from preganglionic neurons in the sacral spinal cord traverse the pelvic nerve and make synapses in the pelvic plexus. Postganglionic neurons are primarily cholinergic but they may also contain purinergic, peptidergic and nitrergic neurons. Postganglionic neurons innervate the detrusor smooth muscle. Afferent sensory neurotransmitters from the detrusor smooth muscle include glutamate, neuropeptides and nitric oxide. The hypogastric nerve includes sympathetic postganglionic fibers which are primarily noradrenergic, but may also be purinergic and peptidergic, and innervates primarily longitudinal and circular smooth muscle layers in the bladder neck and proximal urethra with a minor component innervating the detrusor muscle. The pudendal nerve provides efferent innervation of the urethral rhabdosphincter as well as the external anal sphincter and some perineal muscles. The female levator ani muscle is not innervated by the pudendal nerve but rather by innervation that originates from the sacral nerve roots (S3-S5) and travels on the superior surface of the pelvic floor (levator ani nerve).

Urinary incontinence, defined commonly as the inability to control the passage of urine, is a relatively common disorder, particularly in females. For many, it is a distressing problem which may have a profound impact on quality of life. Urinary incontinence almost always results from an underlying treatable medical condition but is under-reported to medical practitioners. It is generally known that the prevalence of urinary incontinence in the United States ranges from 3% to 14% with estimates ranging up to 40% for the elderly.

Bladder control problems have been found to be associated with a higher incidence of many other health problems, such as obesity and diabetes. Difficulty with bladder control leads to higher rates of depression and limited activity levels. Incontinence is expensive both to individuals, in the form of bladder control products, and to the health care system and nursing home industry. Injury related to incontinence is a leading cause of admission to assisted living and nursing care facilities. More than 50% of nursing facility admissions are related to incontinence.

Men tend to experience urinary incontinence less often than women. While urinary incontinence affects older men more often than younger men, the onset of incontinence can happen at any age. During urination, muscles in the wall of the bladder contract, forcing urine out of the bladder and into the urethra. At the same time, sphincter muscles surrounding the urethra relax, allowing urine to pass from the bladder, through the urethra, and out of the body. Incontinence will occur if the bladder muscles suddenly contract or muscles surrounding the urethra suddenly relax.

Urinary incontinence is a complex disorder and is classified into many subtypes. These subtypes include stress incontinence, urge incontinence, functional incontinence, overflow incontinence, structural incontinence, mixed urinary incontinence, and transient incontinence.

Stress urinary incontinence (SUI), also known as effort incontinence, is due essentially to insufficient strength of the pelvic floor muscles. SUI involves the loss of small amounts of urine associated with coughing, laughing, sneezing, exercising or other movements that increase intra-abdominal pressure and thus increase pressure on the bladder. The urethra is supported by fascia of the pelvic floor. If this support is insufficient, the urethra can move downward at times of increased abdominal pressure, allowing urine to pass.

Stress incontinence is the most common form of incontinence in men and is often encountered following a prostatectomy. In women, physical changes resulting from pregnancy, childbirth, and menopause often contribute to stress incontinence. Stress incontinence can worsen during the week before the menstrual period. At that time, lowered estrogen levels may lead to lower muscular pressure around the urethra, increasing chances of leakage. The incidence of stress incontinence increases following menopause, similarly because of lowered estrogen levels. In female high-level athletes, effort incontinence occurs in all sports involving abrupt repeated increases in intra-abdominal pressure that may exceed perineal floor resistance. Most laboratory results, such as urine analysis, cystometry and post void residual volume, are normal.

Urge incontinence is defined as the involuntary passage of urine caused by abnormal bladder contractions with a concomitant sense of urgency. Studies suggest that urge incontinence may be caused by nerve damage or by psychosomatic factors that lead to involuntary bladder contractions. The most common cause of urge incontinence is involuntary and inappropriate detrusor muscle contractions. Detrusor hyperactivity is subdivided into Idiopathic Detrusor Overactivity (IDO), due to local or surrounding infection, inflammation or irritation of the bladder, and Neurogenic Detrusor Overactivity (NDO), due to defective central nervous system (CNS) inhibitory response. Medical professionals describe a bladder of a patient having urge incontinence as "unstable", "spastic", or "overactive". Urge incontinence may also be called "reflex incontinence" if it results from overactive nerves controlling the bladder.

Patients with urge incontinence can suffer incontinence during sleep, after drinking a small amount of water, or when they touch water or hear it running (as when washing dishes or hearing someone else taking a shower). Involuntary actions of bladder muscles can occur because of damage to the nerves of the bladder, to the nervous system (spinal cord and brain), or to the muscles themselves. Multiple sclerosis, Parkinson's disease, Alzheimer's disease, stroke, spina bifida and injury, including injury that occurs during surgery, can all harm bladder nerves or muscles.

Functional incontinence occurs when a person recognizes the need to urinate but cannot physically make it to the bathroom in time due to limited mobility. The urine loss may be large. Causes of functional incontinence include confusion, dementia, poor eyesight, poor mobility, poor dexterity, unwillingness to go to the toilet because of depression, anxiety or anger, drunkenness, or being in a situation in which it is impossible to reach a toilet.

Overflow incontinence is the patient's inability to stop their bladders from constantly dribbling or continuing to dribble for some time after they have passed urine. Overflow incontinence occurs when the patient's bladder is always full so that it frequently leaks urine. Weak bladder muscles, resulting in incomplete emptying of the bladder, or a blocked urethra can cause this type of incontinence. Autonomic neuropathy from diabetes or other diseases (e.g. multiple sclerosis) can decrease neural signals from the bladder (allowing for overfilling) and may also decrease the expulsion of urine by the detrusor muscle (allowing for urinary retention). Additionally, tumors and kidney stones can block the urethra. Spinal cord injuries or nervous system disorders are additional causes of overflow incontinence. In men, benign prostatic hyperplasia (BPH) may also restrict the flow of urine. Overflow incontinence is rare in women, although sometimes it is caused by fibroid or ovarian tumors. Also, overflow incontinence can result from increased outlet resistance due to advanced vaginal prolapse causing a "kink" in the urethra, or after an anti-incontinence procedure which has overcorrected the problem.

Structural incontinence can be caused by structural problems, usually diagnosed in childhood, which can include, for example, an ectopic ureter. Fistulas caused by obstetric and gynecologic trauma or injury can also lead to structural incontinence. Such types of fistulas include, most commonly, vesicovaginal fistulas, and, more rarely, ureterovaginal fistulas. These may be difficult to recognize but diagnosis can be achieved through the use of standard techniques along with a vaginogram or radiologically by viewing the vaginal vault with instillation of contrast media.

Mixed urinary incontinence disorder is not uncommon in the elderly female population and can sometimes be complicated by urinary retention, making the disorder a treatment challenge requiring staged multimodal treatment.

Transient incontinence is a temporary version of incontinence. It can be triggered by medications, urinary tract infections, mental impairment, restricted mobility, and stool impaction (severe constipation) which can push against the urinary tract and obstruct outflow.

Treatment options range from conservative treatment, including behavior management and medications, to surgery. Behavior techniques for incontinence include retraining the bladder to hold more urine. The goal is to lengthen the time between periods of urination. This includes relaxation techniques, learning how to cope with urges to urinate, fluid management, and avoidance of alcohol, caffeine or acidic foods. One of the most common treatment recommendations includes exercising the muscles of the pelvis. Kegel exercises to strengthen or retrain pelvic floor muscles and sphincter muscles can reduce stress leakage. Increasingly, there is evidence of the effectiveness of pelvic floor muscle exercise (PFME) to improve bladder control. Urinary incontinence following childbirth can be improved by performing PFME.

Biofeedback uses measuring devices to help the patient become aware of his or her body's functioning. By using electronic devices or diaries to track when the bladder and urethral muscles contract, the patient can gain control over these muscles. Biofeedback can be used with pelvic muscle exercises and electrical stimulation to relieve stress and urge incontinence. Timed voiding (urinating) and bladder training are techniques that use biofeedback. In timed voiding, the patient fills in a chart tracking times of voiding and leaking occurrences. From the patterns that appear in the chart, the patient can plan to empty his or her bladder before he or she would otherwise leak. Biofeedback and muscle conditioning, known as bladder training, can alter the bladder's schedule for storing and emptying urine. These techniques may be used for urge and overflow incontinence.

Increasing the bulk of the urethra, thereby increasing outlet resistance, may be used to treat certain forms of incontinence. This is most effective in patients with a relatively fixed urethra. A variety of materials have been historically used to add to the bulk, including blood and fat, with limited success. The most widely used substance, glutaraldehyde cross-linked collagen (GAX collagen), has proved to be of value in many patients. The main drawback with using GAX collagen to increase the bulk of the urethra is the need to repeat the procedure over time.

Medications can reduce many types of leakage. Some drugs inhibit contractions of an overactive bladder, others relax muscles, leading to more complete bladder emptying during urination, and yet others tighten muscles at the bladder neck and urethra, preventing leakage. Some hormones, such as estrogen, are believed to cause muscles involved in urination to function normally. Pharmacological treatments of urinary incontinence include: topical or vaginal estrogens, used in cases of vaginal atrophy; tolterodine (Detrol®); oxybutynin (Ditropan®, Oxytrol®); propantheline; darifenacin (Enablex®); solifenacin (VESIcare®); trospium chloride (Sanctura®), used in urge incontinence; imipramine (Tofranil®), used in mixed and stress urinary incontinence; pseudoephedrine; and duloxetine (Cymbalta®), used in stress urinary incontinence. Some of these medications can produce harmful side effects if used for long periods. In particular, estrogen therapy has been associated with an increased risk of cancers of the breast and endometrium (lining of the uterus).

Urge incontinence has historically been treated with a variety of behavioral treatments, medications, and surgery. Urinary urge incontinence (UUI) is frequently caused by an overactive bladder (OAB) and the most effective pharmacological treatment currently for OAB includes anticholinergic medications. However, many patients do not respond to these medications or have significant side effects causing discontinuation such that these patients experience persistent symptomatic UUI. The effects of botulinum-A toxin (BTX-A) on striated muscle are well documented in the neurology and plastic surgery literature. Several studies, including a recent randomized, placebo controlled trial, have shown that BTX-A is effective for Neurogenic Detrusor Overactivity (NDO). Uncontrolled case series have shown significant reductions in incontinence and improvement in urodynamic parameters in subjects with idiopathic OAB. Botulinum-A toxin can significantly reduce urge urinary incontinence due to overactive bladder at 6 weeks. However, there is a risk of urinary retention requiring self-catheterization.

While physicians usually suggest surgery to alleviate incontinence only after other treatments have been tried, many surgical options have high rates of success. Urodynamic testing seems to confirm that surgical restoration of vault prolapse can cure motor urge incontinence. One surgical option involves the implantation of stimulation devices that produce electric pulses that cause contraction of the muscles of the pelvis and/or urethra. Such stimulation may strengthen these muscles to help reduce the incidence of urge incontinence. For example, Medtronic produces a device known as InterStim, which is a pulse generator surgically implanted having wires connected to one or more of the sacral nerves. The device is implanted in the back and a wire from the device is connected to the sacral nerve to deliver an electric signal to the nerve. Stimulation of the sacral nerves may activate or inhibit muscles and organs that contribute to urinary control, including the bladder, sphincter and pelvic floor muscles. Traditionally, such stimulators have been implanted using invasive surgical procedures involving the implantation of the stimulator in the abdomen, side or buttock of the patient. Reports suggest, however, that stimulation of the sacral nerve results in a favorable response in about 30-40% of treated women.

Stimulation of the pudendal nerve has also been used to treat urge incontinence. For example, United States Patent Publication Number 2008-0183236, assigned to Medtronic, Inc., describes "[a] method of treating at least one pelvic floor disorder, the at least one disorder being selected from a group consisting of urinary voiding dysfunction, fecal voiding dysfunction, constipation, stress incontinence, urge incontinence, urinary retention disorder, sexual dysfunction, orgasmic dysfunction, erectile dysfunction, pelvic pain, prostatitis, prostatalgia and prostatodynia, the method comprising: delivering first electrical stimulation from a medical device implanted within a patient diagnosed with the pelvic floor disorder to a first pudendal nerve or branches or portions thereof on a first side of the patient via at least one electrode of a first lead implanted within the patient proximate to the pudendal nerve or branches or portions thereof; delivering second electrical stimulation from the medical device to a second pudendal nerve or branches or portions thereof on a second side of the patient via at least one electrode of a second lead implanted within the patient proximate to the second pudendal nerve or branches or portions thereof; and configuring the first and second electrical stimulation to provide at least partial relief from the pelvic floor disorder." In addition to implanting stimulation devices coupled to the pudendal nerve, one common method involves electrical stimulation delivered by an intravaginal or a perineal surface electrode. Although treatment for urge incontinence using implantable stimulators is successful in many instances, the use of conventional implanted devices and methods suffer from certain drawbacks.

Erectile dysfunction (ED), or impotence, is sexual dysfunction characterized by the inability to develop or maintain an erection of the penis during sexual activity. Erectile dysfunction affects 50% of men older than 40 years, exerting substantial effects on quality of life. This common problem is complex and involves multiple pathways. Penile erections are produced by an integration of physiologic processes involving the central nervous, peripheral nervous, hormonal, and vascular systems. Any abnormality in these systems, whether from medication or disease, has a significant impact on the ability to develop and sustain an erection, ejaculate, and experience orgasm. A penile erection results from the hydraulic effect of blood entering and being retained in sponge-like bodies within the penis. The process is often initiated as a result of sexual arousal when signals are transmitted from the brain to nerves in the penis. The most important organic causes for erectile dysfunction include cardiovascular disease and diabetes mellitus (causing neuropathy), neurological problems (for example, trauma from prostatectomy surgery), hormonal insufficiencies (hypogonadism), and drug side effects.

The common penile artery, which derives from the internal pudendal artery, branches into the dorsal, bulbourethral, and cavernous arteries. The dorsal artery provides for engorgement of the glans during erection, whereas the bulbourethral artery supplies the bulb and the corpus spongiosum. The cavernous artery effects tumescence of the corpus cavernosum and thus is principally responsible for erection. The cavernous artery gives off many helicine arteries which supply the trabecular erectile tissue and the sinusoids. These helicine arteries are contracted and tortuous in the flaccid state and become dilated and straight during erection. Venous drainage of the corpora originates in tiny venules that lead from the peripheral sinusoids immediately beneath the tunica albuginea. These venules travel in the trabeculae between the tunica and the peripheral sinusoids to form the subtunical venous plexus before exiting as the emissary veins.

Psychological impotence occurs when erection or penetration fails due to thoughts or feelings (psychological reasons) rather than physical impossibility. Psychological impotence is encountered somewhat less frequently but can often be helped. Notably, in psychological impotence, there is a strong response to placebo treatment. Erectile dysfunction can have severe psychological consequences as it can be tied to relationship difficulties and masculine self-image generally.

The first line treatment of erectile dysfunction consists of a trial of phosphodiesterase type 5 (PDE5) inhibitor drugs (the first of which was sildenafil or Viagra). In some cases, treatment can involve prostaglandin tablets in the urethra, injections into the penis, a penile prosthesis, a penis pump or vascular reconstructive surgery.

Erectile dysfunction is analyzed in several ways. Obtaining full erections at some times, such as nocturnal penile tumescence when asleep (when the mind and psychological issues, if any, are less present), tends to suggest that the physical structures are functionally working.

Penile erection is managed by two mechanisms: the reflex erection, which is achieved by directly touching the penile shaft; and, the psychogenic erection, which is achieved by erotic or emotional stimuli. The former uses the peripheral nerves and the lower parts of the spinal cord, whereas the latter uses the limbic system of the brain. In both conditions, an intact neural system is required for a successful and complete erection. Stimulation of the penile shaft by the nervous system leads to the secretion of nitric oxide (NO), which causes the relaxation of smooth muscles of the corpora cavernosa (the main erectile tissue of penis), and subsequently penile erection. Additionally, adequate levels of testosterone (produced by the testes) and an intact pituitary gland are required for the development of a healthy erectile system. As can be understood from the mechanisms of a normal erection, impotence may develop due to hormonal deficiency, disorders of the neural system, lack of adequate penile blood supply or psychological problems. Restriction of blood flow can arise from impaired endothelial function due to the usual causes associated with coronary artery disease, but can also be caused by prolonged exposure to bright light.

Sexual behavior involves the participation of autonomic and somatic nerves and the integration of numerous spinal and supraspinal sites in the central nervous system (CNS). The penile portion of the process that leads to erections represents only a single component. Several pathways have been described to explain how information travels from the hypothalamus to the sacral autonomic centers. One pathway travels from the dorsomedial hypothalamus through the dorsal and central gray matter, descends to the locus ceruleus, and projects ventrally in the mesencephalic reticular formation. Input from the brain is conveyed through the dorsal spinal columns to the thoracolumbar and sacral autonomic nuclei.

The primary nerve fibers to the penis are from the dorsal nerve of the penis, a branch of the pudendal nerve. The cavernosal nerves are a part of the autonomic nervous system and incorporate both sympathetic and parasympathetic fibers. They travel posterolaterally along the prostate and enter the corpora cavernosa and corpus spongiosum to regulate blood flow during erection and detumescence. The dorsal somatic nerves are also branches of the pudendal nerves. They are primarily responsible for penile sensation.

Erections occur in response to tactile, olfactory, and visual stimuli. The ability to achieve and maintain a full erection depends not only on the penile portion of the process but also on the status of the peripheral nerves, the integrity of the vascular supply, and biochemical events within the corpora. The autonomic nervous system is involved in erection, orgasm, and tumescence. The parasympathetic nervous system is primarily involved in sustaining and maintaining an erection, which is derived from S2-S4 nerve roots.

Sexual stimulation causes the release of neurotransmitters from cavernosal nerve endings and relaxation factors from endothelial cells lining the sinusoids. NOS produces NO from L-arginine, and this, in turn, produces other muscle-relaxing chemicals, such as cGMP and cyclic adenosine monophosphate (cAMP), which work via calcium channel and protein kinase mechanisms. This results in the relaxation of smooth muscle in the arteries and arterioles that supply the erectile tissue, producing a dramatic increase in penile blood flow. Relaxation of the sinusoidal smooth muscle increases its compliance, facilitating rapid filling and expansion. The venules beneath the rigid tunica albuginea are compressed, resulting in near-total occlusion of venous outflow. These events produce an erection with an intracavernosal pressure of 100 mm Hg.

Additional sexual stimulation initiates the bulbocavernous reflex. The ischiocavernous muscles forcefully compress the base of the blood-filled corpora cavernosa, and the penis reaches full erection and hardness when intracavernosal pressure reaches 200 mm Hg or more. At this pressure, both inflow and outflow of blood temporarily cease. Detumescence results from cessation of neurotransmitter release, breakdown of second messengers by phosphodiesterase, and sympathetic nerve excitation during ejaculation. Contraction of the trabecular smooth muscle reopens the venous channels, allowing the blood to be expelled and thereby resulting in flaccidity.

The cyclic nucleotide phosphodiesterases constitute a group of enzymes that destroy the cyclic nucleotides cyclic adenosine monophosphate (cAMP) and cyclic guanosine monophosphate (cGMP). Phosphodiesterases exist in different molecular forms and are unevenly distributed throughout the body. One of the forms of phosphodiesterase is termed PDE5, and inhibiting PDE5 increases the amount of cGMP available in the blood supply to the penis, thus increasing blood flow. The PDE5 inhibitors sildenafil (Viagra), vardenafil (Levitra) and tadalafil (Cialis) are prescription drugs which are taken orally.

A topical cream combining Alprostadil with the permeation enhancer DDAIP has been approved in Canada under the brand name Vitaros as a first line treatment for erectile dysfunction. Another treatment regimen is injection therapy wherein papaverine, phentolamine, and prostaglandin E1 is injected into the penis. A vacuum erection device helps draw blood into the penis by applying negative pressure. This type of device is sometimes referred to as penis pump and may be used just prior to sexual intercourse. Several types of FDA approved vacuum therapy devices are available with a doctor's prescription. When pharmacological methods fail, a purpose-designed external vacuum pump can be used to attain erection, with a separate compression ring fitted to the penis to maintain it. These pumps should be distinguished from other penis pumps (supplied without compression rings) which, rather than being used for temporary treatment of impotence, are claimed to increase penis length if used frequently, or vibrate as an aid to masturbation. More drastically, inflatable or rigid penile implants may be fitted surgically. Often, as a last resort if other treatments have failed, the most common procedure is prosthetic implants which involves the insertion of artificial rods into the penis.

The perineal body (or central tendon of perineum) is a pyramidal fibromuscular mass in the middle line of the perineum at the junction between the urogenital triangle and the anal triangle. It is found in both males and females. In males, it is found between the bulb of penis and the anus. In females, it is found between the vagina and anus, and about 1.25 cm in front of the latter. The perineal body is essential for the integrity of the pelvic floor, particularly in females. Its rupture during vaginal birth leads to widening of the gap between the anterior free borders of levator ani muscle of both sides, thus predisposing the woman to prolapse of the uterus, rectum, or even the urinary bladder. The perineal sponge is a spongy cushion of tissue and blood vessels found in the lower genital area of women. It sits between the vaginal opening and rectum and is internal to the perineum and perineal body. The perineal sponge is composed of erectile tissue. During arousal, it becomes swollen with blood, compressing the outer third of the vagina along with the vestibular bulbs and urethral sponge, thereby creating a tighter fit and additional stimulation for the penis. The perineal sponge is erogenous tissue encompassing a large number of nerve endings, and can, therefore, be stimulated through the back wall of the vagina or the top wall of the rectum.

Female sexual arousal disorder (FSAD), commonly referred to as Candace syndrome, is a disorder characterized by a persistent or recurrent inability to attain sexual arousal or to maintain arousal until the completion of a sexual activity. The diagnosis can also refer to an inadequate lubrication-swelling response normally present during arousal and sexual activity. The condition should be distinguished from a general loss of interest in sexual activity and from other sexual dysfunctions, such as the orgasmic disorder (anorgasmia) and hypoactive sexual desire disorder, which is characterized as a lack or absence of sexual fantasies and desire for sexual activity for some period of time.

Medical conditions are a frequent source of direct or indirect sexual difficulties. Vascular disease associated with diabetes might preclude adequate arousal. Cardiovascular disease may inhibit intercourse secondary to dyspnea. Arthritis or urinary or fecal incontinence may cause discomfort or embarrassment, leading to dysfunction or decreased sexual activity. Gynecologic changes related to a woman's reproductive life (e.g., puberty, pregnancy, the postpartum period and menopause) present unique problems and potential obstacles to sexuality. Puberty may lead to concerns regarding sexual identity. Pregnancy and the postpartum period are often associated with a decrease in sexual activity, desire and satisfaction, which may be prolonged with lactation. The hypoestrogenic state of menopause may cause significant physical changes such as shortening and loss of elasticity of the vaginal barrel, diminished physiologic secretions, rise in vaginal pH from 3.5 to 4.5 to greater than 5, and thinning of epithelial layers.

Physiologically, sexual arousal begins in the medial preoptic, anterior hypothalamic, and limbic-hippocampal structures within the central nervous system. Electrical signals are then transmitted through the parasympathetic and sympathetic nervous systems. Physiologic and biochemical mediators that modulate vaginal and clitoral smooth-muscle tone and relaxation are currently under investigation. Neuropeptide Y, vasoactive intestinal polypeptide, nitric oxide synthase, cyclic guanosine monophosphate, and substance P have been found in vaginal-tissue nerve fibers. Nitric oxide is believed to mediate clitoral and labial engorgement, whereas vasoactive intestinal polypeptide, a nonadrenergic/ noncholinergic neurotransmitter, may enhance vaginal blood flow, lubrication, and secretions. Many changes occur in the female genitalia during sexual arousal. Increased blood flow promotes vasocongestion of the genitalia. Secretions from uterine and Bartholin glands lubricate the vaginal canal. Vaginal smooth muscle relaxation allows for lengthening and dilation of the vagina. As the clitoris is stimulated, its length and diameter increase and engorgement occurs. In addition, the labia minora promote engorgement because of increased blood flow.

There is limited understanding of the precise location of autonomic neurovascular structures related to the uterus, cervix, and vagina. Uterine nerves arise from the inferior hypogastric plexus formed by the union of hypogastric nerves (sympathetic T10-L1) and the splanchnic fibers (parasympathetic S2-S4). This plexus has three portions: Vesical plexus; the rectal plexus; and, the uterovaginal plexus (Frankenhauser's ganglion), which lies at the base of the broad ligament, dorsal to the uterine vessels, and lateral to the uterosacral and cardinal ligament. This plexus provides innervation via the cardinal ligament and uterosacral ligaments to the cervix, upper vagina, urethra, vestibular bulbs and clitoris. At the cervix, sympathetic and parasympathetic nerves form the paracervical ganglia. The larger one is called the uterine cervical ganglion. It is at this level that injury to the autonomic fibers of the vagina, labia, cervix may occur during hysterectomy. The pudendal nerve (S2-S4) reaches the perineum through Alcock's canal and provides sensory and motor innervation to the external genitalia.

The sexual arousal responses of the multiple genital and non-genital peripheral anatomic structures are largely the product of spinal cord reflex mechanisms. The spinal segments are under descending excitatory and inhibitory control from multiple supraspinal sites. The afferent reflex arm is primarily via the pudendal nerve. The efferent reflex arm consists of coordinated somatic and autonomic activity. One spinal sexual reflex is the bulbocavernosus reflex involving sacral cord segments S 2, 3 and 4 in which pudendal nerve stimulation results in pelvic floor muscle contraction. Another spinal sexual reflex involves vaginal and clitoral cavernosal autonomic nerve stimulation resulting in clitoral, labial and vaginal engorgement.

In the basal state, clitoral corporal and vaginal smooth muscles are under contractile tone. Following sexual stimulation, neurogenic and endothelial release of nitric oxide (NO) plays an important role in clitoral cavernosal artery and helicine arteriolar smooth muscle relaxation. This leads to a rise in clitoral cavernosal artery inflow, an increase in clitoral intracavernosal pressure, and clitoral engorgement. The result is extrusion of the glans clitoris and enhanced sensitivity.

In the basal state, the vaginal epithelium reabsorbs sodium from the submucosal capillary plasma transudate. Following sexual stimulation, a number of neurotransmitters including NO and vasoactive intestinal peptide (VIP) are released modulating vaginal vascular and nonvascular smooth muscle relaxation. Dramatic increase in capillary inflow in the submucosa overwhelms Na-reabsorption leading to 3-5 ml of vaginal transudate, enhancing lubrication essential for pleasurable coitus. Vaginal smooth-muscle relaxation results in increased vaginal length and luminal diameter, especially in the distal two-thirds of the vagina. Vasoactive intestinal polypeptide is a non-adrenergic non-cholinergic neurotransmitter that plays a role in enhancing vaginal blood flow, lubrication and secretions. Studies have demonstrated that genital arousal is a neurovascular event characterized by increase in genital blood flow and smooth muscle relaxation. Electrical field stimulation induces non-adrenergic, non-cholinergic relaxation responses in the clitoral corpus cavernosum of the rabbit.

About $\frac{1}{3}^{rd}$ of patients undergoing sacral nerve stimulation report an improvement in their overall sexual experience however, the mechanism of this improvement is unclear. About 20% of patient report worsening in their sexual experience. The improvement in sexual function was independent of improvement in urinary function.

During arousal, blood flow to the vagina, labia and clitoris increases. This causes the organs to swell, the vagina to relax, increasing vaginal lubrication and the sensitivity of the genitalia. Lumbar epidural stimulation has reported spontaneous orgasm in women.

Prior art systems and methods for electrical stimulation address the anal sphincter, on a collective basis, and do not distinguish between internal and external anal sphincter stimulation, which can produce quite different physiological results. The internal anal sphincter is a smooth muscle which is tonically contracted, is not under voluntary control, and is innervated by the submucosal nerve plexus. The internal anal sphincter maintains the tone of the sphincter and is resistant to fatigue. On the other hand, the external anal sphincter is a skeletal muscle which is not tonically contracted, is under voluntary control, and is innervated by the sacral and pudendal nerves, providing the voluntary control to the sphincter muscle, which is extremely susceptible to fatigue. Resting pressure is provided mostly by the internal anal sphincter, whereas squeezing pressure is provided by the external sphincter.

It would therefore be advantageous to stimulate the two sphincters differentially with different stimulation algorithms or different lead configurations due to their distinct physiology and function to prevent fatigue and improve tolerance. Since sphincter control relies on multiple mechanisms, specifically with respect to energy efficiency, tolerance, and fatigue issues, it is advantageous to stimulate multiple structures with different stimulation algorithms. In order to electrically stimulate two anatomical structures, prior art systems and methods would require at least two pairs of stimulation electrodes (that is, at least two microdevices or at least four leads). Due to, anatomical limitation, it may be hard to accommodate or precisely place multiple leads into the anal sphincter. It would, however, be advantageous to put one electrode in each individual structure, thereby using less leads and/or microdevices to achieve the desired stimulation scenario.

Accordingly, there is a need for a safe and effective method of treatment that can help alleviate symptoms of anal incontinence in the long term, without the need for invasive surgery. In addition, there is not only a need for improved devices in electrical stimulation based therapies for anal incontinence, but there is also a need for a safe and minimally invasive method and system that enables easy and expeditious deployment of such devices at any desired location in the body. Most of the currently available devices are available for surgical or laparoscopic implantation and suffer from common problems of pocket infection, lead dislodgment, or fracture. Furthermore, there is also a need for a device and method for implanting microdevices within the rectum or the anal canal.

A need exists, therefore, for an improved treatment for urge incontinence that is more effective than traditional approaches. As discussed above, recent treatment therapies for urge incontinence have focused on electrically stimulating certain nerves innervating particular muscles. However, improved methods are still required to enable effective treatment of various forms of incontinence, as described herein.

Both urinary and fecal incontinence can arise from neurodegenerative disorders of the peripheral sphincter neuromusculature and tend to co-exist in multiple patients. The etiology of both disorders may be similar and may respond to similar therapeutic interventions. In addition, the urinary sphincter is difficult to access, specifically in men, and hence it is desirable to be able to treat a urinary sphincter dysfunction by stimulating an anal sphincter, which is more easily accessed. It is also desirable to stimulate an anal sphincter of a person to improve the function of both an anal sphincter and a urinary sphincter in a patient suffering from a urinary disorder, a fecal disorder, or both.

Prior art systems and methods for electrical stimulation address the anal sphincter and urinary system each on a separate basis. The prior art does not teach a method of treating a urinary sphincter disorder and an anal sphincter disorder on a collective basis by implanting an electrode in either the anal sphincter or the urinary sphincter. Such an approach can have a significant therapeutic advantage of reducing the need for multiple electrode implants into multiple sphincter muscles, hence reducing surgical invasiveness. Additionally, such an approach would reduce the invasiveness associated with reaching a more difficult to access urinary sphincter, especially in men.

It would therefore be advantageous to stimulate the urinary sphincter and the anal sphincter collectively with a single device. The two sphincters could be stimulated with different stimulation algorithms or different lead configurations with respect to their distinct anatomical locations and functions to treat the dysfunction of one or both sphincters. Since sphincter control relies on multiple mechanisms, specifically with respect to energy efficiency, tolerance, and fatigue issues, it is advantageous to stimulate multiple structures with different stimulation algorithms. In order to electrically stimulate two anatomical structures, prior art systems and methods would require at least two pairs of stimulation electrodes comprising at least two microdevices or at least four leads. Due to anatomical separation between the target tissues, device implantation would require more extensive dissection to place multiple leads into the anal sphincter and the urinary sphincter. Therefore, it would be advantageous to put one electrode in either of the individual structures, thereby using less leads and/or microdevices and requiring less dissection to achieve the desired stimulation scenario.

Alternatively, an electrode could be implanted into the urinary sphincter and electrical stimulation would be applied to modulate the function of both the urinary sphincter and the anal sphincter, a desirable approach in women wherein transvaginal access to the urinary sphincter may be less invasive.

Optionally, an electrode could be implanted into the anal sphincter and electrical stimulation would be applied to modulate the function of both the urinary sphincter and the anal sphincter, a desirable approach in men wherein access to the urinary sphincter is more difficult.

Such approaches are desirable in patients suffering from disorders of both the urinary sphincter and the anal sphincter or in patients suffering from a disorder of one sphincter and at future risk of a disorder of the other sphincter.

A need exists, therefore, for an improved treatment for urinary incontinence that is more effective than traditional approaches. As discussed above, recent treatment therapies for urinary incontinence have focused on electrically stimulating certain nerves innervating particular muscles. However, improved methods are still required to enable effective treatment of various forms of urinary incontinence, as described herein.

SUMMARY

The present specification discloses a method for improving a function of a urinary sphincter of a patient using a stimulation device, wherein the stimulation device comprises at least one electrode operably connected to a stimulus generator and a controller configured to transmit at least one stimulation signal to the stimulus generator, the method comprising: implanting the device in an anorectal region of the patient; positioning the electrode in electrical communication with a target tissue within said anorectal region of the patient; generating a stimulation signal using said controller based on a plurality of programmatic instructions stored within said controller; and generating an electrical stimulation pulse, in response to said stimulation signal, using the stimulus generator, wherein said electrical stimulation pulse is transmitted to said target tissue within said anorectal region via said at least one electrode.

Optionally, the target tissue comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

Optionally, the electrical stimulation pulse comprises a pulse width having a range of 10 μsec to 500 msec, a pulse amplitude of 1 μAmp to 100 mAmp, and a pulse frequency of 0.02 Hz to 100 Hz.

Optionally, the device further comprises at least one sensor configured to obtain data and said method further comprises modifying said electrical stimulation pulse based on the data from the at least one sensor. The at least one sensor may comprise a pressure sensor, an electrical activity sensor, an impedance sensor, an accelerometer, or an inclinometer.

Optionally, after an application of said electrical stimulation pulse, an abdominal leak point pressure increases by at least five percent or at least 60 cm $H_2O$ relative to an abdominal leak point pressure prior to said application of said electrical stimulation pulse.

Optionally, after an application of said electrical stimulation pulse, an abdominal leak point volume increases by at least five percent or at least 50 cc relative to an abdominal leak point volume prior to said application of said electrical stimulation pulse.

Optionally, after an application of said electrical stimulation pulse, a post void residual urine volume determination increases by at least five percent relative to a post void residual urine volume determination prior to said application of said electrical stimulation pulse.

Optionally, after an application of said electrical stimulation pulse, uroflowmetry increases by at least five percent relative to uroflowmetry prior to said application of said electrical stimulation pulse.

Optionally, after an application of said electrical stimulation pulse, a bladder compliance increases by at least five percent or at least 20 ml/cm $H_2O$ relative to a bladder compliance prior to said application of said electrical stimulation pulse.

Optionally, after an application of said electrical stimulation pulse, a detrusor leak point pressure increases by at least five percent or at least 40 cm $H_2O$ relative to a detrusor leak point pressure prior to said application of said electrical stimulation pulse.

Optionally, after an application of said electrical stimulation pulse, a first sensation volume increases by at least 5% or at least 50 ml relative to a first sensation volume prior to said application of said electrical stimulation pulse.

Optionally, after an application of said electrical stimulation pulse, a second sensation (full) volume increases by at least 5% or at least 200 ml relative to a second sensation (full) volume prior to said application of said electrical stimulation pulse.

Optionally, after an application of said electrical stimulation pulse, a bladder maximum capacity increases by at least 5% or at least 400 ml relative to a bladder maximum capacity prior to said application of said electrical stimulation pulse.

Optionally, after an application of said electrical stimulation pulse, a maximum detrusor pressure increase by at least 5% or at least 20 cm $H_2O$ relative to a maximum detrusor pressure prior to said application of said electrical stimulation pulse.

Optionally, after an application of said electrical stimulation pulse, a detrusor contractility increases by at least 5% but no greater than 25% relative to a detrusor contractility prior to said application of said electrical stimulation pulse.

Optionally, after an application of said electrical stimulation pulse, a number of incontinence episodes or a mean incontinence volume per incontinence episode is decreased by at least 5% relative to a number of incontinence episodes or a mean incontinence volume per incontinence episode prior to said application of said electrical stimulation pulse.

Optionally, after an application of said electrical stimulation pulse, a total voided volume increases by at least 5% relative to a total voided volume prior to said application of said electrical stimulation pulse.

Optionally, after an application of said electrical stimulation pulse, a mean voided volume increases by at least 5% relative to a mean voided volume prior to said application of said electrical stimulation pulse.

Optionally, after an application of said electrical stimulation pulse, a largest single voided volume increases by at least 5% relative to a largest single voided volume prior to said application of said electrical stimulation pulse.

Optionally, after an application of said electrical stimulation pulse, patient incontinence perception scores on a visual analog scale improve by at least 5% relative to patient incontinence perception scores on a visual analog scale prior to said application of said electrical stimulation pulse.

Optionally, after an application of said electrical stimulation pulse, a Stamey's incontinence score improves by at least 1 grade relative to a Stamey's incontinence score prior to said application of said electrical stimulation pulse.

Optionally, after an application of said electrical stimulation pulse, a urogenital distress inventory (UDI) for women increases by at least 5% relative to a urogenital distress inventory (UDI) for women prior to said application of said electrical stimulation pulse.

Optionally, after an application of said electrical stimulation pulse, a severity index for urinary incontinence in women increases by at least 5% or improves by at least 1 point relative to a severity index for urinary incontinence in women prior to said application of said electrical stimulation pulse.

Optionally, after an application of said electrical stimulation pulse, a leakage index for women with stress incontinence increases by at least 5% relative to a leakage index for women with stress incontinence prior to said application of said electrical stimulation pulse.

Optionally, after an application of said electrical stimulation pulse, pad testing (1 hour and 24 hour) testing results improve by at least 5% relative to pad testing (1 hour and 24 hour) testing prior to said application of said electrical stimulation pulse.

Optionally, after an application of said electrical stimulation pulse, quality of life scores on SF6, SF12, and Roger Goldberg scales increases by at least 5% relative to quality of life scores on SF6, SF12, and Roger Goldberg scales prior to said application of said electrical stimulation pulse.

The present specification also discloses a device for treating a fecal dysfunction of a patient, comprising: a first electrode configured to contact a first tissue region; a second electrode configured to contact a second tissue region; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; and wherein said pulse width, pulse amplitude, pulse frequency and duty cycle for the electrical pulses transmitted to the first electrode and second electrode are defined such that, after an application of said electrical pulses, a fecal dysfunction parameter measured by anorectal manometry improves by at least 5% relative to pre-treatment values.

Optionally, said fecal dysfunction parameter includes any one of internal anal sphincter resting pressure, external anal sphincter resting pressure, anal sphincter squeeze pressure, stress testing (abdominal leak-point pressure), stress testing (abdominal leak-point volume), anal high pressure zone, anal squeeze duration, first sensation volume, desire to defecate volume, urgency volume, balloon expulsion time, rectal pressure during evacuation, and anal pressure during evacuation.

Optionally, the first tissue region comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

Optionally, the second tissue region comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

The second tissue region may be separate and distinct from the first tissue region.

The electrical pulses transmitted to the first electrode may have the same or a different pulse width, pulse amplitude, or pulse frequency than the electrical pulses transmitted to the second electrode.

Optionally, the device further comprises at least one sensor configured to obtain data, wherein said waveform generator is configured to use said data to modify at least one of the electrical pulses transmitted to the first electrode and the electrical pulses transmitted to the second electrode. The at least one sensor may comprise a pressure sensor, an electrical activity sensor, an impedance sensor, an accelerometer, or an inclinometer.

Optionally, the device further comprises a controller adapted to modify at least one of the electrical pulses transmitted to the first electrode and the electrical pulses transmitted to the second electrode based upon an input from said patient.

Optionally, the device further comprises a transceiver for receiving and transmitting data and/or power from outside the patient's body through inductive, radiofrequency (RF), electrical, magnetic, optical or other electromagnetic coupling.

Optionally, the device further comprises an integrated circuit (IC) chip for decoding and storing a plurality of stimulation parameters and generating said electrical pulses and a programmable memory for storing data and stimulation parameters.

The present specification also discloses a device for improving a fecal dysfunction of a patient, comprising: a first electrode configured to contact a first tissue region; a second electrode configured to contact a second tissue region; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; and wherein said pulse width, pulse amplitude, pulse frequency and duty cycle for the electrical pulses transmitted to the first electrode and second electrode are defined such that, after an application of said electrical pulses, a variable score obtained by any one of a Rothenberger scale, Wexner scale, Vaizey scale, or Fecal Incontinence Severity Index (FISI) scale improves by at least 5% relative to a pre-treatment score.

Optionally, the first tissue region comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

Optionally, the second tissue region comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

The second tissue region may be separate and distinct from the first tissue region.

The electrical pulses transmitted to the first electrode may have the same or a different pulse width, pulse amplitude, or pulse frequency than the electrical pulses transmitted to the second electrode.

Optionally, the device further comprises at least one sensor configured to obtain data, wherein said waveform generator is configured to use said data to modify at least one of the electrical pulses transmitted to the first electrode and the electrical pulses transmitted to the second electrode. The at least one sensor may comprise a pressure sensor, an electrical activity sensor, an impedance sensor, an accelerometer, or an inclinometer.

The present specification also discloses a device for improving a fecal dysfunction of a patient, comprising: a first electrode configured to contact a first tissue region; a second electrode configured to contact a second tissue region; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; and wherein said pulse width, pulse amplitude, pulse frequency and duty cycle for the electrical pulses transmitted to the first electrode and second electrode are defined such that, after an application of said electrical pulses, any one or combination of a visual analog score and a quality of life score improves by at least 5% relative to a pre-treatment scores.

The present specification also discloses a device for improving a urinary sphincter function of a patient, comprising: a first electrode configured to contact a first tissue region, wherein said first tissue region is not in physical contact with an internal urinary sphincter of the patient; a second electrode configured to contact a second tissue region, wherein said second tissue region not in physical contact with said internal urinary sphincter of the patient; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; and wherein said pulse width, pulse amplitude, pulse frequency and duty cycle for the electrical pulses transmitted to the first electrode and second electrode are defined such that, after an application of said electrical pulses, an abdominal leak pressure increases by at least five percent relative to an abdominal leak pressure prior to said application of said electrical pulses or such that, after an application of said electrical pulses, an abdominal leak volume increases by at least five percent relative to an abdominal leak volume prior to said application of said electrical pulses.

The first tissue region may comprise at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

The second tissue region may comprise at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

Optionally, the second tissue region is separate and distinct from the first tissue region.

Optionally, the electrical pulses transmitted to the first electrode have a different pulse width, pulse amplitude, or pulse frequency than the electrical pulses transmitted to the second electrode.

Optionally, the electrical pulses transmitted to the first electrode have a pulse width, a pulse amplitude, and a pulse frequency that is equal to a pulse width, a pulse amplitude, and a pulse frequency of the electrical pulses transmitted to the second electrode.

Optionally, the device further comprises at least one sensor configured to obtain data, wherein said waveform generator is configured to use said data to modify at least one of the electrical pulses transmitted to the first electrode and the electrical pulses transmitted to the second electrode. The sensor may comprise a pressure sensor, an electrical activity sensor, an impedance sensor, an accelerometer, or an inclinometer.

Optionally, the device further comprises a controller adapted to modify at least one of the electrical pulses transmitted to the first electrode and the electrical pulses transmitted to the second electrode based upon an input from said patient.

Optionally, the device further comprises a transceiver for receiving and transmitting data and/or power from outside the patient's body through inductive, radiofrequency (RF), electrical, magnetic, optical or other electromagnetic coupling.

Optionally, the device further comprises an integrated circuit (IC) chip for decoding and storing a plurality of stimulation parameters and generating said electrical pulses and a programmable memory for storing data and stimulation parameters.

The first electrode may be at least 1 cm away from the internal urinary sphincter of the patient.

The second electrode may be at least 1 cm away from the internal urinary sphincter of the patient.

The present specification also discloses a device for improving a urinary sphincter function of a patient, comprising: a first electrode configured to contact a first tissue region, wherein said first tissue region is at least 1 cm away from an internal urinary sphincter; a second electrode configured to contact a second tissue region, wherein said second tissue region is at least 1 cm away from the internal urinary sphincter; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; wherein said pulse width, pulse amplitude, pulse frequency and duty cycle for the electrical pulses transmitted to the first electrode and second electrode are defined such that, after an application of said electrical pulses, a urine volume, as measured by a weight change in an absorbent pad, decreases by at least five percent as compared to a urine volume absent said application of said electrical pulses.

The first tissue region may comprise at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

The second tissue region may comprise at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep parts of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, vaginal tissue, and perineal tissue.

Optionally, the second tissue region is separate and distinct from the first tissue region.

Optionally, the electrical pulses transmitted to the first electrode have a different pulse width, pulse amplitude, or pulse frequency than the electrical pulses transmitted to the second electrode.

Optionally, the electrical pulses transmitted to the first electrode have a pulse width, a pulse amplitude, and a pulse frequency that is equal to a pulse width, a pulse amplitude, and a pulse frequency of the electrical pulses transmitted to the second electrode.

Optionally, the device further comprises at least one sensor configured to obtain data, wherein said waveform generator is configured to use said data to modify at least one of the electrical pulses transmitted to the first electrode and the electrical pulses transmitted to the second electrode. The sensor may comprise a pressure sensor, an electrical activity sensor, an impedance sensor, an accelerometer, or an inclinometer.

The present specification also discloses a device for improving a urinary sphincter function of a patient, comprising: a first electrode configured to contact a first tissue region, wherein said first tissue region is not in physical contact with the internal urinary sphincter; a second electrode configured to contact a second tissue region, wherein said second tissue region is not in physical contact with the internal urinary sphincter; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; wherein said pulse width, pulse amplitude, pulse frequency and duty cycle for the electrical pulses transmitted to the first electrode and second electrode are defined such that a number of incontinent episodes or a mean incontinence volume per episode decreases by at least five percent.

In one embodiment, the present specification describes a method of treating anorectal dysfunction in a patient, comprising the following steps: providing a device comprising at least a first electrode and a second electrode operably connected to a stimulus generator configured to receive at least one stimulation signal from a controller; implanting said device in the anorectal tissue of the patient; positioning said first electrode in electrical communication with a first target tissue within the anorectal region of the patient; positioning said second electrode in electrical communication with a second target tissue within the anorectal region of the patient, wherein said second target tissue is distinct and different from said first target tissue; causing said controller to generate a first stimulation signal, based on a first programmed algorithm and a second stimulation signal, based on a second programmed algorithm, that are transmitted to the stimulus generator; and, the stimulus generator, in response to the first stimulation signal generating a first electrical stimulation pulse that is transmitted to said first target tissue via said first electrode and in response to the second stimulation signal generating a second electrical stimulation pulse that is transmitted to said second target tissue via said second electrode.

In one embodiment, said first target tissue and said second target tissue are chosen from any of the following: the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, or the submucosal (Meissner's) plexus of the anorectum.

In one embodiment, said first stimulation algorithm and said second algorithm are programmable and generate pulse trains, wherein said pulse trains are variable in the number of pulses per pulse train, the shape of pulses in a pulse train, the interval between pulse train repetitions, the duration of each pulse, the timing and amplitude of pulses in each train, the desired amount of amperage or potential to be provided, and the shape of each train, wherein the shape is chosen from any one of the following: a square, rectangular, sinusoidal, or saw tooth shape.

In one embodiment, said first stimulation algorithm is the same as said second stimulation algorithm. In another embodiment, said first stimulation algorithm is different than said second stimulation algorithm.

In one embodiment the first stimulation algorithm is programmed into the device to be automatically delivered to the patient and the second stimulation algorithm is delivered by the patient using an external input. The first stimulation is delivered to predominantly modulate the function of the internal anal sphincter, while the second stimulation algorithm is delivered to predominantly modulate the function of the external anal sphincter. The first stimulation algorithm is delivered continuously or at regular intervals, while the second stimulation algorithm is delivered intermittently on as need basis.

In one embodiment, in which the first and second stimulation algorithms are the same, the same stimulation algorithm is delivered through each electrode while one electrode functions as a depolarizing electrode and the other electrode functions as a hyperpolarizing electrode. In one embodiment, when stimulation of the internal anal sphincter is desired, the electrode proximate the internal anal sphincter will be the depolarizing electrode. In one embodiment, when stimulation of the external anal sphincter is desired, the electrode proximate the external anal sphincter will be the depolarizing electrode and the alternate electrode will be the hyperpolarizing electrode.

In one embodiment, said device further comprises at least one sensor, wherein said sensor detects at least one parameter, further wherein data obtained by said sensor is used to modify said first stimulation algorithm and/or said second stimulation algorithm. In one embodiment, said sensor comprises a pressure sensor, an electrical activity sensor, an impedance sensor, an accelerometer, or an inclinometer.

In one embodiment, said device further comprises a controller designed to be operated by said patient, wherein the patient is capable of modifying and activating said first stimulation algorithm and/or said second algorithm.

In one embodiment, the patient is provided with a handheld device to initiate stimulation while in another embodiment the patient can perform a maneuver which is sensed by an internal sensor to trigger the delivery of a specific stimulation. For example, a patient may initiate a squeeze that is sensed by an internal pressure sensor to deliver a stimulation specific for the external anal sphincter to raise the external anal sphincter tone.

In another embodiment the device can be programmed based on patient's clinical symptoms, rectal manometry data or other clinical or investigational data to program a patient specific stimulation algorithm.

In one embodiment, two or more stimulation algorithms can serve different functions. For example, a stimulating algorithm configured to raise muscle tone can be combined with a blocking pulse to block the sensation arising from the patient's rectum or anal canal to block the patient's urge to defecate.

In one embodiment, the specification describes a device for treating anorectal dysfunction in a patient, comprising: a microcontroller, comprising a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters; a stimulus generator; a power source; and, at least two electrodes for implantation into and stimulation of anorectal tissue.

In one embodiment, the device for treating anorectal dysfunction in a patient further comprises at least one sensor as described above. In one embodiment, the device further comprises at least one anchor used to anchor the device in the rectum or the anal canal. In one embodiment, the device further comprises a controller designed to be operated by said patient as described above.

In one embodiment, the present specification describes a catheter device for implanting a microdevice in the anorectum, comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice.

In one embodiment, the present specification describes a device for assisting in the implantation of a microdevice in the anorectum, comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a mechanism for creating a suction to draw a portion of anorectal tissue in through the slot and into the distal portion; and, a channel extending through said proximal portion and into said distal portion for the passage of a catheter or needle. Optionally, a vacuum is provided by applying suction from an external source to said device. Optionally, a gauge is used to measure and standardize the amount of vacuum created.

In one embodiment, the present specification describes a method for implanting a microdevice in the anorectal region of a patient, comprising the steps of: providing an insertion device, said insertion device comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a mechanism for creating a suction to draw a portion of anorectal tissue in through the slot and into the distal portion; and, a channel extending through said proximal portion and into said distal portion for the passage of a catheter or needle; providing a catheter, said catheter comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice; inserting said insertion device into a patient's rectum; creating suction to draw in a portion of anorectal tissue into said insertion device; inserting said catheter into said channel of said insertion device; extending said pusher with an attached microdevice past the distal open end of said sheath, causing said sharp bend to partially expand; pulling said pusher back into said sheath, causing said microdevice to become engaged with said anorectal tissue; fully retracting said pusher into said sheath, causing said microdevice to detach from said pusher and remain in said anorectal tissue; pushing said plunger into said insertion device to release said portion of anorectal tissue; and, removing said insertion device from the patient's rectum.

In one embodiment, the present specification describes a system for treating anorectal dysfunction in a patient, comprising: at least one electro-medical device, said electro-medical device comprising a microcontroller, said microcontroller comprising a transceiver for receiving and transmitting data and/or power from outside the patient's body through inductive, radiofrequency (RF), electrical, magnetic, ultrasound, optical or other electromagnetic coupling; an integrated circuit (IC) chip for decoding and storing a plurality of stimulation parameters and generating a plurality of stimulation pulses; and, a programmable memory for storing sets of data, stimulation, and control parameters; a stimulus generator; a power source; and, at least two electrodes for implantation into and stimulation of anorectal tissue; a catheter for implanting said electro-medical device, said catheter comprising: an elongate sheath having a proximal open end and a distal open end; an elongate pusher slidably movable within said sheath, comprising: a proximal end and a distal end; a sharp bend proximate said distal end; and, an attachment point at its distal end, distal to said sharp bend, for the attachment of said microdevice; and, an insertion device for assisting in said implantation, said insertion device comprising: a conical, distal portion comprising: a distal end and a proximal end, wherein said distal end has a smaller diameter than said proximal end; a rectangular slot for capturing a portion of anorectal tissue; an opening at said distal end; and, a moveable valve covering said opening at said distal end; a cylindrical, proximal portion, comprising: a distal end and a proximal end, wherein said distal end is attached to and in open communication with, said proximal end of said distal portion; and, a handle; a mechanism for creating a suction to draw a portion of anorectal tissue in through the slot and into the distal portion; and, a channel extending through said proximal portion and into said distal portion for the passage of a catheter or needle.

The present specification also discloses a method of treating urinary dysfunction in a patient, comprising the following steps: providing a device comprising at least a first electrode and a second electrode operably connected to a stimulus generator configured to receive at least one stimulation signal from a controller; implanting said device in the patient; positioning said first electrode in electrical communication with a first target tissue within said anorectal tissue or genitourinary tissue of the patient; positioning said second electrode in electrical communication with a second target tissue within said anorectal tissue or genitourinary tissue of the patient, wherein said second target tissue is distinct and different from said first target tissue; causing said controller to generate a first stimulation signal based on a first programmed algorithm and a second stimulation signal based on a second programmed algorithm, that are transmitted to the stimulus generator; and, the stimulus generator, in response to the first stimulation signal generating a first electrical stimulation pulse that is transmitted to said first target tissue via said first electrode, and in response to second stimulation signal generating a second electrical stimulation pulse that is transmitted to said second target tissue via said second electrode.

The first target tissue and second target tissue may be chosen from any of the following: the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, the submucosal (Meissner's) plexus of the anorectum, or a genitourinary tissue of the patient.

The first stimulation algorithm and second algorithm may be programmable and generate pulse trains, wherein said pulse trains are variable in the number of pulses per pulse train, the shape of pulses in a pulse train, the interval between pulse train repetitions, the duration of each pulse, the timing and amplitude of pulses in each train, the desired amount of amperage or potential to be provided, and the shape of each train, wherein the shape is chosen from any one of the following: a square, rectangular, sinusoidal, or saw tooth shape.

The first stimulation algorithm may be the same as or different from the second stimulation algorithm.

Optionally, the device further comprises at least one sensor, wherein said sensor detects at least one parameter, further wherein data obtained by said sensor is used to modify said first stimulation algorithm and/or said second stimulation algorithm. The sensor may comprise a pressure sensor, an electrical activity sensor, an impedance sensor, an accelerometer, or an inclinometer.

Optionally, the device further comprises a controller designed to be operated by said patient, wherein the patient is capable of modifying and activating said first stimulation algorithm and/or said second algorithm.

The present specification also discloses a device for treating urinary dysfunction in a patient, comprising: a microcontroller, comprising a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters; a stimulus generator; a power source; and, at least two electrodes for implantation into and stimulation of an anorectal tissue or genitourinary tissue of the patient.

Optionally, the device further comprises at least one sensor, wherein said sensor comprises a pressure sensor, an electrical activity sensor, an impedance sensor, an accelerometer, or an inclinometer.

Optionally, the device further comprises at least one anchor used to anchor the device in the rectum or the anal canal.

Optionally, the device further comprises a controller designed to be operated by said patient, wherein the patient is capable of modifying and activating said first stimulation algorithm and/or said second algorithm.

The present specification also discloses a method of modulating the function of an internal anal sphincter in a patient, comprising the following steps: providing a device comprising at least a first electrode and a second electrode operably connected to a stimulus generator configured to receive an electrical signal from a controller; implanting said device in the anorectal tissue of the patient; positioning said first electrode in electrical communication with a first target tissue within the anorectal region of the patient; positioning said second electrode in electrical communication with a second target tissue within the anorectal region of the patient, wherein said second target tissue is same or distinct and different from said first target tissue; and, causing said controller, based on a programmed stimulation algorithm, to generate an electrical stimulation that is transmitted to the stimulus generator which, in response to the electrical signal, generates an electrical stimulation pulse, wherein said electrical stimulation pulse is adapted to modulate the function of an internal anal sphincter that lasts beyond the cessation of such stimulation.

The modulation of a function of the internal anal sphincter may last for at least 5 minutes after the cessation of the stimulation.

The present specification also discloses a method of modulating the function of an internal anal sphincter in a patient, comprising the following steps: providing a device comprising at least a first electrode and a second electrode operably connected to a stimulus generator configured to receive an electrical signal from a controller; implanting said device in the anorectal tissue of the patient; positioning said first electrode in electrical communication with a first target tissue within the anorectal region of the patient; positioning said second electrode in electrical communication with a second target tissue within the anorectal region of the patient, wherein said second target tissue is same or distinct and different from said first target tissue; and, causing said controller, based on a programmed stimulation algorithm, to generate an electrical stimulation that is transmitted to the stimulus generator which, in response to the electrical signal, generates an electrical stimulation pulse, wherein said electrical stimulation pulse is adapted to modulate the function of an internal anal sphincter wherein such modulation of the internal anal sphincter function is further modulated by rectal distension.

The additional modulation of the internal anal sphincter function by rectal distension may result in an increase or a decrease by at least 10% of the initial modulation in the function due to the stimulation.

The present specification also discloses a method of treating urinary dysfunction in a patient, comprising the following steps: implanting a device comprising a plurality of electrode operably connected to an electrical stimulus generator and placed proximate to the anorectal tissue of the patient; and causing said stimulus generator to deliver an electrical pulse via said electrode to the anorectal tissue of the patient to cause a stimulation of said anorectal tissue of the patient; wherein the delivery of said electrical pulse substantially modulates a urinary function.

The stimulus generator may deliver an electrical pulse through the second electrode to substantially modulate a urinary sphincter pressure.

The present specification also discloses a method of modulating a function of an urinary sphincter in a patient, comprising the following steps: implanting a stimulus generator, wherein said stimulus generator is operably connected to a first electrode and a second electrode and is configured to receive an electrical signal form a controller; implanting said first electrode proximate to an patient's anorectal region; implanting said second electrode proximate to another region in the patient's anorectal region; causing said controller, based on a first programmed stimulation algorithm, to generate a first electrical stimulation that is transmitted to the stimulus generator which, in response to the first electrical signal, generates a first electrical stimulation pulse, wherein said first electrical stimulation pulse is adapted to modulate an anorectal function; and causing said controller, based on a second programmed stimulation algorithm, to generate a second electrical stimulation that is transmitted to the stimulus generator which, in response to the second electrical signal, generates a second electrical stimulation pulse, wherein said second electrical stimulation pulse is adapted to modulate a urinary function; wherein the delivery of said first electrical stimulation pulse and said second electrical stimulation pulse substantially modulates a composite anorectal and a urinary function.

The present specification also discloses a method of modulating symptoms of anorectal disorder in a subject in need thereof, comprising: providing an electrical signal; and delivering the electrical signal to a portion of a region encompassing said ano-rectum for a certain duration, wherein said region comprises the anal sphincter and 5 cm above the anal sphincter, to stimulate the anal sphincter and to improve the symptoms of anorectal disorder wherein said electrical signal is adapted to cause said symptom decrease to be maintained for a period of at least 24 hour after stimulation ceases.

The duration may be greater than 24 hours.

The electrical signal may be continuous or intermittent.

The present specification also discloses a method of modulating anal sphincter function in a subject in need thereof, comprising: providing an electrical signal; and delivering the electrical signal to a portion of a region encompassing said ano-rectum for a certain duration, wherein said region comprises the anal sphincter and 5 cm above or radially around the anal sphincter, to stimulate the anal sphincter and to improve the sphincter function, wherein said electrical signal is adapted to cause said sphincter function improvement to be maintained for a period of at least 24 hour after stimulation ceases.

The duration may be greater than 24 hours.

The electrical signal may be continuous or intermittent.

The present specification also discloses a method of modulating anal sphincter function in a subject in need thereof, comprising: providing an electrical signal; and delivering the electrical signal to a portion of a region encompassing an ano-rectum of the subject for a certain duration, wherein said region comprises the anal sphincter and 5 cm radially around, or proximate the anal sphincter, to stimulate the anal sphincter and to improve the sphincter function, wherein said electrical signal is adapted to cause said sphincter function improvement to be maintained for a period of at least one hour after stimulation ceases.

The duration may be greater than one hour.

The electrical signal may be continuous or intermittent.

The present specification also discloses a method of treating urinary dysfunction in a patient, comprising the following steps: providing a device comprising at least one electrode operably connected to a stimulus generator; implanting said device proximate an anorectal region of the patient and positioning said electrode in electrical communication with a target tissue within the anorectal region of the patient; and, causing said stimulus generator to generate an electrical stimulation, wherein said electrical stimulation is transmitted to said target tissue via said electrode; wherein the said electrical stimulation improves a urinary function.

The present specification also discloses a method of modulating urinary sphincter function in a subject in need thereof, comprising: providing an electrical signal; and delivering the electrical signal to a portion of a region encompassing an ano-rectum of the subject for a certain duration, wherein said region comprises the anal sphincter and 5 cm radially around the anal sphincter, to stimulate the anal sphincter and to improve the urinary sphincter function, wherein said electrical signal is adapted to cause said urinary sphincter function improvement to be maintained for a period of at least 24 hour after stimulation ceases.

The duration may be greater than 24 hours.

The electrical signal may be continuous or intermittent.

The present specification also discloses a method of modulating urinary sphincter function in a subject in need thereof, comprising: providing an electrical signal; and delivering the electrical signal to a portion of a region encompassing an ano-rectum of the subject for a certain duration, wherein said region comprises the anal sphincter and 5 cm radially around the anal sphincter, to stimulate the anal sphincter and to improve the urinary sphincter function, wherein said electrical signal is adapted to cause said urinary sphincter function improvement to be maintained for a period of at least one hour after stimulation ceases.

The duration may be greater than one hour.

The electrical signal may be continuous or intermittent.

The present specification also discloses a method of treating a sexual dysfunction in a patient, comprising the following steps: implanting a device comprising a plurality of electrodes operably connected to an electrical stimulus generator and placed proximate an anorectal tissue of the patient; and causing said stimulus generator to deliver an electrical pulse via said electrodes to the anorectal tissue of the patient to cause a stimulation of said anorectal tissue of the patient, wherein the delivery of said electrical pulse substantially treats a sexual dysfunction.

The present specification also discloses a method of treating a sexual dysfunction in a patient, comprising the following steps: implanting a device comprising a plurality of electrodes operably connected to an electrical stimulus generator and placed proximate a genitourinary tissue of the patient; and causing said stimulus generator to deliver an electrical pulse via said electrode to the genitourinary tissue of the patient to cause a stimulation of said genitourinary tissue of the patient, wherein the delivery of said electrical pulse treats a sexual dysfunction.

Optionally, the stimulation is timed to a urinary function, a bowel function or a sexual function. Optionally, the stimulation is delivered independent of a urinary function, a bowel function or a sexual function and, after at least a single session of stimulation, results in improvement in at least one of the above mentioned functions that lasts beyond the duration of stimulation.

Optionally, the stimulation is delivered to instantaneously improve a urinary function, a bowel function or a sexual function. Optionally, the stimulation is delivered to slowly improve a urinary function, a bowel function or a sexual function over time. Optionally, the improvement in one of the above mentioned functions occurs at least 5 minutes after the initiation of stimulation.

The present specification also discloses a device for improving a sexual function of a patient, comprising: a first electrode configured to contact a first tissue region; a second electrode configured to contact a second tissue region; a waveform generator coupled to the first electrode and second electrode, wherein the waveform generator is configured to generate electrical pulses to the first electrode and second electrode and wherein said electrical pulses comprise a pulse width having a range of 10 μsec to 500 msec; a pulse amplitude of 1 μAmp to 100 mAmp; and a pulse frequency of 0.02 Hz to 100 Hz; wherein said pulse width, pulse amplitude, pulse frequency and duty cycle for the electrical pulses transmitted to the first electrode and second electrode are defined such that, after an application of said electrical pulses: the number of successful or satisfactory sexual events or encounters over time as measured in a patient daily diary increases by at least five percent relative to the number of successful or satisfactory sexual events or encounters over time as measured in a patient daily diary prior to said application of said electrical pulses; Sexual Dysfunction Questionnaire (SDQ) scores improve by at least five percent relative to Sexual Dysfunction Questionnaire (SDQ) scores prior to stimulation; sexual desire as measured in a patient daily diary increases by at least five percent prior to stimulation; or Golombok Rust Inventory of Sexual Satisfaction (GRISS) scores improve by at least five percent relative to Golombok Rust Inventory of Sexual Satisfaction (GRISS) scores prior to stimulation.

The aforementioned and other embodiments of the present specification shall be described in greater depth in the drawings and detailed description provided below.

BRIEF DESCRIPTION OF THE DRAWINGS

These and other objects and advantages of the present specification will become more fully apparent from the following detailed description when read in conjunction with the accompanying drawings with like reference numerals indicating corresponding parts through-out, wherein:

FIG. 13A is an illustration of one embodiment of an exemplary configuration of an implantation catheter with a pusher and attached microdevice arranged predominantly parallel to each other within said catheter;

FIG. 13B is an illustration of the same embodiment of an exemplary configuration of an implantation catheter of FIG. 13A, depicting the microdevice being pushed out of said catheter using the pusher;

FIG. 13C is an illustration of the same embodiment of an exemplary configuration of an implantation catheter of FIG. 13A, depicting the microdevice fully pushed out of said catheter;

FIG. 13D is an illustration of the same embodiment of an exemplary configuration of an implantation catheter of FIG. 13A, depicting the pusher being pulled back into said catheter;

FIG. 13E is an illustration of the same embodiment of an exemplary configuration of an implantation catheter of FIG. 13A, depicting the pusher pulled back completely into said catheter, thereby disconnecting from the microdevice that is implanted in a tissue site;

FIG. 21 is a table for a Sexual Dysfunction Questionnaire (SDQ) listing a series of statements about a patient's sexuality with scores;

FIG. 22 is a table illustrating various parameters measured to determine improvement in fecal incontinence when treated using the systems and methods of the present specification;

FIG. 23A is a table illustrating the methodology of various scoring systems in measuring fecal incontinence;

FIG. 23B is another table illustrating the methodology of various scoring systems in measuring fecal incontinence;

FIG. 32 is a flowchart illustrating a method of treating a fecal dysfunction and a urinary dysfunction in a patient, in accordance with another embodiment of the present specification;

DETAILED DESCRIPTION

Figure 1:
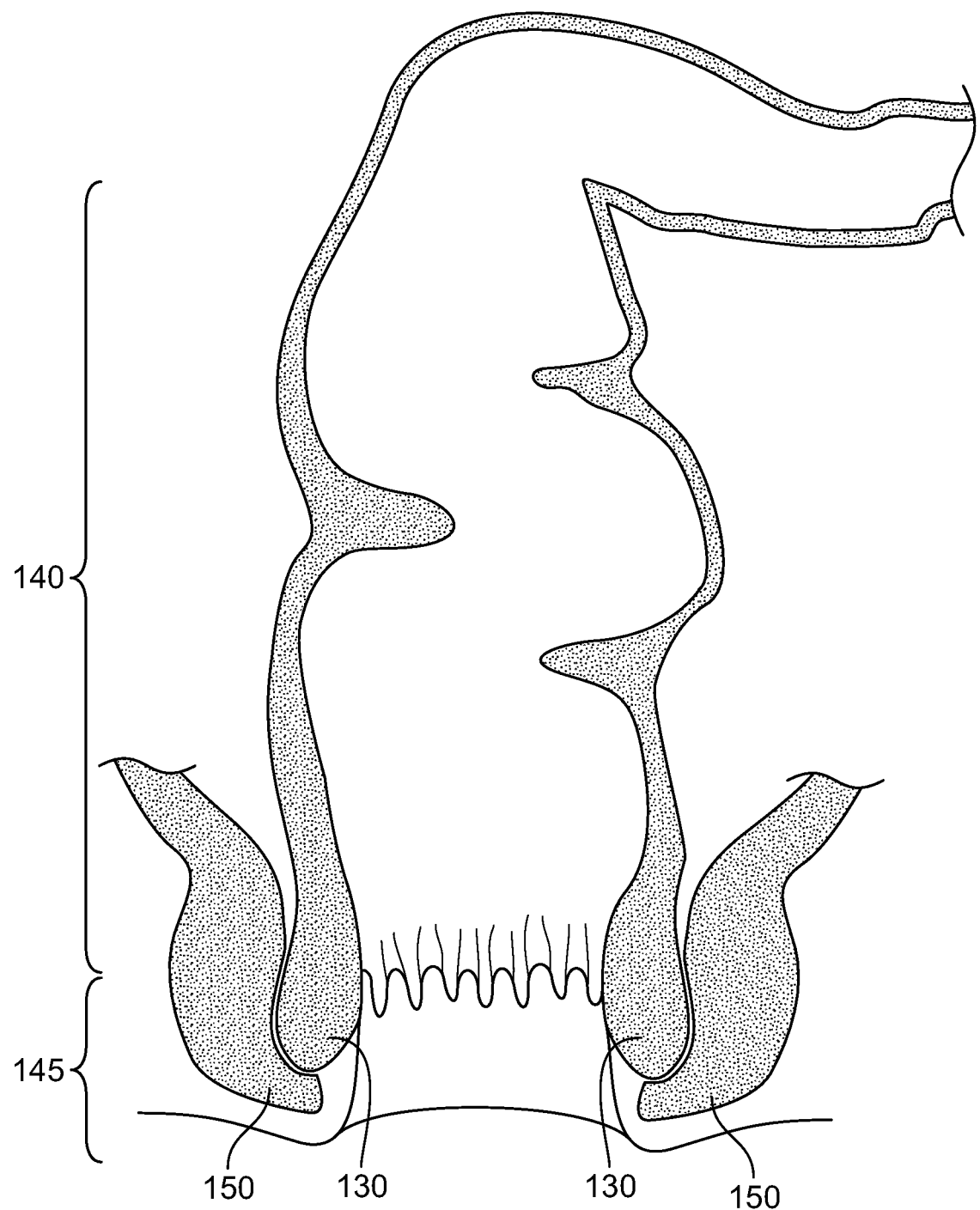
FIG. 1 is a cross sectional illustration of the rectum and anal canal.

The present specification is directed toward programmable, implantable electro-medical devices for the treatment of various anorectal or genitourinary neuromuscular disorders, including fecal incontinence, constipation, urinary incontinence, and sexual dysfunction. The electro-medical devices of the present specification employ implantable microstimulators or macrostimulator that can be implanted with minimal invasiveness in the anorectal region and/or genitourinary region. In one embodiment, each microstimulator includes at least two electrodes used to deliver electrical stimulation to at least two separate target tissues. In one embodiment, the electro-medical device comprises a common anode or cathode in the middle and two separate electrodes, each with polarity opposite to the center electrode, at each end. In another embodiment the device has only two electrodes where the stimulating electrode is selected based on the desired region to be stimulated. In various embodiments, the electro-medical device is implanted into the mucosa, submucosa, or muscularis propria of the anorectal region and/or genitourinary region. Preferably, the electro-medical device is implanted into the rectal submucosa and/or genitourinary submucosa. The rectal submucosa and genitourinary submucosa are low impedance layers. The rectal submucosa is easily accessible, with implantation involving minimal risk and invasiveness. After implantation of the electro-medical device, the electrodes are endoscopically or surgically routed to each specific target tissue. In various embodiments, the electrodes are designed utilizing technology such as shape memory to allow for appropriate configurations. Differential length, shape or configuration of the electrodes will make them better suited to be positioned proximate the desired target tissue. A first electrode is implanted within or proximate a first target tissue and a second electrode is implanted within or proximate a second target tissue. In one embodiment, the target tissues comprise muscles and nerves in the anorectal region. In another embodiment, the target tissues comprise muscles and nerves in the genitourinary region. In various embodiments, the target tissues comprise the longitudinal muscle of the rectum, the circular muscle of the rectum, the muscularis mucosa of the rectum, the submucosa of the rectum, the pudendal nerve or a branch of the pudendal nerve, a conjoined longitudinal muscle, the superficial or deep parts of the external anal sphincter, the internal anal sphincter, the muscularis mucosa of the anal canal, the subserosal plexus, the longitudinal intramuscular plexus, the circular intramuscular plexus, the periglandular plexus, the myenteric (Auerbach's) plexus, or the submucosal (Meissner's) plexus of the anorectum. The subcutaneous portion of the external anal sphincter lies proximate to the skin and has nerve innervation overlapping with the overlying skin and hence it's desirable that stimulation of the subcutaneous part of the external anal sphincter is minimized or avoided to minimize sensation associated with stimulation.

The present specification is also directed toward a system and method of stimulating two separate anorectal or genitourinary tissues for the treatment of various anorectal or genitourinary neuromuscular disorders, including fecal incontinence, constipation, urinary incontinence, and sexual dysfunction. In various embodiments, the two target tissues are selectively stimulated simultaneously or at separate times using the same or different stimulation algorithms.

For example, in one embodiment, a first electrode is implanted in the internal anal sphincter and a second electrode is implanted in the external anal sphincter. The internal anal sphincter is provided with a first level of stimulation which is applied continuously. Meanwhile, the external anal sphincter is provided with a second level of stimulation which is applied on demand. Stimulating multiple target tissues with the same or different stimulation algorithms improves anorectal function and increases energy efficiency while avoiding fatigue and tolerance issues that is encountered in the prior art. Additionally, fewer devices and electrodes are required as separate target structures can receive different stimulation via different algorithms rather than from different electrodes and devices. For example a 200 uSec pulse maybe better suited to stimulate the internal anal sphincter while a 3 mSec or 300 mSec pulse maybe better suited to stimulate the external anal sphincter. Hence, by providing these difference pulses through the same electrodes at different times could achieve a desired clinical effect of maintaining continence.

The present specification is also directed toward a catheter for implantation of the electro-medical device. In one embodiment, the catheter comprises a sheath and a pusher to which is attached the electro-medical device. The pusher has a sharp bend proximate its distal end. The pusher is extended past an opening at the distal end of the sheath, allowing the sharp bend to partially expand and exposing the electro-medical device. The pusher is then retracted back into the sheath, pushing the electro-medical device into the anorectal tissue. As the pusher is fully retracted into the sheath, the electro-medical device disengages from its distal end.

The present specification is also directed toward an insertion device for assisting in the delivery of the catheter and implantation of the electro-medical device. In one embodiment, the insertion device comprises a conical, distal portion and a cylindrical, proximal portion. In one embodiment, a moveable valve covers an opening at the distal end of the distal portion. The distal portion includes a slot for capturing a portion of anorectal tissue. A mechanism, such as a plunger, is slidably movable within the proximal portion and is used to create suction and draw a portion of anorectal tissue in through the slot and into the distal portion. Alternatively, external suction using a pump could be applied to engage the anorectal tissue. The catheter, as described above, is then used to implant the electro-medical device.

The devices can be also placed using standard endoscopic, laparoscopic, stereotactic or other medical techniques known in the art.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Figure 2:
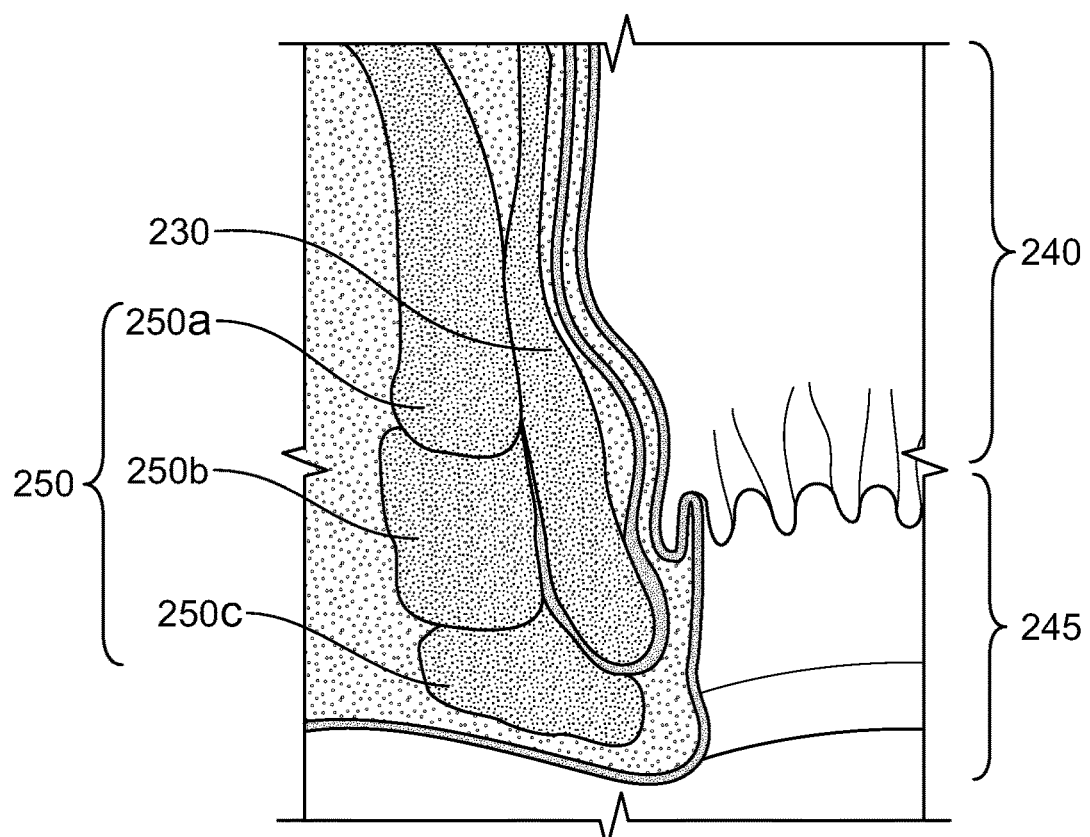
FIG. 2 is a cross sectional illustration of the musculature of one side of the lower rectum and anal canal.
Figure 3A:
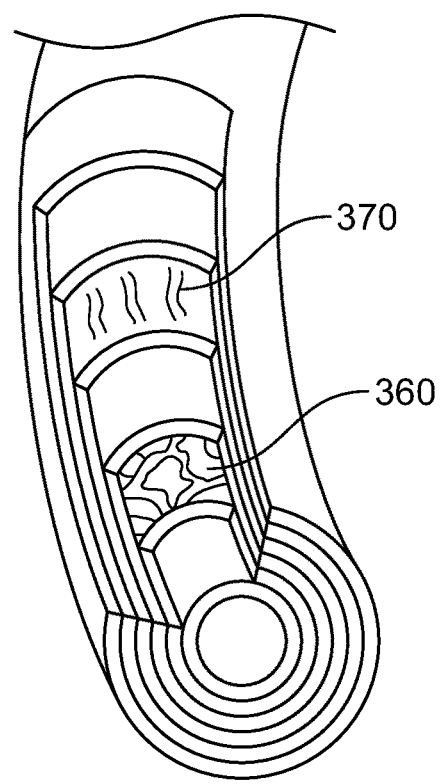
FIG. 3A is a cut away illustration of the lower colon, depicting nerve plexuses in the wall of the rectum and anal canal.

Persons of ordinary skill in the art would appreciate that normal anorectal function, including continence, is a complex mechanism that requires both involuntary (subconscious) and voluntary (conscious) control of the anal sphincter musculature. FIG. 1 is a cross sectional illustration of the rectum 140 and anal canal 145. FIG. 2 is a cross sectional illustration of the musculature of one side of the lower rectum 240 and anal canal 245. FIG. 3A is a cut away illustration of the lower colon, depicting nerve plexuses 360, 370 in the wall of the rectum and anal canal. Referring now to FIGS. 1 through 3 simultaneously, the internal anal sphincter 130, 230 is a smooth muscle under involuntary control, is innervated by the submucosal (Meissner's) nerve plexus 360 and myenteric (Auerbach's) nerve plexus 370 in the intestinal wall, and is responsible for the resting tone of the sphincter. The external anal sphincter 150, 250 is a skeletal muscle under voluntary control, is innervated by the perineal branch of the fourth sacral nerve and the inferior rectal nerve, and is responsible for the squeeze pressure and voluntary tone of the sphincter. The external anal sphincter is further divided into deep 250a, superficial 250b and subcutaneous 250c component. Due to its smooth muscle composition, the internal anal sphincter 130, 230 is less prone to fatigue and can generate low levels of pressures for prolonged durations. On the other hand, the external anal sphincter 150, 250 is a skeletal muscle and hence can generate high voluntary pressures for short durations. However, it easily fatigues within minutes and cannot maintain a sustained high tone.

The electro-stimulation treatment methods of the present specification appreciate that the internal and external anal sphincter muscles are histologically and functionally distinct and require differential stimulation for optimal function. The internal anal sphincter requires prolonged stimulation to maintain the basal tone and prevent seepage of stool and mucus from the anus. Since normal defecation can be achieved even in the presence of continuous internal sphincter stimulation, sensing for defecation and inhibition of internal anal sphincter stimulation is unnecessary. The external anal sphincter requires short bursts of stimulation to generate squeeze pressure to overcome the urge to defecate. The present specification addresses the issue that continuous or prolonged stimulation of the external anal sphincter will lead to fatigue and pain by providing different stimulation algorithms to each target tissue.

Submucosal space is a low impedance space comprising loose connective tissues and the submucosal (Meissner's) nerve plexus 360. Therefore, in accordance with an aspect of the present specification, submucosal space is identified to be easily accessible for safe implantation of a microdevice and also for stimulation with more energy efficient algorithms.

Figure 3B:
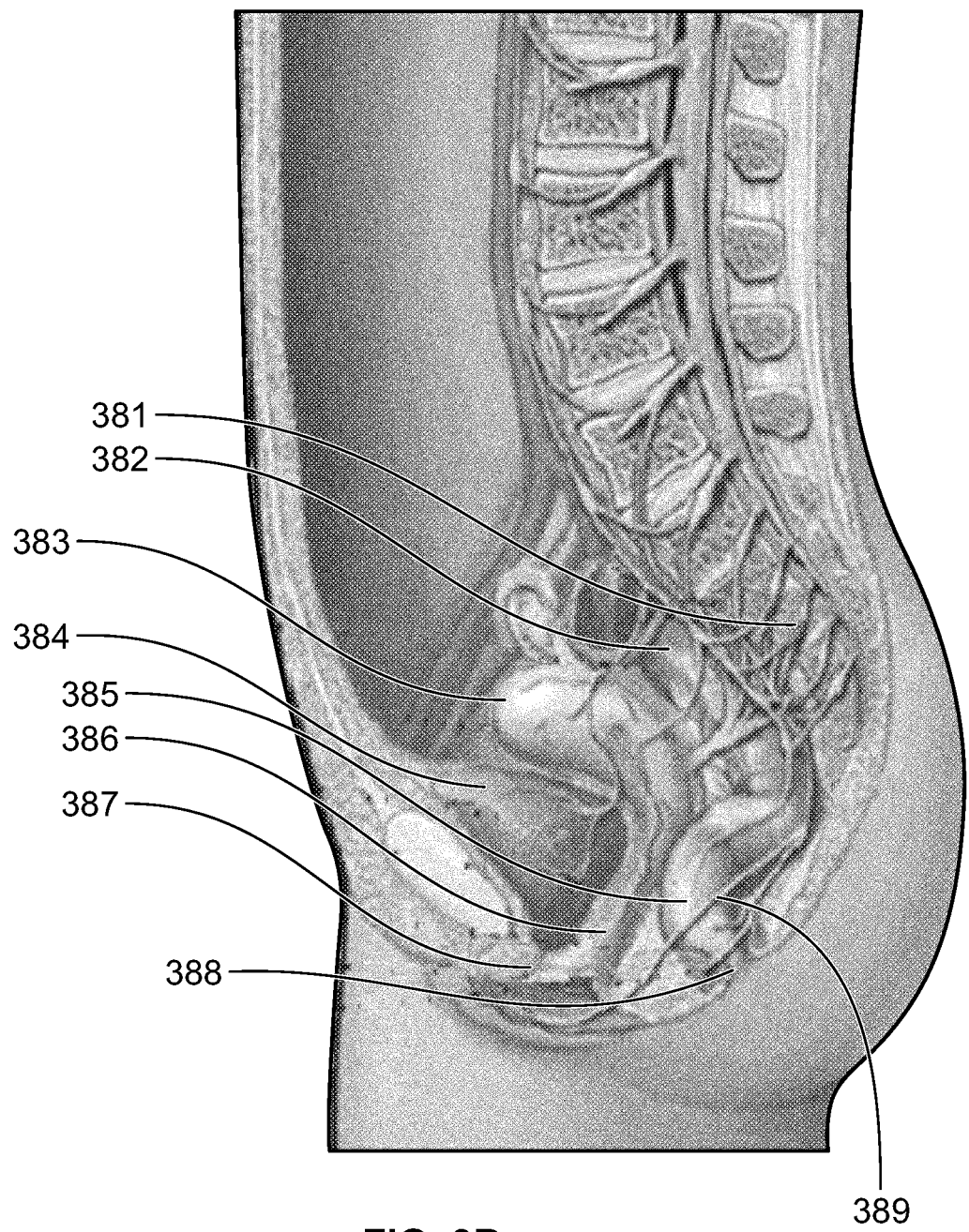
FIG. 3B is a cross sectional illustration of the viscera and innervation of the female lower abdomen and pelvis.
Figure 3D:
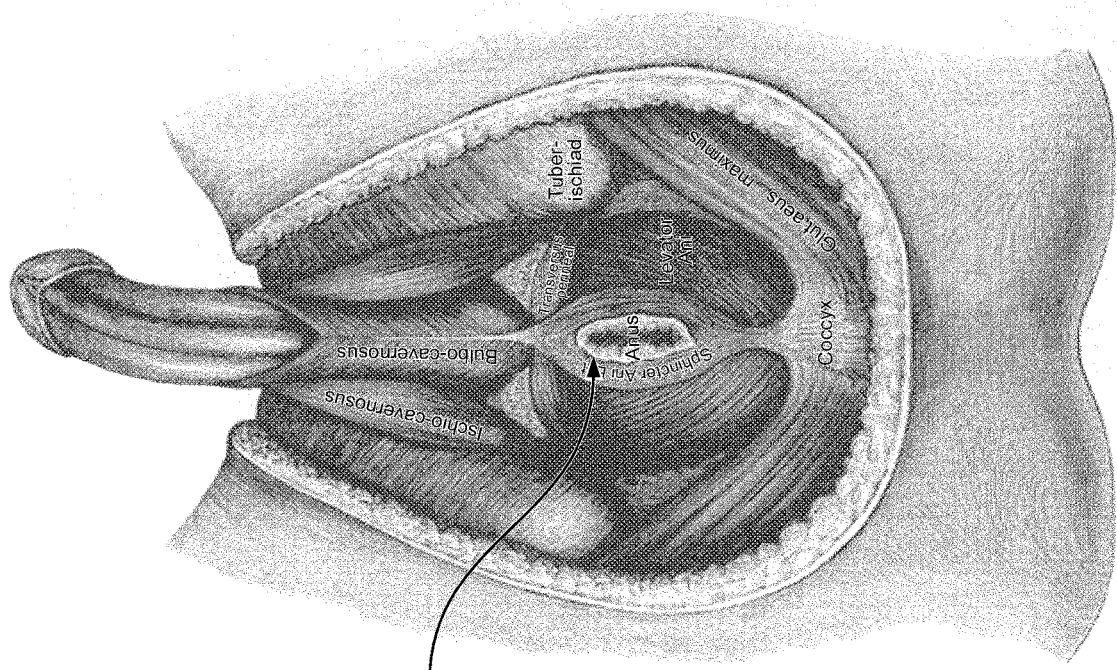
FIG. 3D is an illustration of the male perineal body.
Figure 3C:
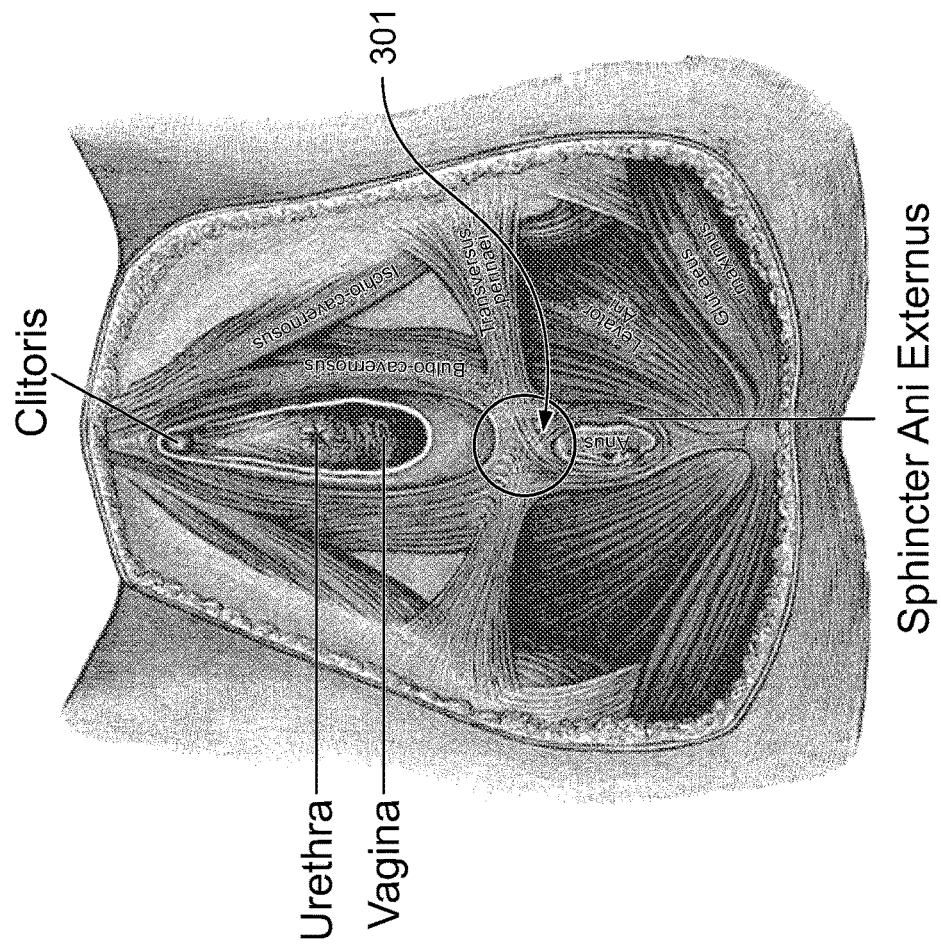
FIG. 3C is an illustration of the female perineal body.
Figure 3E:
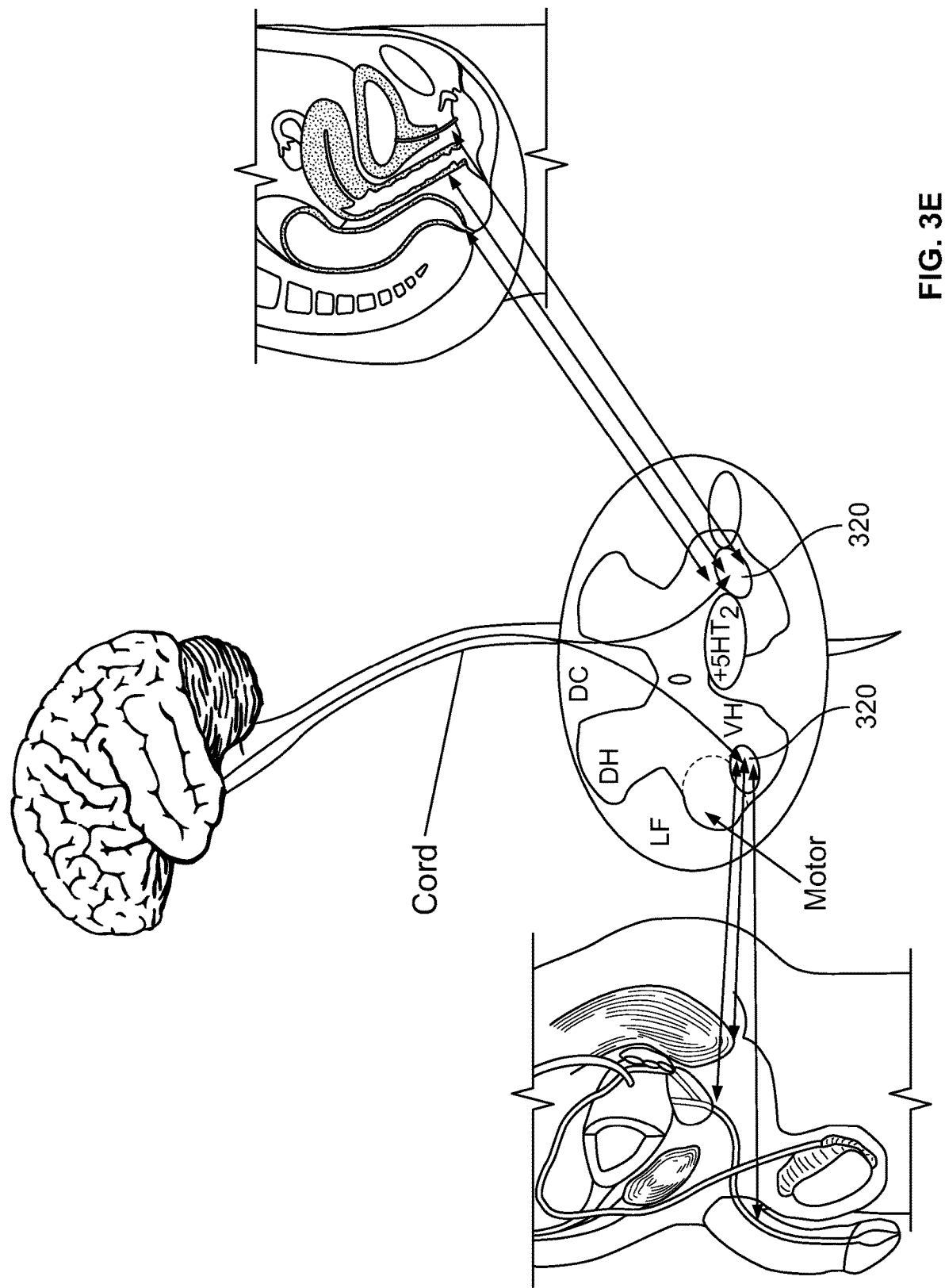
FIG. 3E is a first illustration of the pathways of motor control of the genitourinary system, depicting Onuf's nucleus in the spinal column.
Figure 3F:
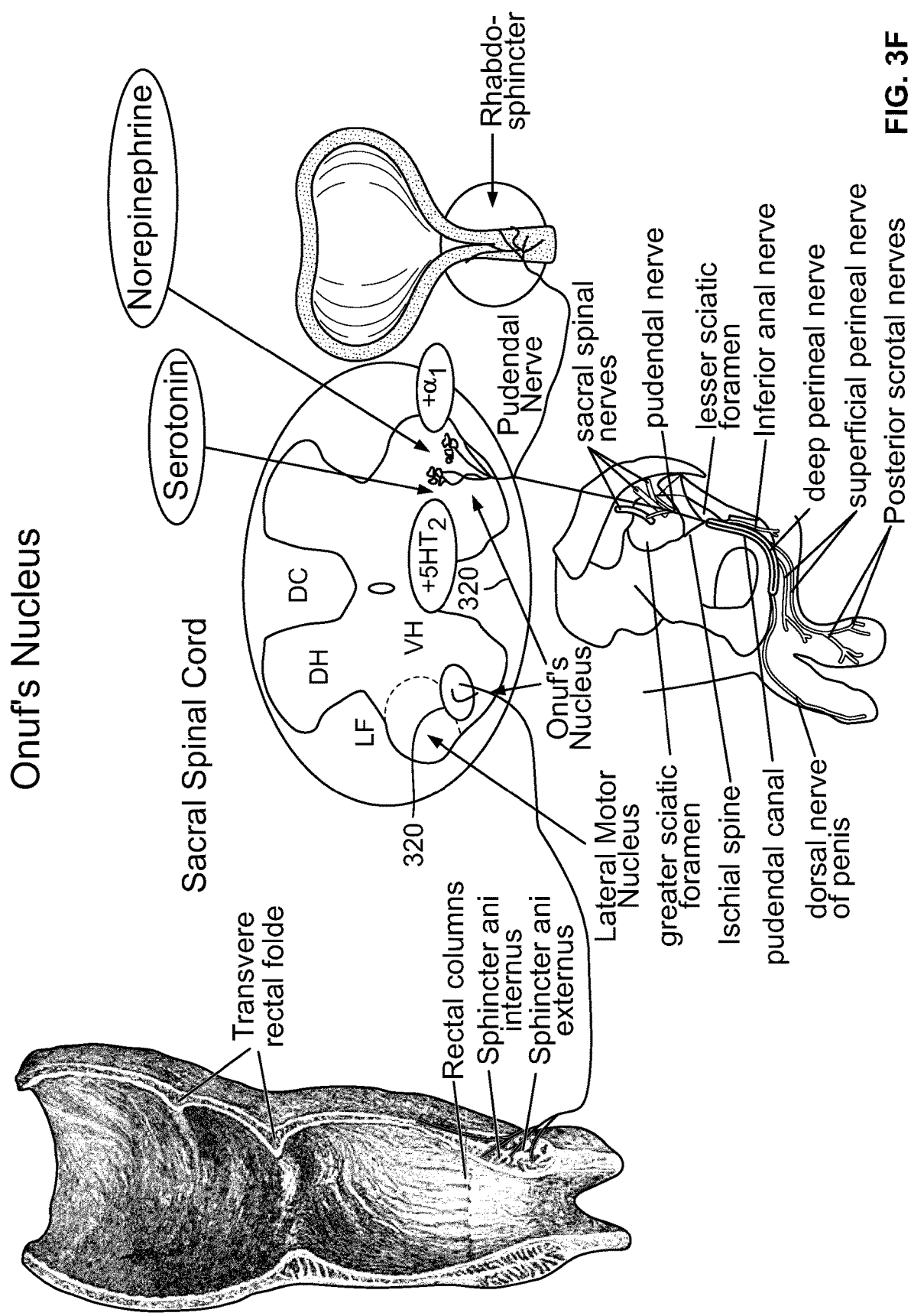
FIG. 3F is a second illustration of the pathways of motor control of the genitourinary system, depicting Onuf's nucleus in the spinal column.
Figure 3G:
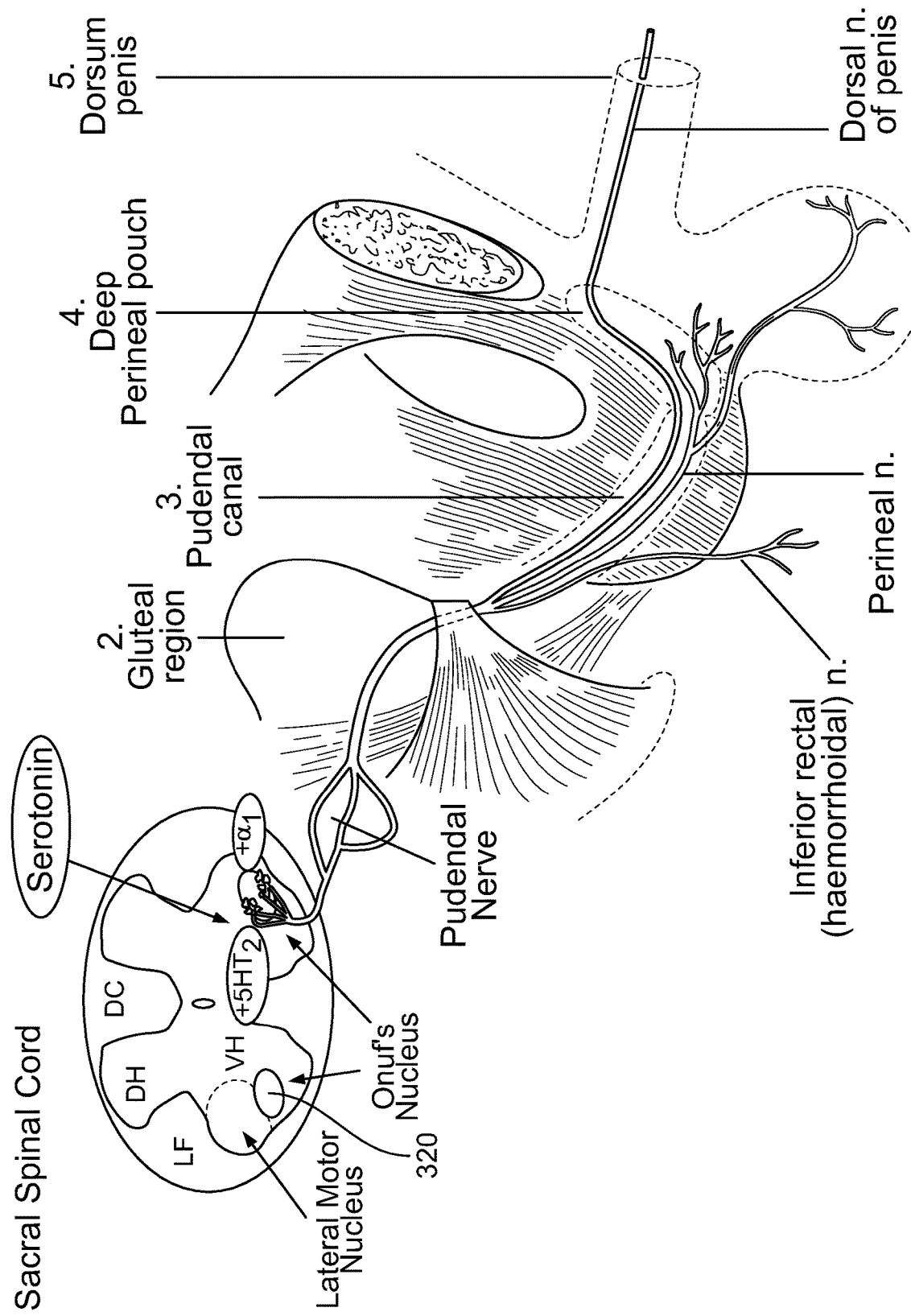
FIG. 3G is a third illustration of the pathways of motor control of the genitourinary system, depicting Onuf's nucleus in the spinal column.
Figure 3H:
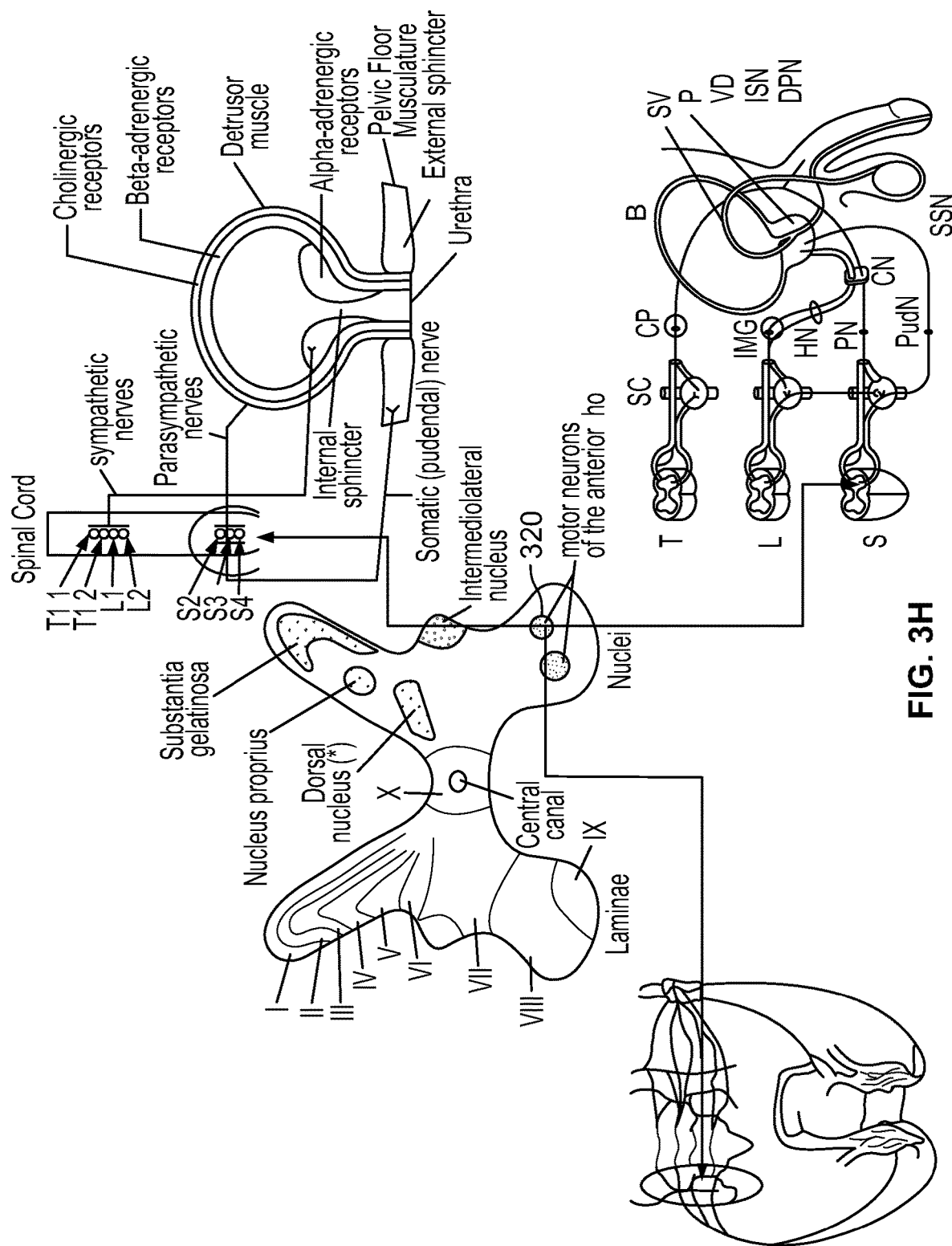
FIG. 3H is a fourth illustration of the pathways of motor control of the genitourinary system, depicting Onuf's nucleus in the spinal column.

FIG. 3B is a cross sectional illustration of the viscera and innervation of the female lower abdomen and pelvis, depicting the sacral nerves 381, colon 382, uterus 383, bladder 384, rectum 385, vagina 386, urethra 387, anus 388, and pudendal nerve 389. FIGS. 3C and 3D are illustrations of the female perineal body 301 and male perineal body 311, respectively. FIGS. 3E through 3H are illustrations of the pathways of motor control of the genitourinary system, depicting Onuf s nucleus 320 in the spinal column.

Figure 3I:
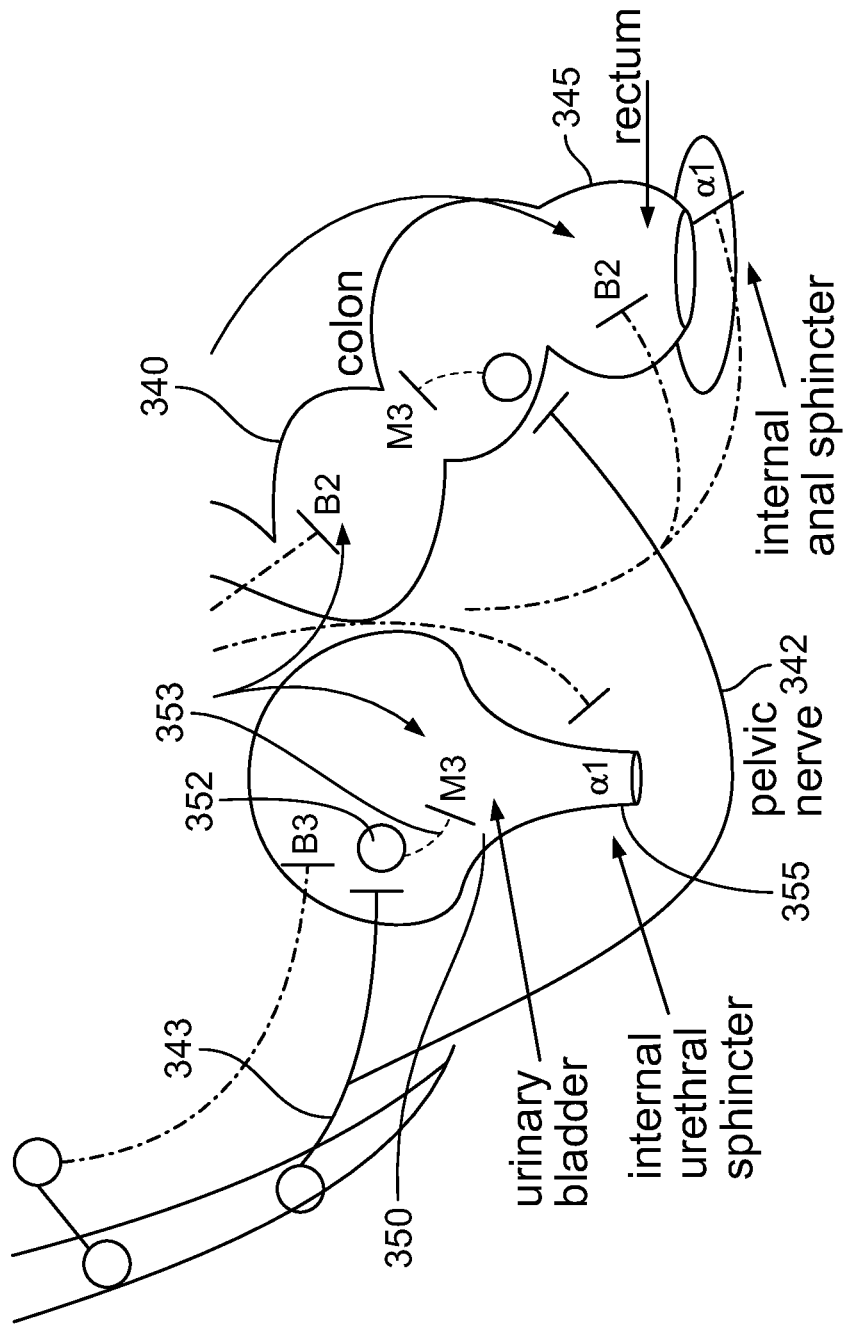
FIG. 3I is an illustration depicting the parasympathetic and sympathetic innervation of the colon, rectum, urinary bladder, and internal urethral sphincter.

FIG. 3I is an illustration depicting the parasympathetic and sympathetic innervation of the colon 340, rectum 345, urinary bladder 350, and internal urethral sphincter 355. The colon 340 and rectum 345 have parasympathetic innervation from the pelvic nerve 342. The postganglionic neurons are the enteric neurons of the myenteric plexus. The smooth muscle receptors are muscarinic 3 (M3) and activation by acetylcholine increases motility in these sections. Sympathetically, the colon 340 is innervated by neurons from the superior mesenteric ganglion while the rectum 345 is innervated by nerves originating in the inferior mesenteric ganglion. Norepinephrine is released from these to binds with beta 2 (B2) receptors on the smooth muscle layers to decrease their motility. Additionally, neurons from the inferior mesenteric also innervate the internal anal sphincter and release norepinephrine onto alpha 1 receptors causing increased tone in that tissue.

The preganglionic neurons 343 of the pelvic splanchnic nerves innervate the bladder 350 wall. They secrete acetylcholine onto the cell bodies of postganglionic neurons within intramural ganglia 352 in the wall. Postganglionic axons 353 release acetylcholine to activate muscarinic 3 receptors on smooth muscle cells. These cells respond by increasing their tone so that the bladder 350 is not as compliant to filling. Sympathetically, the bladder 350 wall musculature has beta 3 receptors that are innervated by postganglionic neurons from the hypogastric nerve arising from the ganglionic chain. Activated beta 3 receptors cause decreased muscle tone in the bladder 350 that facilitates filling.

The smooth muscle of the neck of the bladder, comprising the internal urethral sphincter 355, has alpha 1 receptors. Activation by norepinephrine from postganglionic neurons arising from the inferior mesenteric ganglion causes an increase in tone helping to maintain the urine in the expanding bladder 350.

Figure 4:
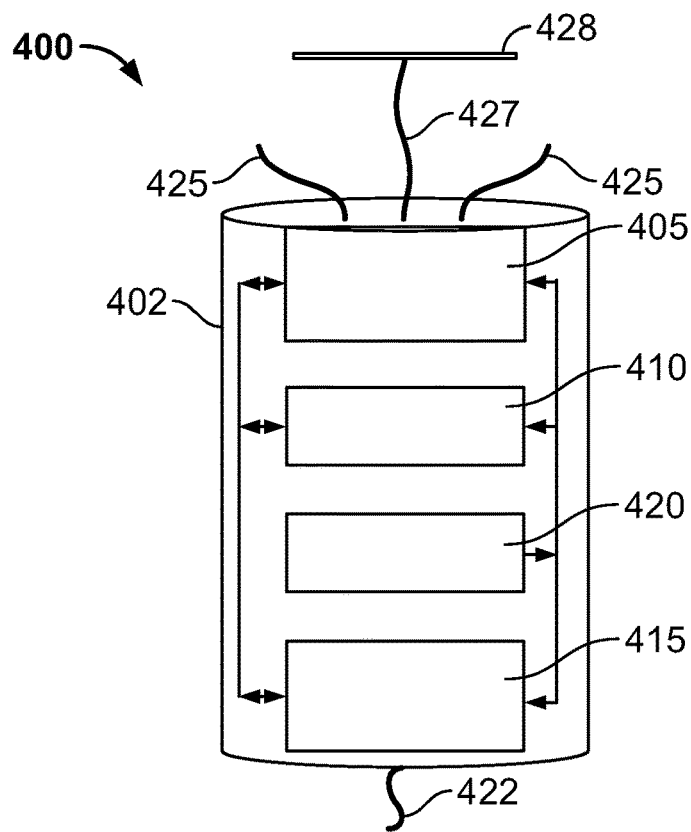
FIG. 4 is a schematic illustration of an exemplary programmable implantable electro-medical microdevice, in accordance with one embodiment of the present specification.

FIG. 4 is a schematic illustration of an exemplary programmable, implantable electro-medical microdevice 400, in accordance with one embodiment of the present invention. The microdevice 400 comprises a stimulator or waveform generator 405, a microcontroller 410, an optional sensor module 415 and a power source 420, all integrated into a single unit for easy and quick deployment within the anorectal region of a patient. The stimulator 405, microcontroller 410 and sensor module 415 are capable of communicating with each other using wired or wireless communication.

Referring to FIG. 4, the microdevice 400 comprises an outer shell 402 of a biocompatible, hermetically sealed material such as glass, ceramic, polymers, titanium, or any other suitable material evident to persons of ordinary skill in the art. In one embodiment, the microcontroller 410 comprises: a transceiver for receiving and transmitting data and/or power from outside the patient's body through inductive, radiofrequency (RF), electrical, magnetic, optical or other electromagnetic coupling; an integrated circuit (IC) chip for decoding and storing a plurality of stimulation parameters and generating a plurality of stimulation pulses; and, a programmable memory for storing sets of data, stimulation, and control parameters. Programmable memory allows for stimulation and control parameters to be adjusted for each individual patient by means of inductive, radiofrequency (RF), or other electromagnetic coupling, to settings that are safe, efficacious, and minimize discomfort.

The stimulator or waveform generator 405 is an electrophysiological stimulator capable of generating a plurality of desired electrical pulses for stimulating appropriate nerves and/or muscles in the anorectal region of the patient. The stimulator 405 generates a plurality of stimulus pulse trains as directed by the microcontroller 410. In one embodiment, the pulse trains are programmable and their characteristics can vary in the following ways: the number of pulses in a pulse train; the shape of pulses in a pulse train; the interval between pulse train repetitions; the duration of each pulse; the timing and amplitude of pulses in trains; and, the desired amount of amperage or potential to be provided, depending upon the condition and need of the patient. Further, the electrical stimulus may have any shape necessary to produce the desired result, including a square, rectangular, sinusoidal, or saw tooth shape. In one embodiment, the desired stimulus pulse is delivered through a plurality of stimulation electrodes 425.

In one embodiment, the stimulus is triggered by the patient using a transmitter external to the patient's body, similar to a remote transmitter for a cardiac pacemaker as known to persons of ordinary skill in the art.

In one embodiment, the power source includes an external power source coupled to the microdevice 400 via a suitable means, such as RF link. In another embodiment, the power source includes a self-contained power source 420 utilizing any suitable means of generation or storage of energy such as a primary battery, a replenishable or rechargeable battery such as a lithium ion battery, an electrolytic capacitor, etc.

In one embodiment, the optional sensor module 415 uses a plurality of sensing electrodes 422 to detect a plurality of physiological parameters such as pressure, electrical activity, and impedance. In another embodiment, the optional sensor module 415 includes an accelerometer to detect changes in patient position. In one embodiment, the optional sensor module 415 includes an inclinometer. The information gathered by the optional sensor module 415 is used to trigger stimulation and/or to modify on and off cycles of stimulation.

In one embodiment, the microdevice 400 also includes an anchor 428 that enables anchoring of the microdevice 400 to appropriate sites in the anorectal region of the patient. The anchoring element 428 is fixed to the microdevice 400 through an attachment 427. In one embodiment, the attachment 427 contracts after deployment, pulling the microdevice 400 deeper into the particular site or snug with the wall, thereby providing better retention.

In one embodiment, the plurality of stimulating electrodes 425 and sensing electrodes 422 are made up of a conducting ceramic, conducting polymer, and/or a noble or refractory metal. Persons of ordinary skill in the art should appreciate that, depending on the application, site, or desired physiological stimulus, an electrode can be used both as a sensing as well as a stimulation electrode. In various embodiments, the sensing electrode 422 and anchor 428 or the stimulating electrode 425 and anchor 428 may be the same element. In still other embodiments, the same element may be used as stimulating electrode 425, sensing electrode 422 and anchor 428.

In accordance with one embodiment of the method of treatment of the present specification, the stimulation pulses are delivered along the lines of the following parameters:
Frequency=0.02 Hz-100 Hz;
Amplitude=1 µAmp-100 mAmp;
Pulse width=1 msec-1 sec; and,
Duty cycle<100%

According to one embodiment, the treatment regimen comprises treating continuously with an on cycle of stimulation and an off cycle of stimulation. For example, the muscularis mucosa of the anal canal and the internal anal sphincter is treated continuously with an on cycle of stimulation and an off cycle of stimulation. In one embodiment, the on cycle of stimulation is 1 msec-23 hrs and the off cycle of stimulation is 1 msec-23 hrs.

Figure 5:
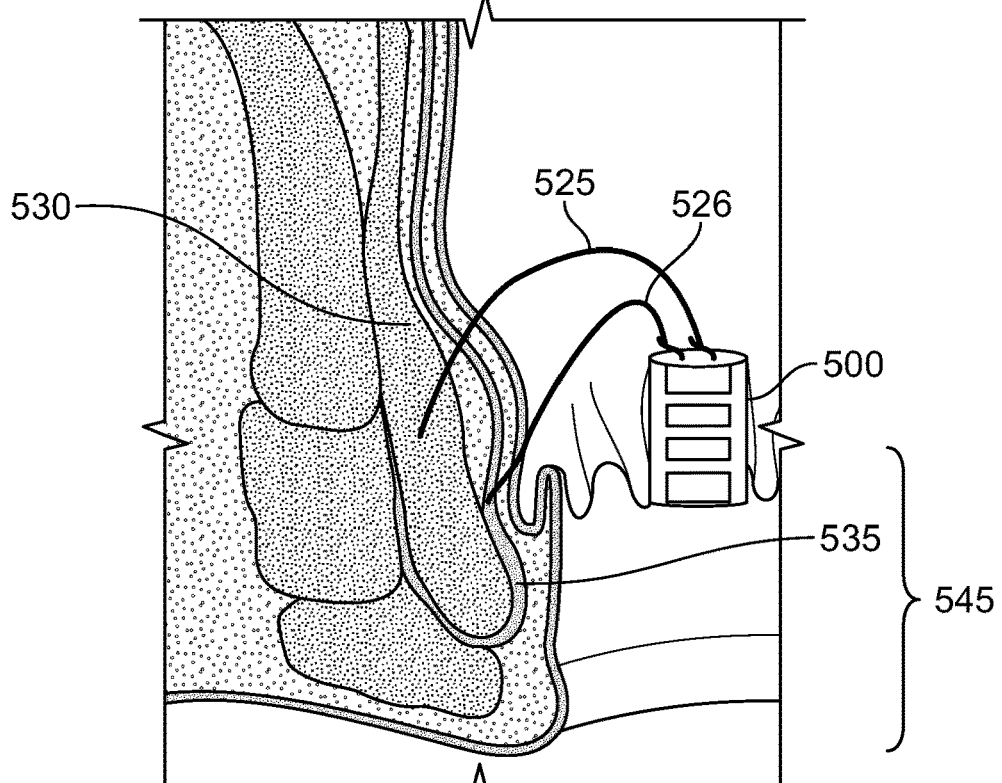
FIG. 5 is an illustration of one embodiment of an exemplary electrode set of a microdevice implanted in the internal anal sphincter and muscularis mucosa of the anal canal.

FIG. 5 is an illustration of one embodiment of an exemplary electrode set 525, 526 of a microdevice 500 implanted in the internal anal sphincter 530 and muscularis mucosa 535 of the anal canal. The microdevice 500 is implanted such that a first electrode 525 is proximate the internal anal sphincter 530 and a second electrode 526 is proximate the muscularis mucosa 535 of the anal canal 545.

Figure 6:
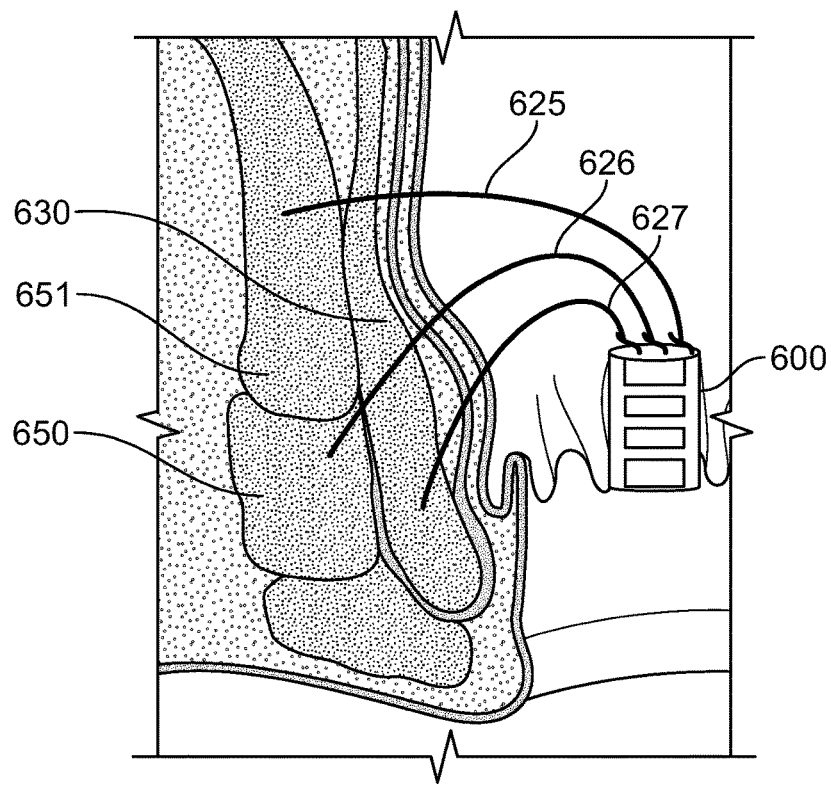
FIG. 6 is an illustration of one embodiment of an exemplary electrode set of a microdevice implanted in the superficial and deep part of the external anal sphincter and in the internal anal sphincter.

FIG. 6 is an illustration of one embodiment of an exemplary electrode set 625, 626 627 of a microdevice 600 implanted in the superficial 650 and deep 651 parts of the external anal sphincter and the internal anal sphincter muscle 630. The microdevice 600 is implanted such that two first electrodes 626, 625 are proximate the superficial part 650 and the deep part 651 of the external anal sphincter respectively, while a third electrode 627 is proximate the internal anal sphincter 630.

Figure 7:
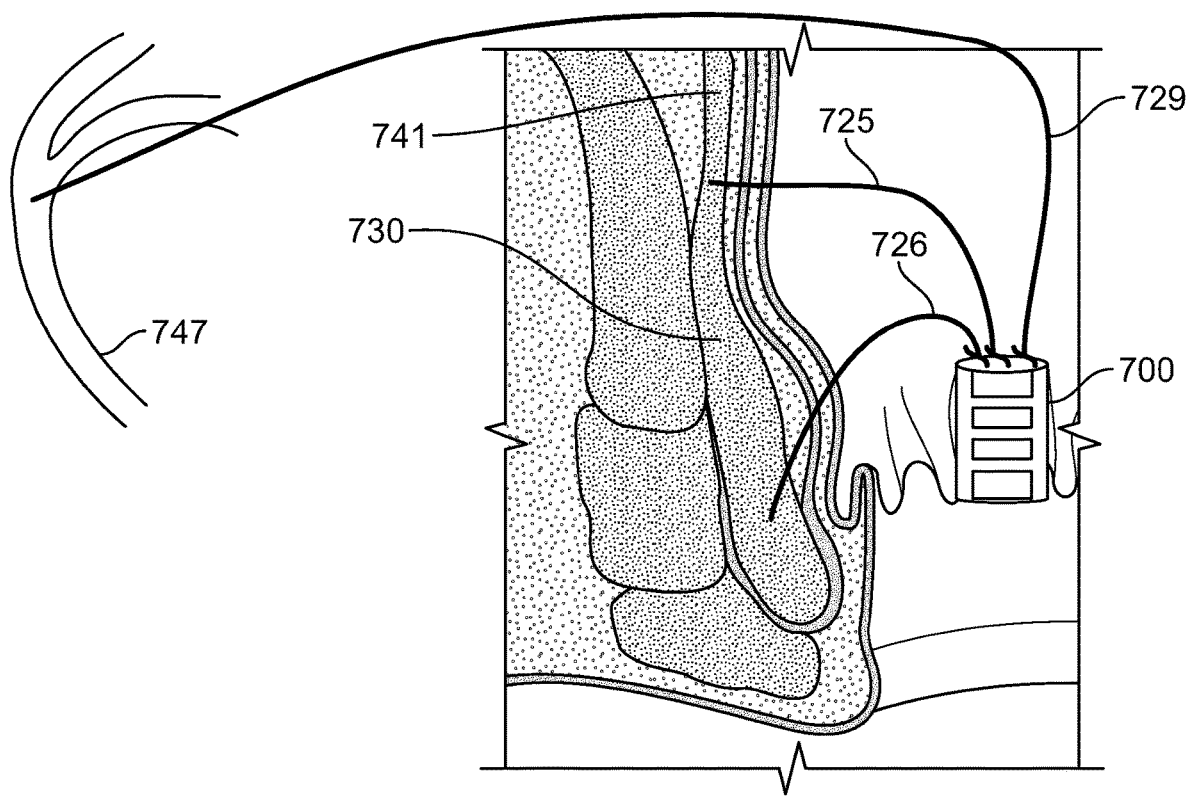
FIG. 7 is an illustration of one embodiment of an exemplary electrode set of a microdevice implanted in the circular muscle of the rectum, the internal anal sphincter, and proximate a branch of the pudendal nerve.

FIG. 7 is an illustration of one embodiment of an exemplary electrode set 725, 726, 729 of a microdevice 700 implanted in the circular muscle of the rectum 741, the internal anal sphincter muscle 730, and proximate a branch of the pudendal nerve 747. The microdevice 700 is implanted such that a first electrode 725 is proximate the circular muscle layer of the rectum 741 while a second electrode 726 is proximate the internal anal sphincter muscle 730. A third electrode 729 is placed proximate a branch of the pudendal nerve 747.

Figure 8:
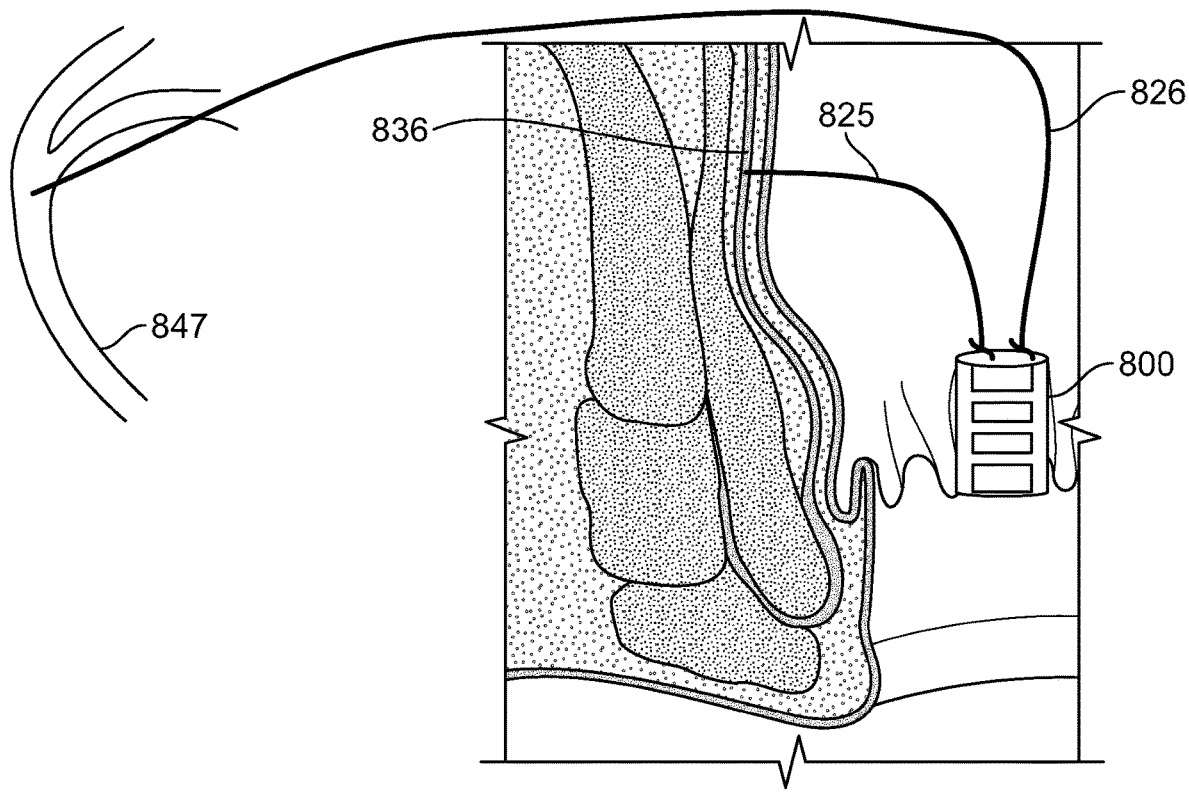
FIG. 8 is an illustration of one embodiment of an exemplary electrode set of a microdevice implanted in the submucosa of the rectum and in a branch of the pudendal nerve.

FIG. 8 is an illustration of one embodiment of an exemplary electrode set 825, 826 of a microdevice 800 implanted in the submucosa of the rectum 836 and in a branch of the pudendal nerve 847. The microdevice 800 is implanted such that a first electrode 825 is proximate the submucosa of the rectum 836 while a second electrode 826 is proximate a branch of the pudendal nerve 847.

Figure 9:
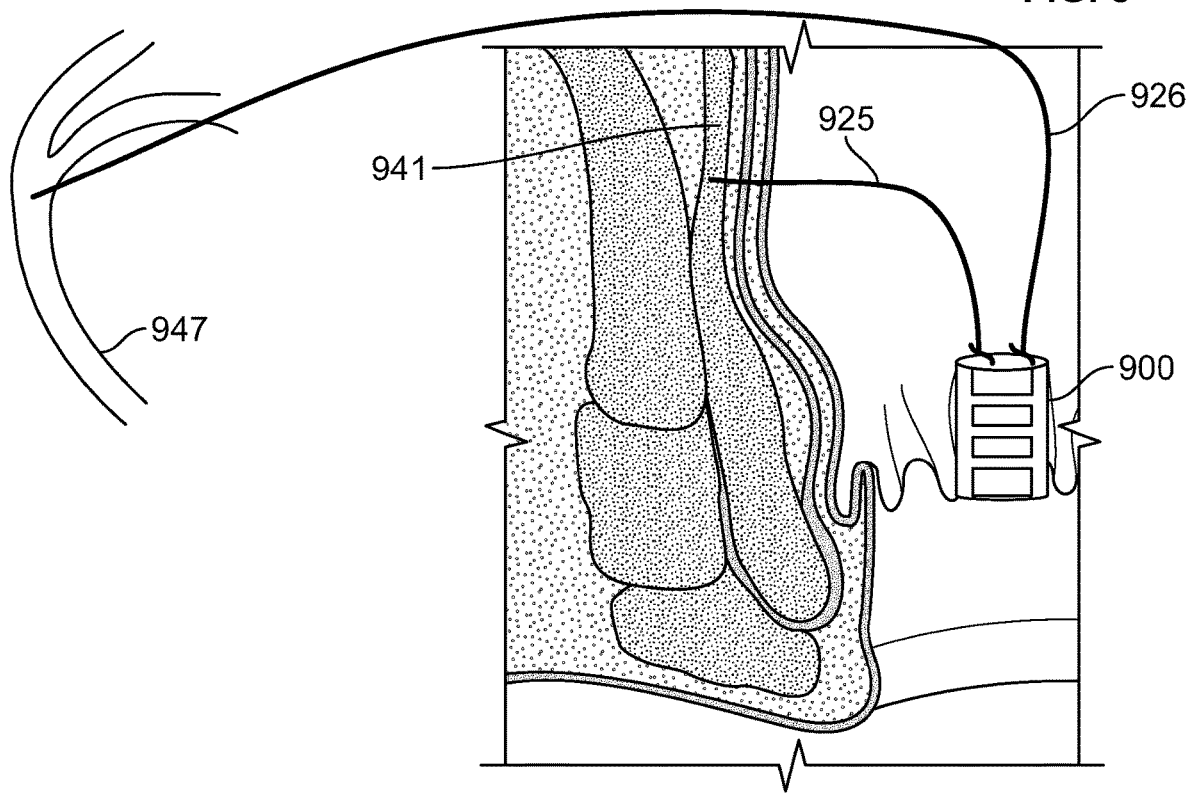
FIG. 9 is an illustration of one embodiment of an exemplary electrode set of a microdevice implanted in the circular muscle of the rectum and in a branch of the pudendal nerve.

FIG. 9 is an illustration of one embodiment of an exemplary electrode set 925, 926 of a microdevice 900 implanted in the circular muscle of the rectum 941 and in a branch of the pudendal nerve 947. The microdevice 900 is implanted such that a first electrode 925 is proximate the circular muscle layer of the rectum 941 while a second electrode 926 is proximate a branch of the pudendal nerve 947.

Figure 10:
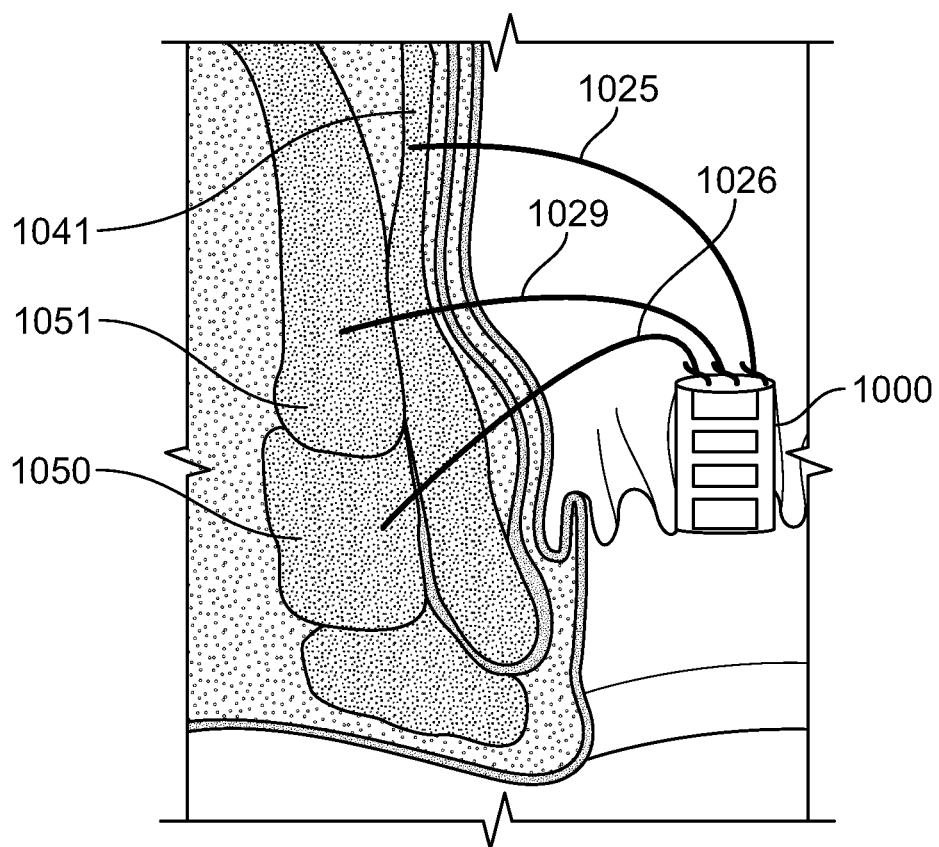
FIG. 10 is an illustration of one embodiment of an exemplary electrode set of a microdevice implanted in the circular muscle of the rectum and in the superficial and deep parts of the external anal sphincter.

FIG. 10 is an illustration of one embodiment of an exemplary electrode set 1025, 1026, 1029 of a microdevice 1000 implanted in the circular muscle of the rectum 1041 and in the superficial 1050 and deep 1051 parts of the external anal sphincter. The microdevice 1000 is implanted such that a first electrode 1025 is proximate the circular muscle layer of the rectum 1041 while a second electrode 1026 is proximate the superficial part of the external anal sphincter muscle 1050 and a third electrode 1029 is proximate the deep part of the external anal sphincter muscle 1051.

Figure 11A:
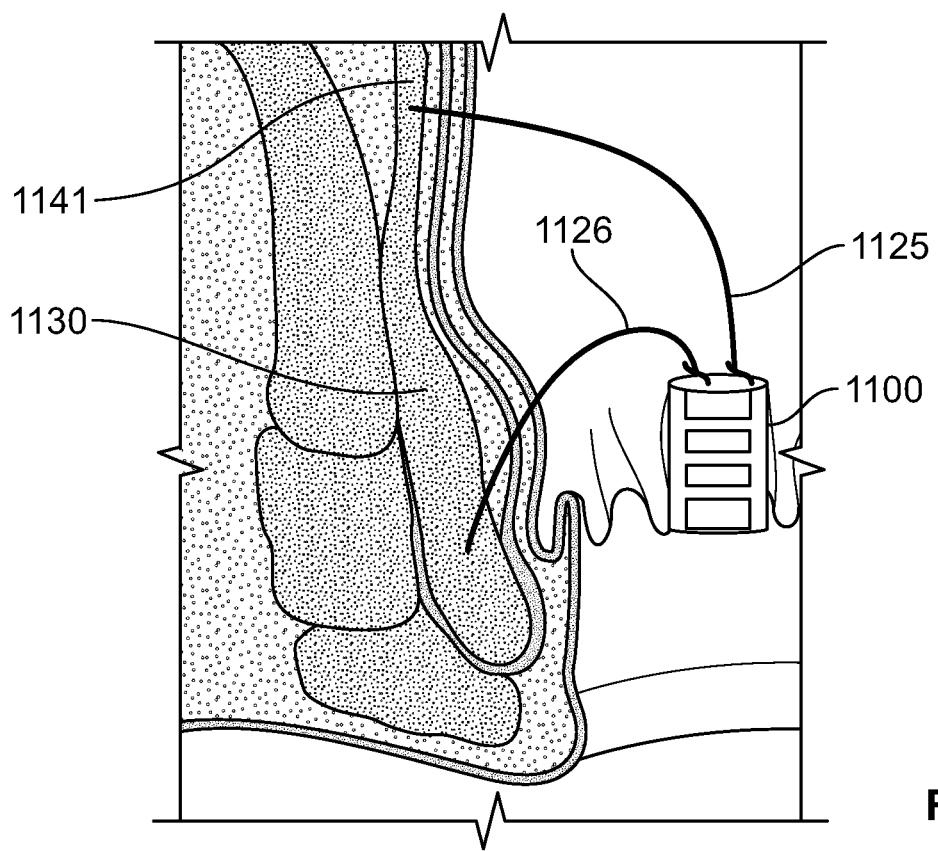
FIG. 11A is an illustration of one embodiment of an exemplary electrode set of a microdevice implanted in the circular muscle of the rectum and in the internal anal sphincter.

FIG. 11A is an illustration of one embodiment of an exemplary electrode set 1125, 1126 of a microdevice 1100 implanted in the circular muscle of the rectum 1141 and in the internal anal sphincter 1130. The microdevice 1100 is implanted such that a first electrode 1125 is proximate the circular muscle layer of the rectum 1141 and a second electrode 1126 is proximate the internal anal sphincter 1130.

Figure 11B:
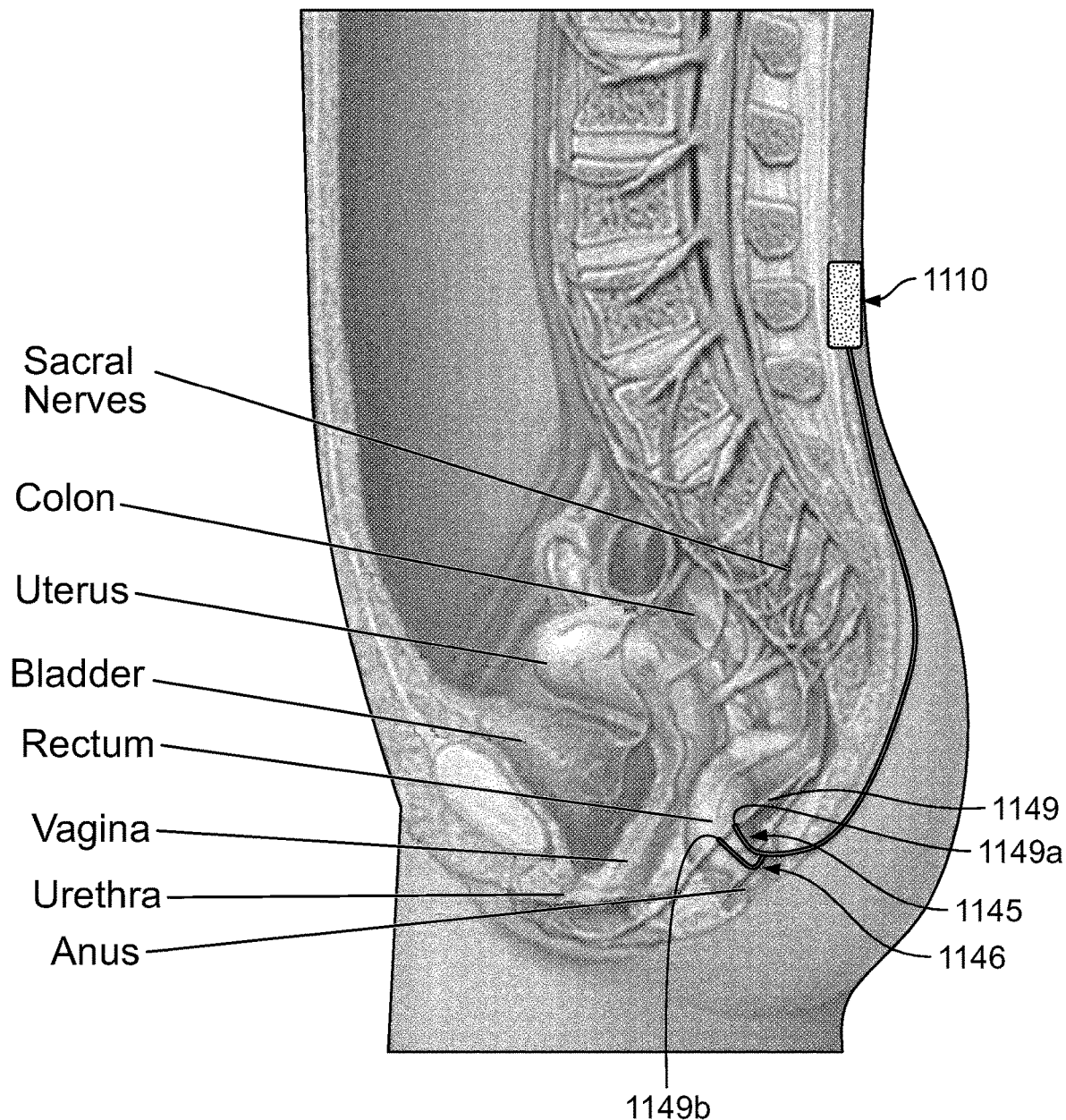
FIG. 11B is an illustration of one embodiment of an exemplary electrode set of a microdevice implanted in the back of a female patient, dorsal to the patient's spinal column.

FIG. 11B is an illustration of one embodiment of an exemplary electrode set 1145, 1146 of a microdevice 1110 implanted in the back of a female patient, dorsal to the patient's spinal column. The microdevice 1110 is implanted such that a first electrode 1145 is proximate a first portion 1149a of the pudendal nerve 1149 and a second electrode 1146 is proximate a second portion 1149b of the pudendal nerve 1149.

In various embodiments, the present specification discloses methods of treating urinary incontinence and/or fecal incontinence by implanting a stimulation device in the an abdominal, anorectal, or genitourinary region of a patient and providing electrical stimulation to at least one target tissue in any one or more of said anatomical regions, as described further below. In various embodiments, the stimulation device includes a controller and a stimulus generator in communication with said controller. At least one electrode is in electrical communication with the stimulus generator and configured to provide electrical stimulation to the at least one target tissue. The controller generates a stimulation signal, based on a programmed algorithm, that is transmitted to the stimulus generator. The generator, in response to that signal, generates an electrical stimulation pulse transmitted to the target tissue via the at least one electrode.

Figure 25:
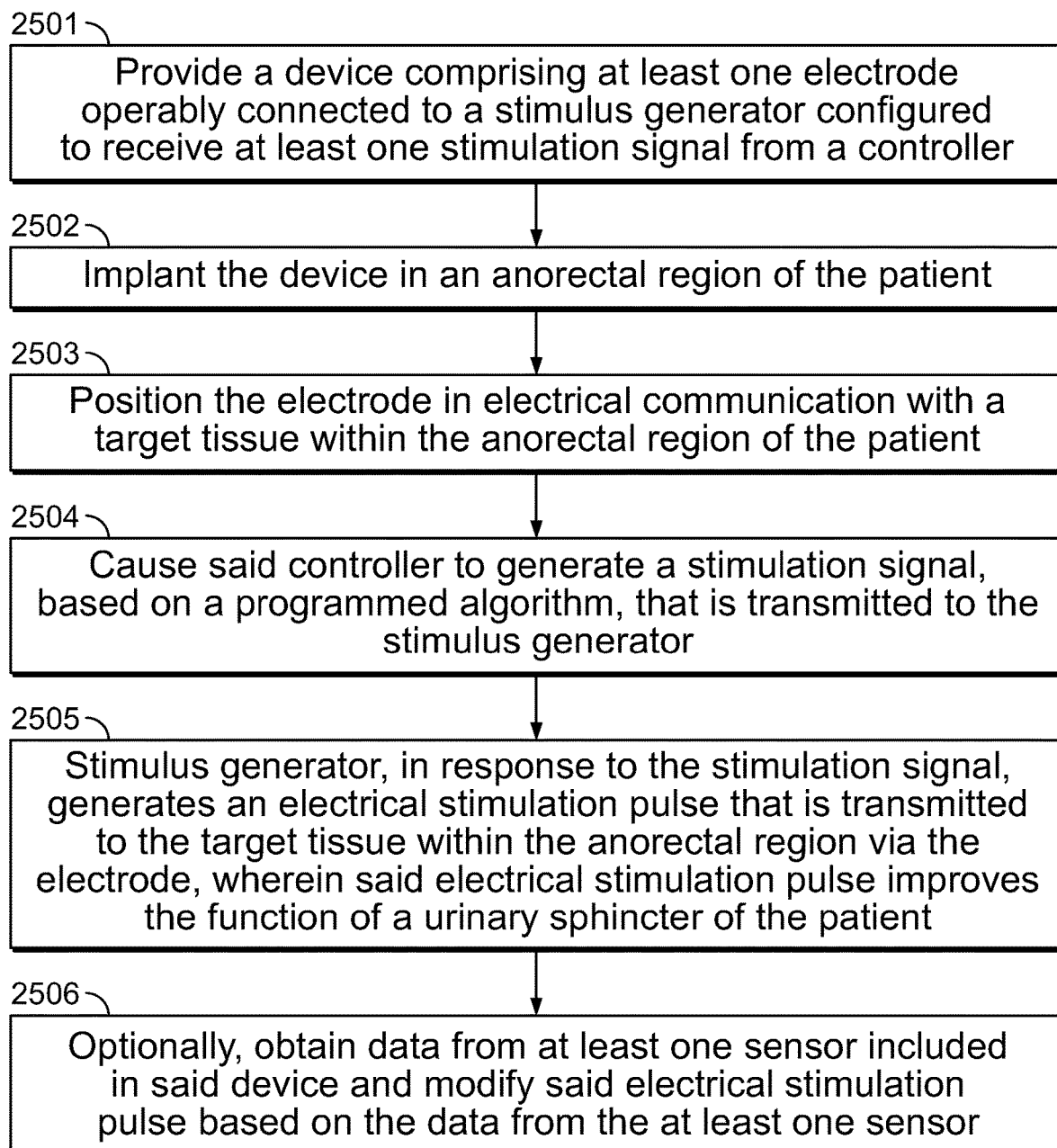
FIG. 25 is a flowchart illustrating a method of treating urinary dysfunction in a patient, according to an embodiment of the present specification.

In one embodiment, the present specification describes a method of treating urinary dysfunction in a patient. This method is shown in FIG. 25 and comprises the following steps: providing a device comprising at least one electrode operably connected to a stimulus generator configured to receive at least one stimulation signal from a controller in step 2501; implanting said device in an anorectal region of said patient in step 2502; positioning said electrode in electrical communication with a target tissue within said anorectal region of said patient in step 2503; and, causing said controller to generate a stimulation signal, based on a programmed algorithm, that is transmitted to the stimulus generator in step 2504. In step 2505, the stimulus generator, in response to the stimulation signal, generates an electrical stimulation pulse that is transmitted to said target tissue within said anorectal region via said electrode, wherein said electrical stimulation pulse improves the function of a urinary sphincter of said patient. Optionally, at step 2506, at least one sensor included on the device obtains data and the electrical stimulation pulse is modified based on the data from the at least one sensor. In various embodiments, said at least one sensor comprises a pressure sensor, an electrical activity sensor, an impedance sensor, an accelerometer, or an inclinometer.

In various embodiments, any of the devices disclosed in the present specification includes at least one sensor and any of the methods disclosed in the present specification optionally includes a step of obtaining data using said at least one sensor and modifying an electrical stimulation pulse based on the data obtained by said at least one sensor. In various embodiments, said at least one sensor comprises a pressure sensor, an electrical activity sensor, an impedance sensor, an accelerometer, or an inclinometer.

Figure 26:
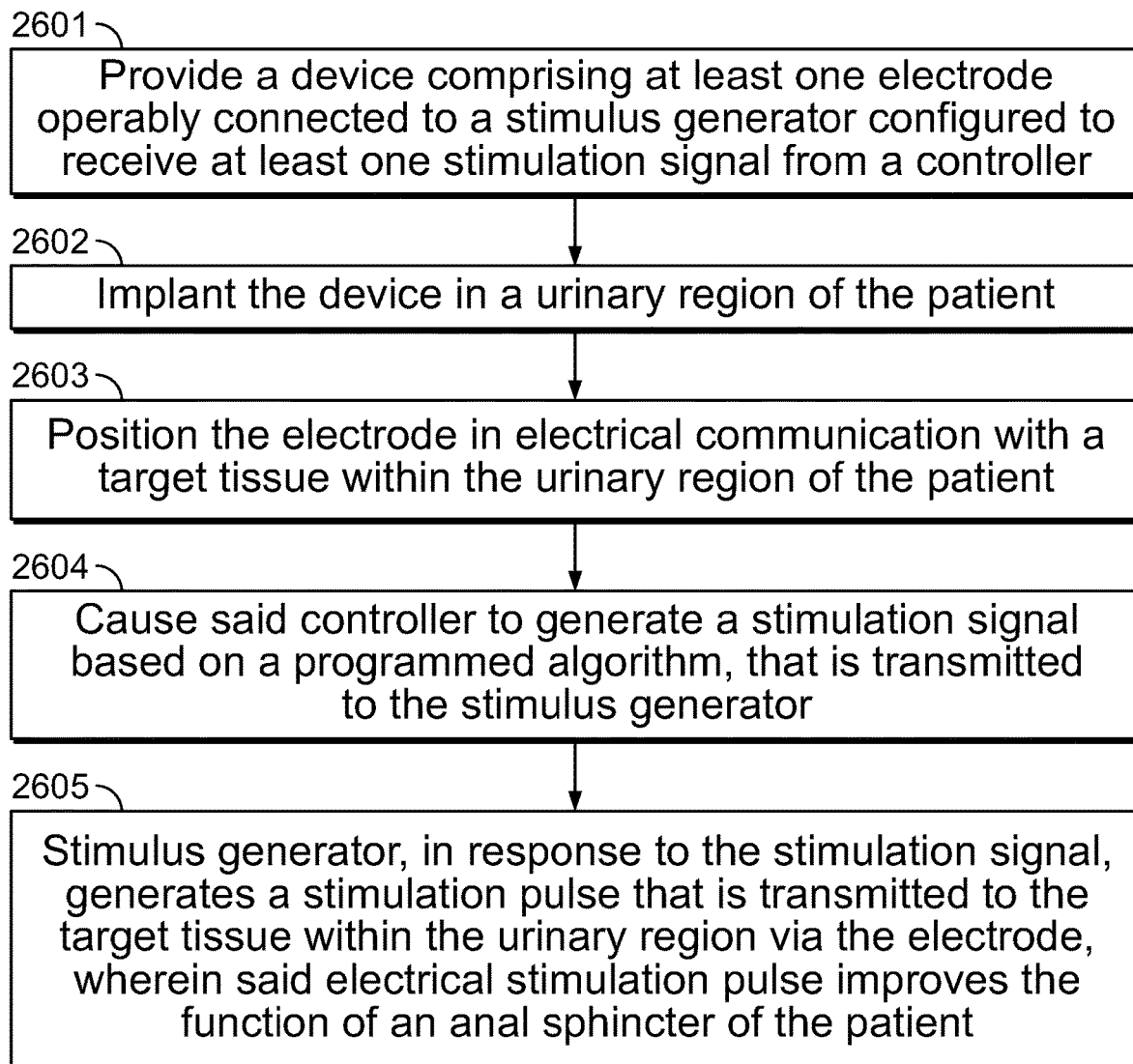
FIG. 26 is a flowchart illustrating a method of treating fecal dysfunction in a patient, according to an embodiment.

In another embodiment, the present specification describes a method of treating fecal dysfunction in a patient. This method is shown in FIG. 26 and comprises the following steps: providing a device comprising at least one electrode operably connected to a stimulus generator configured to receive at least one stimulation signal from a controller in step 2601; implanting said device in a urinary region of said patient in step 2602; positioning said electrode in electrical communication with a target tissue within said urinary region of said patient in step 2603; and, causing said controller to generate a stimulation signal based on a predetermined algorithm, that is transmitted to the stimulus generator in step 2604. In step 2605, the stimulus generator, in response to the stimulation signal, generates an electrical stimulation pulse that is transmitted to said target tissue within said urinary region via said electrode, wherein said electrical stimulation pulse improves the function of an anal sphincter of said patient.

Figure 27:
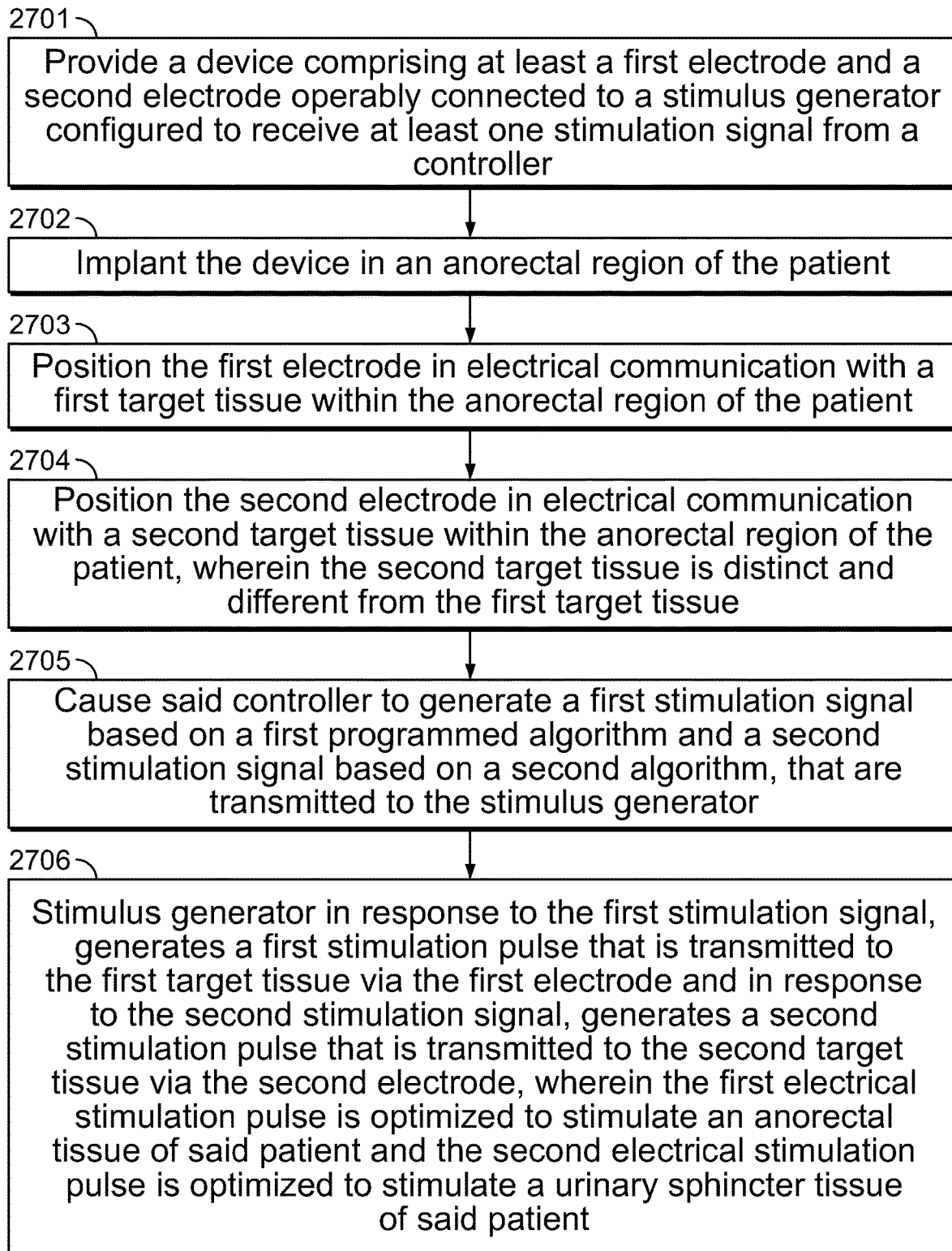
FIG. 27 is a flowchart illustrating a method of treating fecal dysfunction in a patient, according to another embodiment of the present specification.

In another embodiment, the present specification describes a method of treating fecal dysfunction in a patient. This method is shown in FIG. 27 and comprises the following steps: providing a device comprising at least a first electrode and a second electrode operably connected to a stimulus generator configured to receive at least one stimulation signal from a controller in step 2701; implanting said device in an anorectal region of said patient in step 2702; positioning said first electrode in electrical communication with a first target tissue within said anorectal region of said patient in step 2703; positioning said second electrode in electrical communication with a second target tissue within said anorectal region of the patient in step 2704, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 2705. In step 2706, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first electrical stimulation pulse is optimized to stimulate an anorectal tissue of said patient and said second electrical stimulation pulse is optimized to stimulate a urinary sphincter tissue of said patient.

Figure 28:
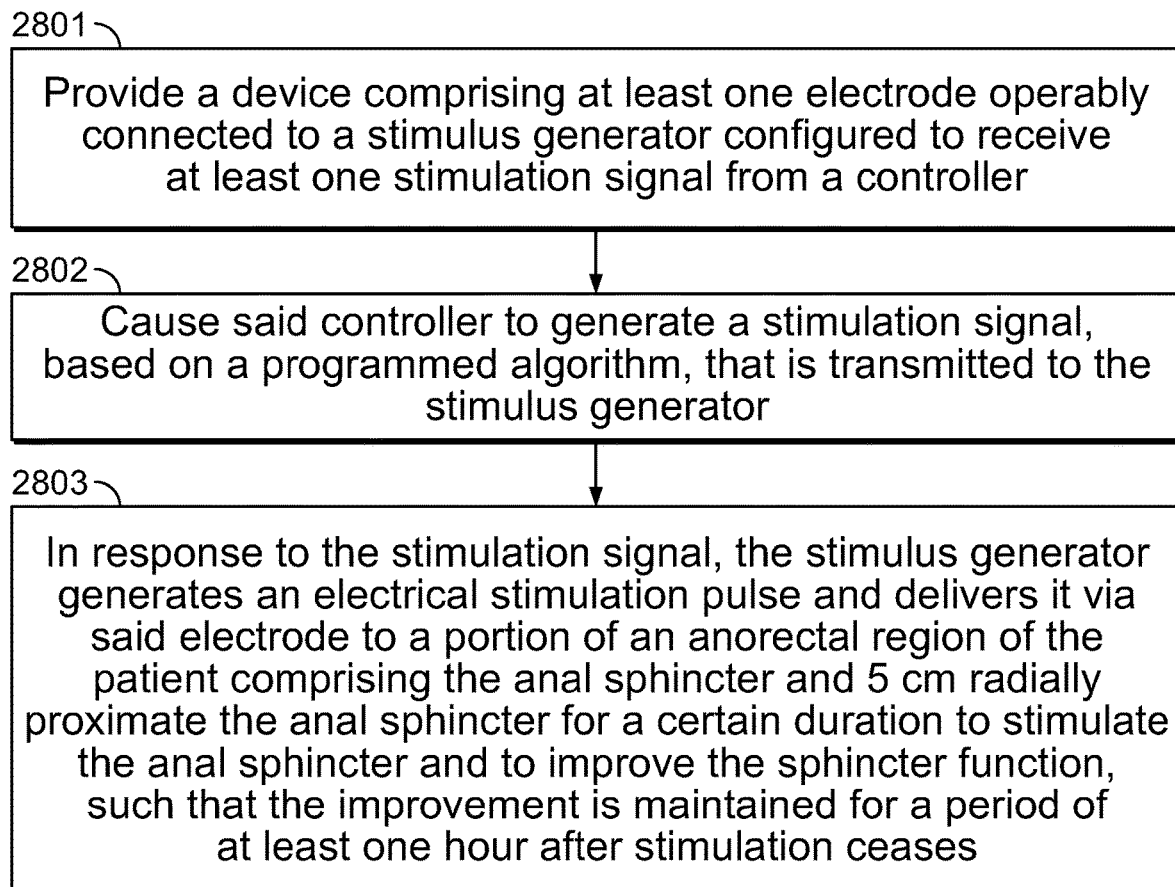
FIG. 28 is a flowchart illustrating a method of modulating anal sphincter function in a patient.

In another embodiment, the present specification describes a method of modulating anal sphincter function in a patient. This method is shown in FIG. 28 and comprises the following steps: providing a device comprising at least one electrode operably connected to a stimulus generator configured to receive at least one stimulation signal from a controller; and causing said controller to generate a stimulation signal, based on a programmed algorithm, that is transmitted to the stimulus generator in step 2802. In step 2803, in response to the stimulation signal, the stimulus generator generates an electrical stimulation pulse and delivers it via said at least one electrode to a portion of a region encompassing an anorectal region of the patient for a certain duration, wherein said region comprises the anal sphincter and 5 cm radially proximate the anal sphincter, to stimulate the anal sphincter and to improve the sphincter function, wherein said electrical stimulation pulse is adapted to cause said sphincter function improvement to be maintained for a period of at least one hour after stimulation ceases.

Figure 29:
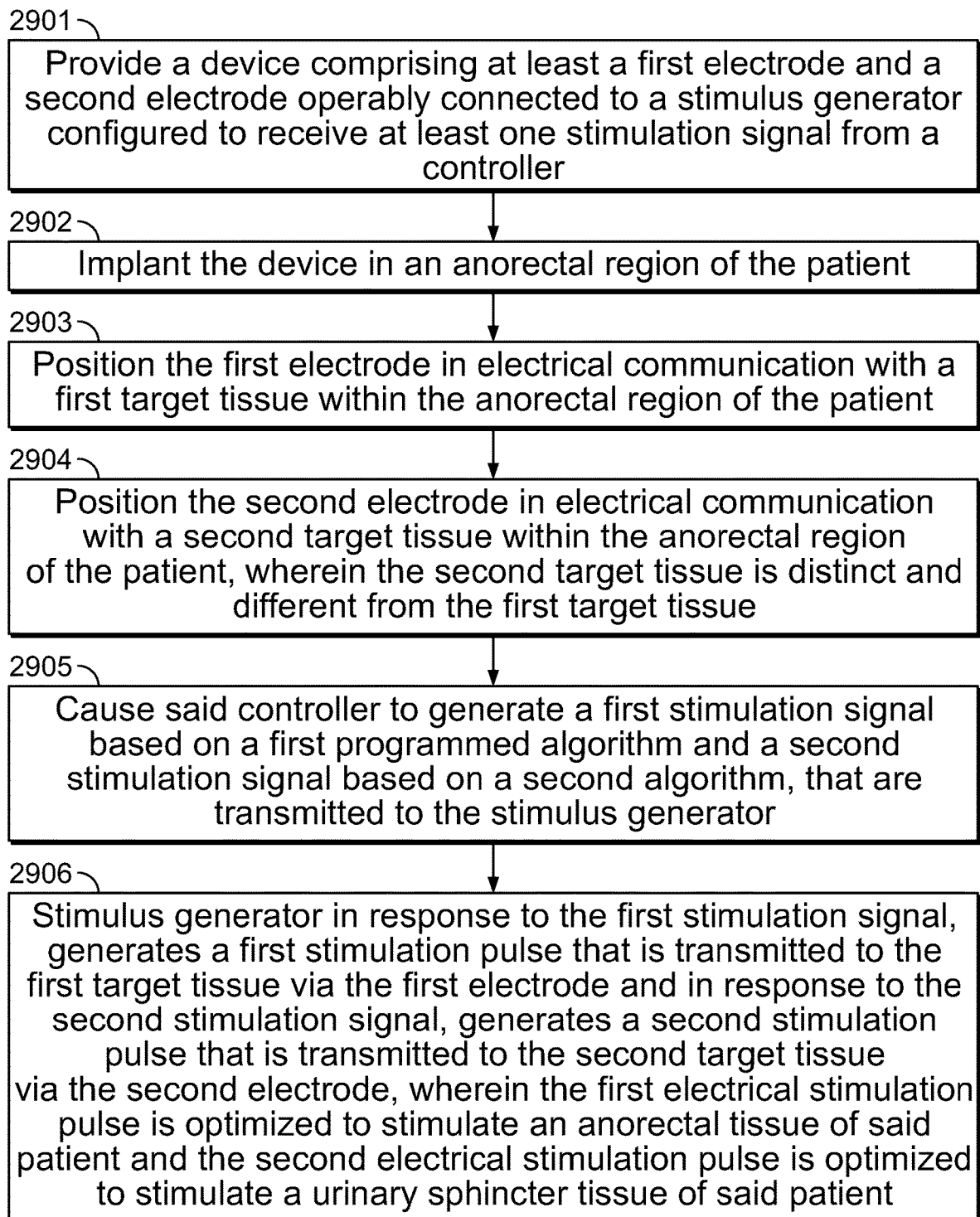
FIG. 29 is a flowchart illustrating a method of treating urinary dysfunction in a patient, according to another embodiment of the present specification.

In another embodiment, the present specification describes a method of treating urinary dysfunction in a patient. This method is shown in FIG. 29 and comprises the following steps: providing a device comprising at least a first electrode and a second electrode operably connected to a stimulus generator configured to receive at least one stimulation signal from a controller in step 2901; implanting said device in an anorectal region of said patient in step 2902; positioning said first electrode in electrical communication with a first target tissue within said anorectal region of said patient in step 2903; positioning said second electrode in electrical communication with a second target tissue within said anorectal region of said patient in step 2904, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 2905. In step 2906, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first electrical stimulation pulse is optimized to stimulate an anorectal tissue of said patient and said second electrical stimulation pulse is optimized to stimulate a urinary sphincter tissue of said patient.

Figure 30:
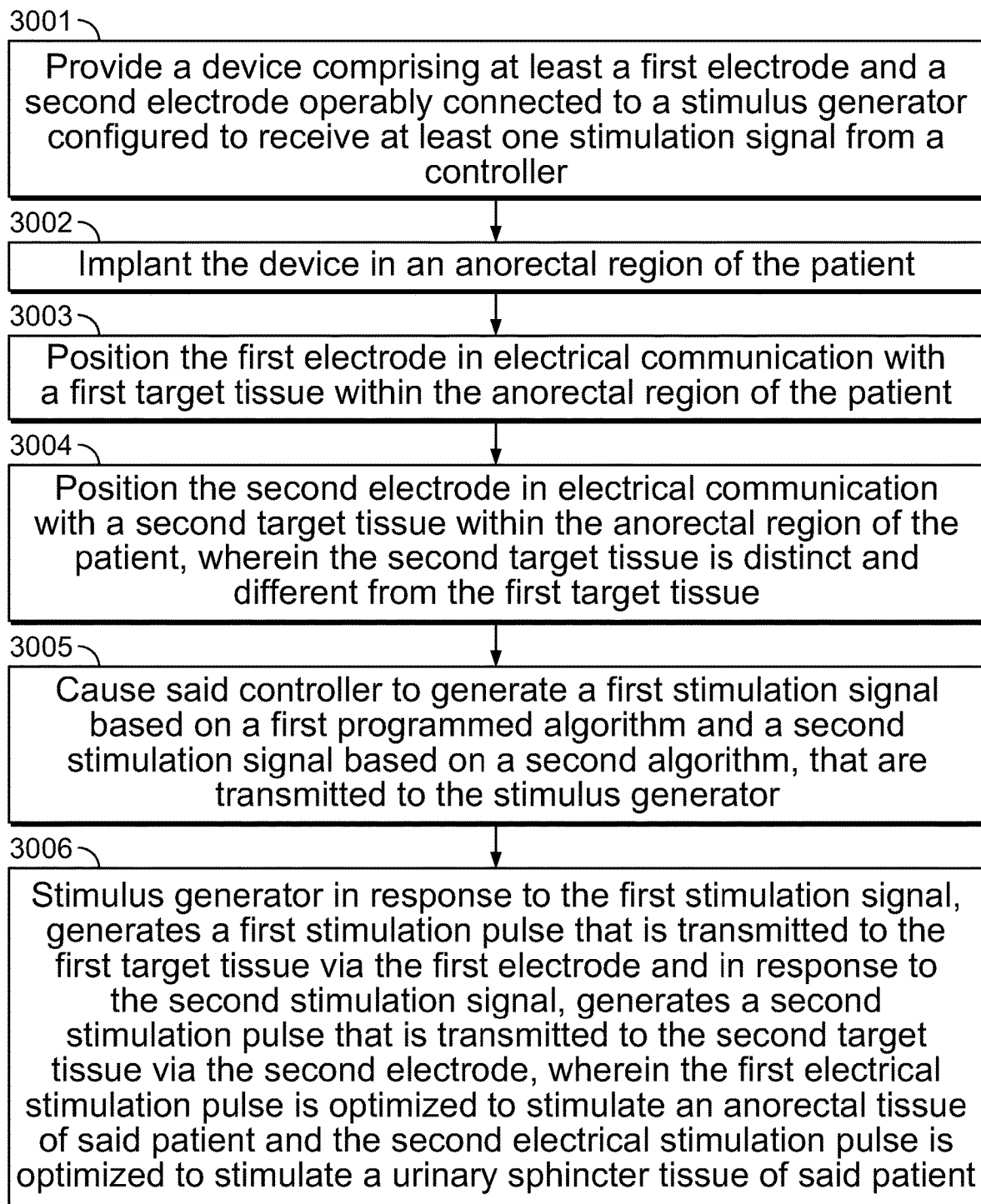
FIG. 30 is a flowchart illustrating a method of treating urinary dysfunction in a patient, according to another embodiment of the present specification.

In another embodiment, the present specification describes a method of treating urinary dysfunction in a patient. This method is shown in FIG. 30 and comprises the following steps: providing a device comprising at least a first electrode and a second electrode operably connected to a stimulus generator configured to receive at least one stimulation signal from a controller in step 3001; implanting said device in the anorectal tissue of the patient in step 3002; positioning said first electrode in electrical communication with a first target tissue within the anorectal region of the patient in step 3003; positioning said second electrode in electrical communication with a second target tissue within the anorectal region of the patient in step 3004, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3005. In step 3006, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first stimulation pulse optimally stimulates the anorectal tissues and said second stimulation pulse optimally stimulates the urinary sphincter tissues.

Figure 31:
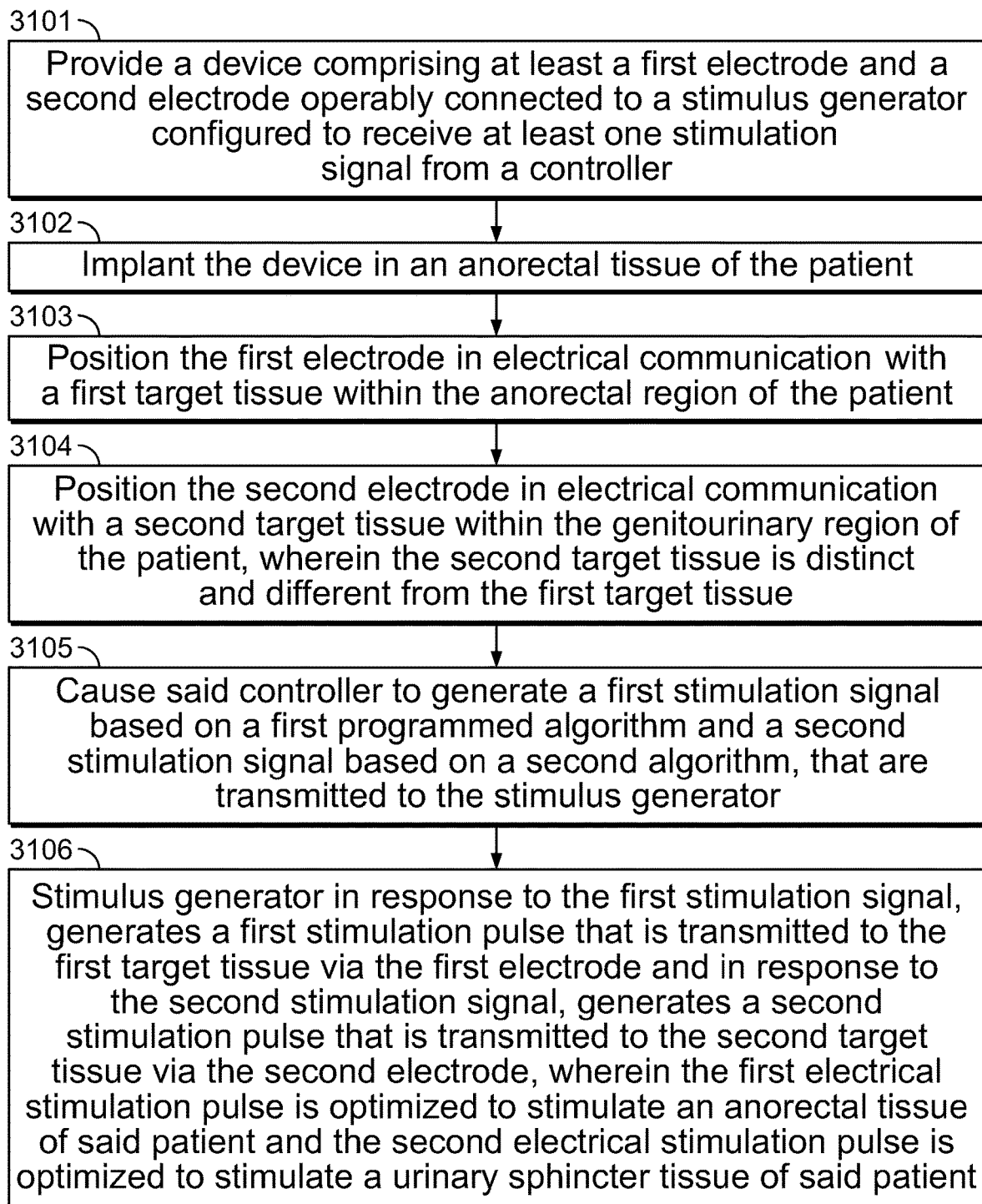
FIG. 31 is a flowchart illustrating a method of treating a fecal and a urinary dysfunction in a patient, according to an embodiment of the present specification.

In another embodiment, the present specification describes a method of treating a fecal and a urinary dysfunction in a patient. This method is shown in FIG. 31 and comprises the following steps: providing a device comprising at least a first electrode and a second electrode operably connected to a stimulus generator configured to receive at least one stimulation signal from a controller in step 3101; implanting said device in the anorectal tissue of the patient in step 3102; positioning said first electrode in electrical communication with a first target tissue within the anorectal region of the patient in step 3103; positioning said second electrode in electrical communication with a second target tissue within the genitourinary region of the patient in step 3104, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3105. In step 3106, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first stimulation pulse optimally stimulates the anorectal tissues and said second stimulation pulse optimally stimulates the urinary sphincter tissues.

In another embodiment, the present specification describes a method of treating a fecal dysfunction and a urinary dysfunction in a patient. This method is shown in FIG. 32 and comprises the following steps: providing a device comprising at least a first electrode and a second electrode operably connected to a stimulus generator configured to receive at least one stimulation signal from a controller in step 3201; implanting said device in an anorectal region and a genitourinary region of said patient in step 3202; positioning said first electrode in electrical communication with a first target tissue within said anorectal region in step 3203; positioning said second electrode in electrical communication with a second target tissue within said genitourinary region in step 3204, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3205. In step 3206, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first stimulation pulse optimally stimulates said first target tissue in said anorectal region and said second stimulation pulse optimally stimulates said second tissue in said genitourinary region.

Figure 33:
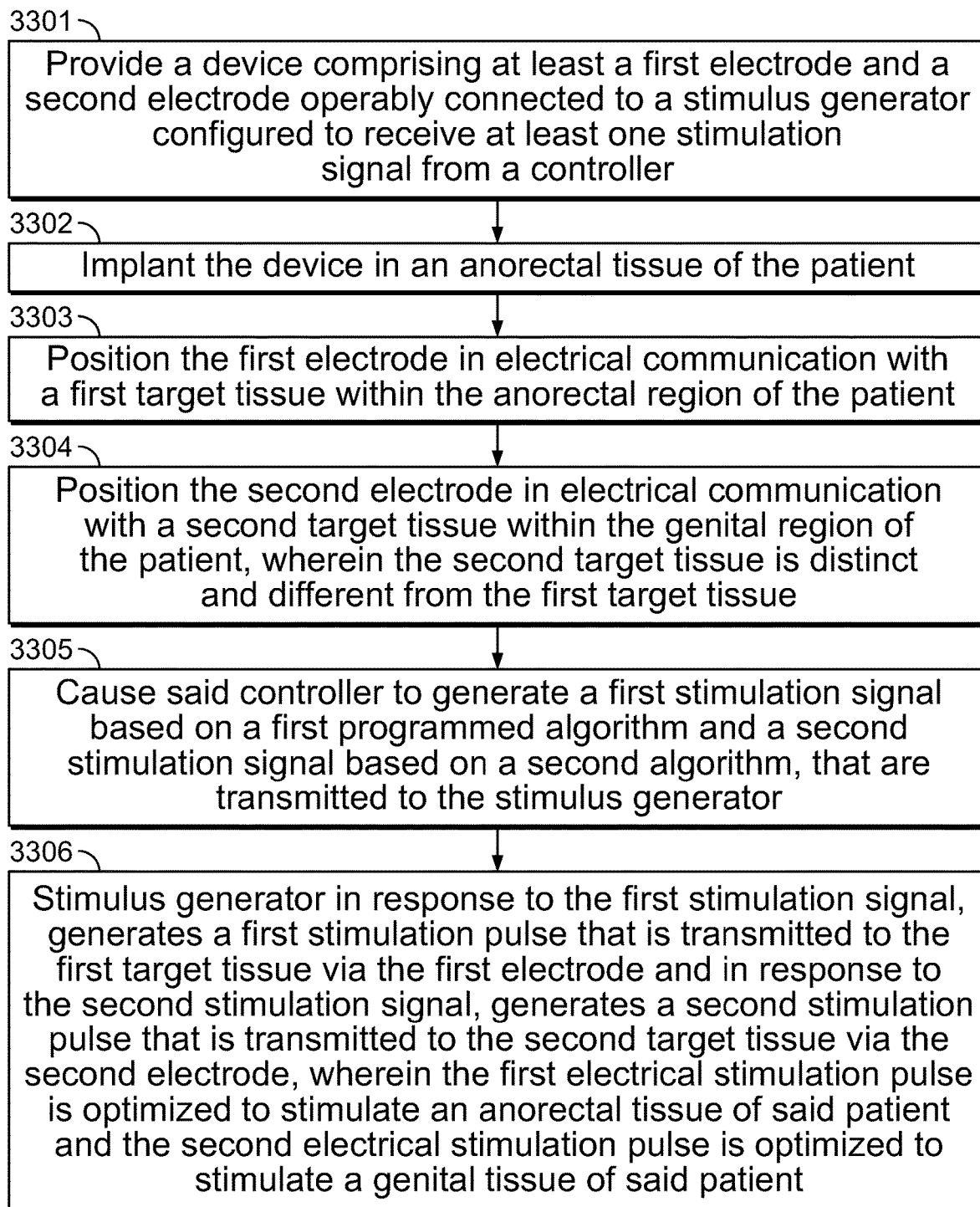
FIG. 33 is a flowchart illustrating a method of treating a urinary dysfunction in a patient, according to another embodiment of the present specification.

In one embodiment, the present specification describes a method of treating a urinary dysfunction in a patient. This method is shown in FIG. 33 and comprises the following steps: providing a device comprising at least a first electrode and a second electrode operably connected to a stimulus generator configured to receive at least one stimulation signal from a controller in step 3301; implanting said device in the anorectal tissue of the patient in step 3302; positioning said first electrode in electrical communication with a first target tissue within the anorectal region of the patient in step 3303; positioning said second electrode in electrical communication with a second target tissue within the genital region of the patient in step 3304, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3305. In step 3306, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first electrical stimulation pulse optimally stimulates anorectal tissues and the second electrical stimulation pulse optimally stimulates genital tissues.

Figure 34:
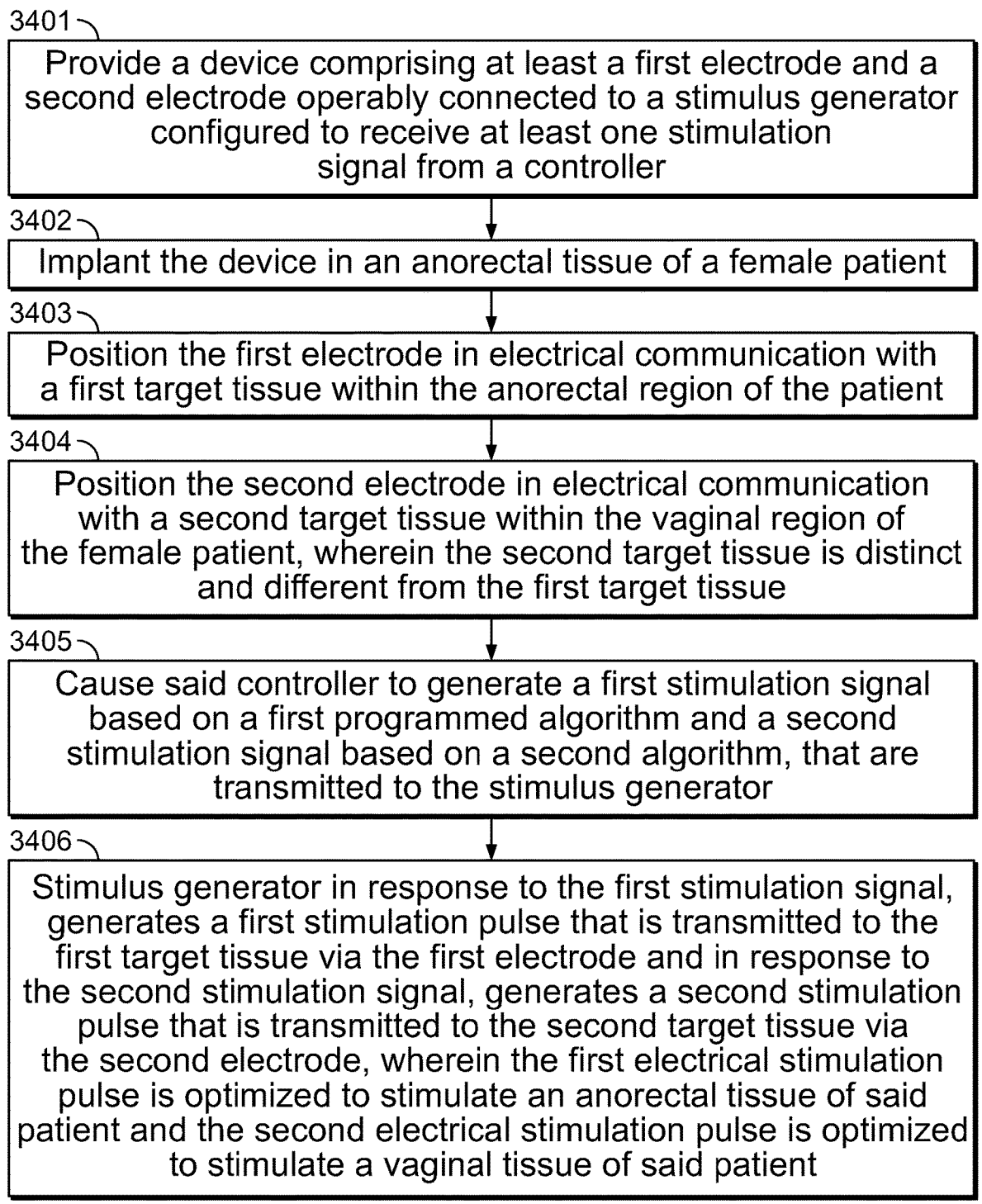
FIG. 34 is a flowchart illustrating a method of treating a urinary dysfunction in a female patient, according to an embodiment of the present specification.

In another embodiment, the present specification describes a method of treating a urinary dysfunction in a female patient. This method is shown in FIG. 34 and comprises the following steps: providing a device comprising at least a first electrode and a second electrode operably connected to a stimulus generator configured to receive at least one stimulation signal from a controller in step 3401; implanting said device in the anorectal tissue of the female patient in step 3402; positioning said first electrode in electrical communication with a first target tissue within the anorectal region of the patient in step 3403; positioning said second electrode in electrical communication with a second target tissue within the vaginal region of the female patient in step 3404, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3405. In step 3406, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said the first electrical stimulation pulse optimally stimulates anorectal tissues and said second electrical stimulation pulse optimally stimulates vaginal tissues.

Figure 35:
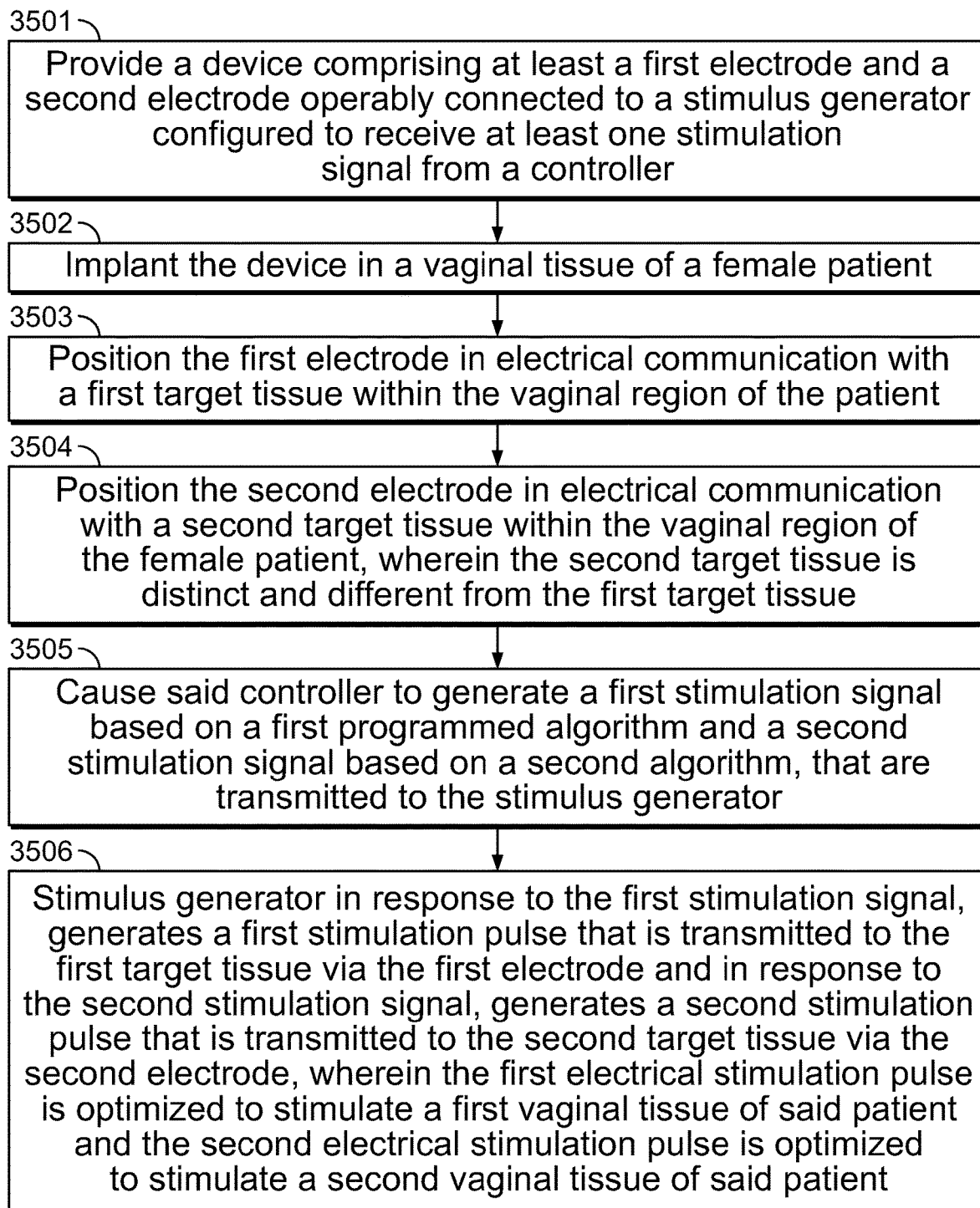
FIG. 35 is a flowchart illustrating a method of treating a urinary dysfunction in a female patient, according to another embodiment of the present specification.

In another embodiment, the present specification describes a method of treating a urinary dysfunction in a female patient. This method is shown in FIG. 35 and comprises the following steps: providing a device comprising at least a first electrode and a second electrode operably connected to a stimulus generator configured to receive at least one stimulation signal from a controller in step 3501; implanting said device in the vaginal tissue of the female patient in step 3502; positioning said first electrode in electrical communication with a first target tissue within the vaginal region of the patient in step 3503; positioning said second electrode in electrical communication with a second target tissue within the vaginal region of the female patient in step 3504, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3505. In step 3506, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein the first electrical stimulation pulse optimally stimulates the first target tissue of the vaginal tissues and the second electrical stimulation pulse optimally stimulates the second target tissue of the vaginal tissues.

Figure 36:
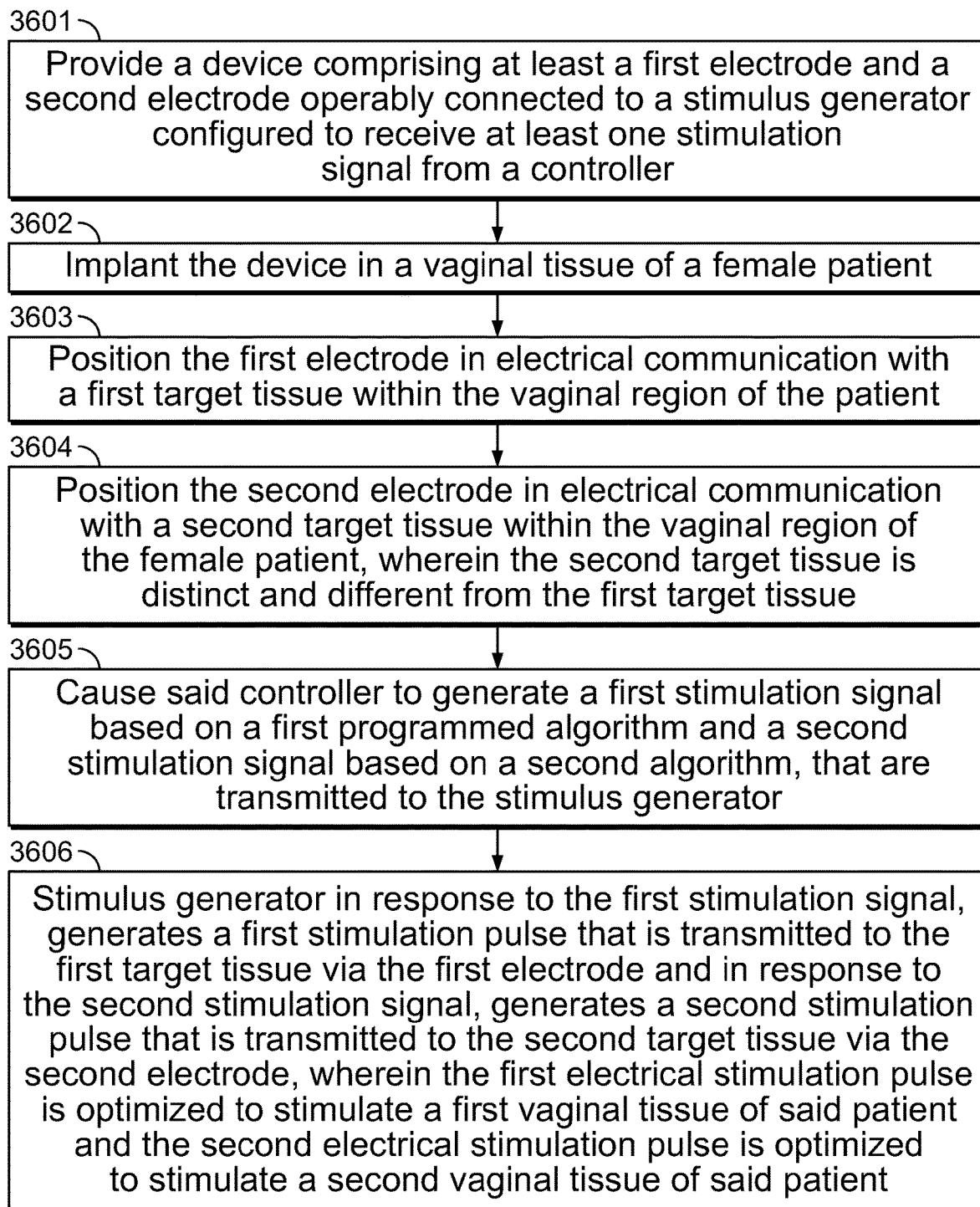
FIG. 36 is a flowchart illustrating a method of treating a vaginal dysfunction in a female patient, according to an embodiment of the present specification.

In another embodiment, the present specification describes a method of treating a vaginal or sexual dysfunction in a female patient. This method is shown in FIG. 36 and comprises the following steps: providing a device comprising at least a first electrode and a second electrode operably connected to a stimulus generator configured to receive at least one stimulation signal from a controller in step 3601; implanting said device in the vaginal tissue of the female patient in step 3602; positioning said first electrode in electrical communication with a first target tissue within the vaginal region of the patient in step 3603; positioning said second electrode in electrical communication with a second target tissue within the vaginal region of the female patient in step 3604, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3605. In step 3606, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first electrical stimulation pulse optimally stimulates the first target tissue of the vaginal tissues and the second electrical stimulation pulse optimally stimulates the second target tissue of the vaginal tissues.

Figure 37:
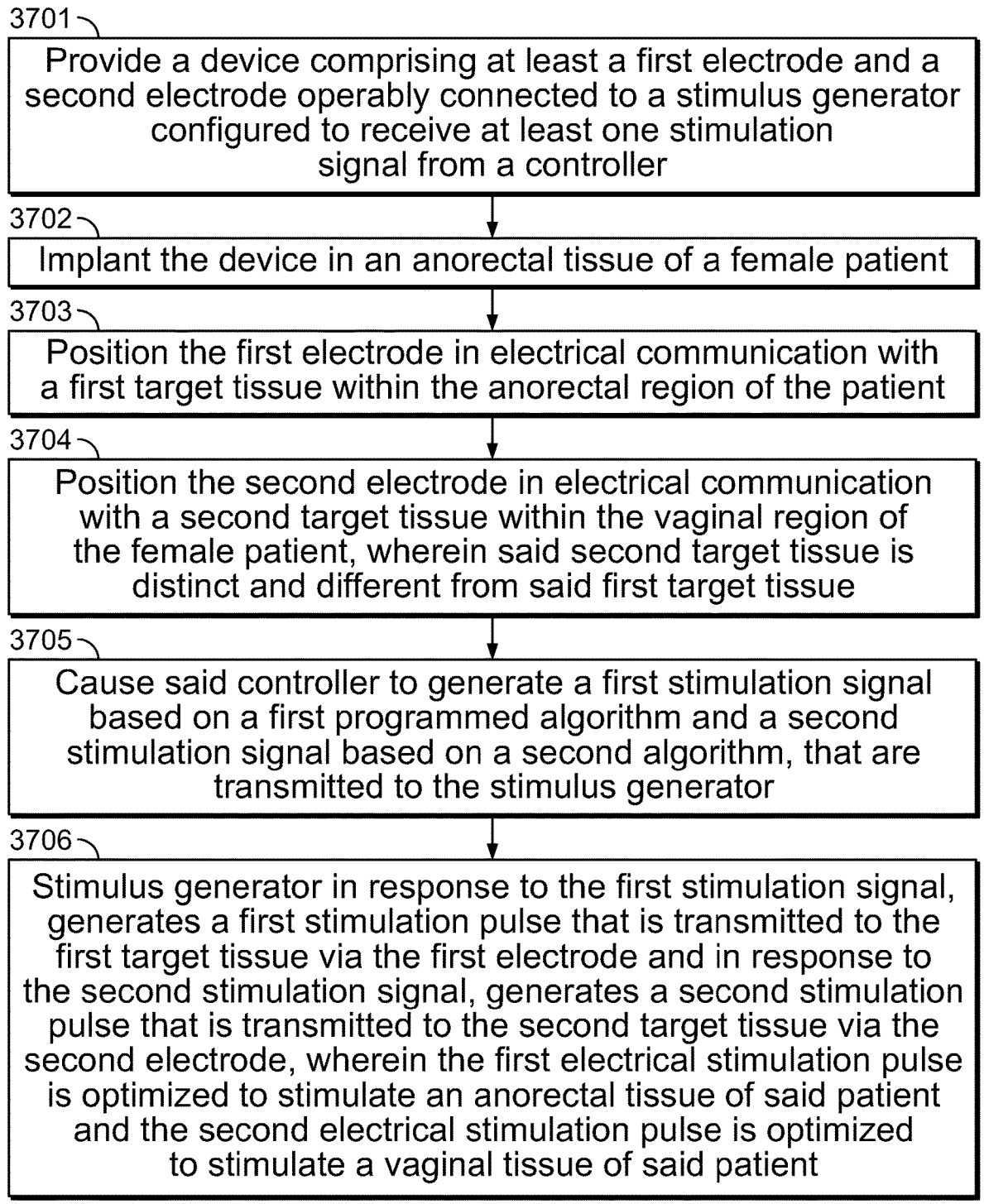
FIG. 37 is a flowchart illustrating a method of treating a vaginal dysfunction in a female patient, according to another embodiment of the present specification.

In another embodiment, the present specification describes a method of treating a vaginal or sexual dysfunction in a female patient. This method is shown in FIG. 37 and comprises the following steps: providing a device comprising at least a first electrode and a second electrode operably connected to a stimulus generator configured to receive at least one stimulation signal from a controller in step 3701; implanting said device in the anorectal tissue of the female patient in step 3702; positioning said first electrode in electrical communication with a first target tissue within the anorectal region of the patient in step 3703; positioning said second electrode in electrical communication with a second target tissue within the vaginal region of the female patient in step 3704, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3705. In step 3706, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein said first electrical stimulation pulse optimally stimulates the anorectal tissues and the second electrical stimulation pulse optimally stimulates the vaginal tissues.

Figure 38:
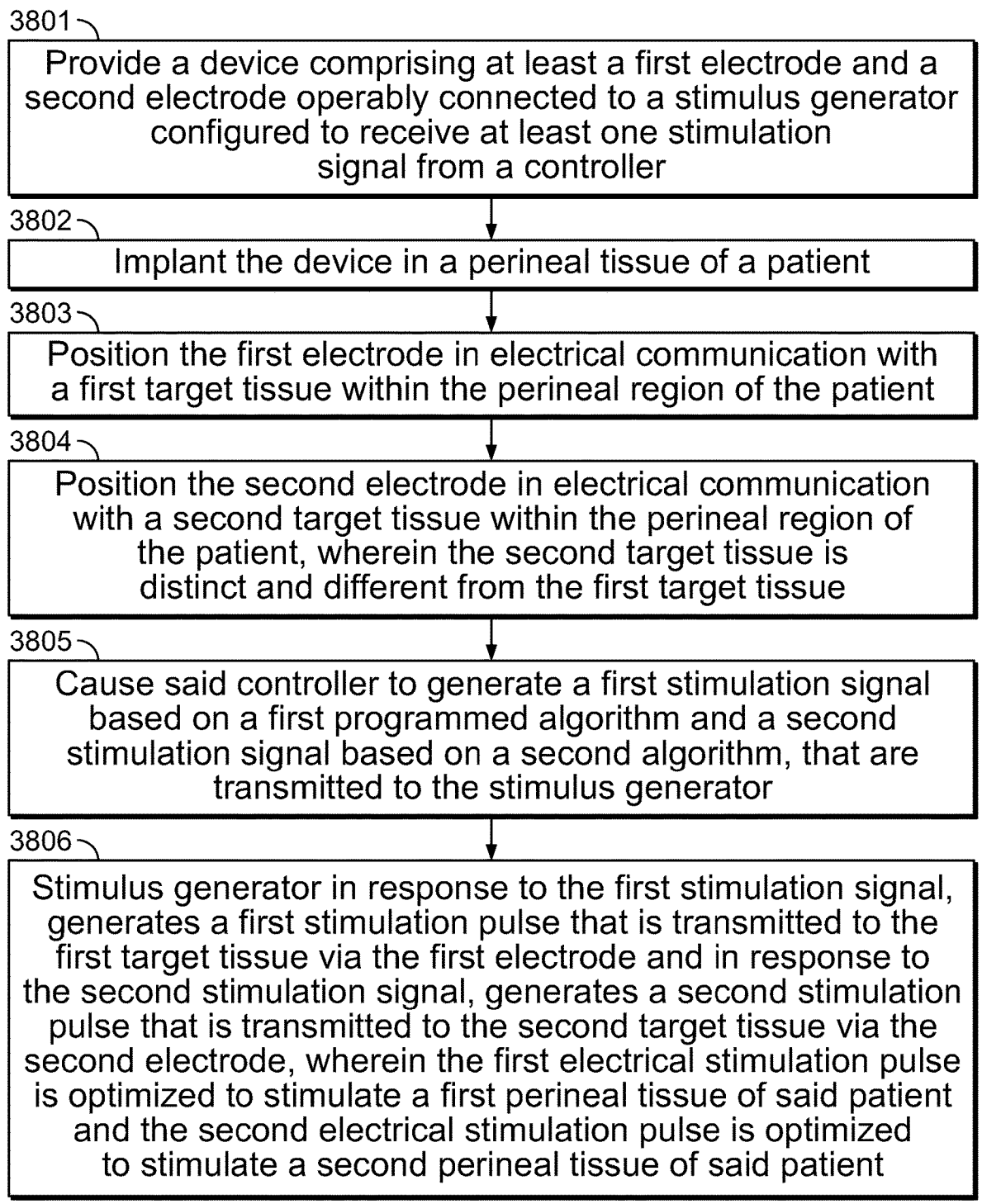
FIG. 38 is a flowchart illustrating a method of treating a genital dysfunction in a patient, according to an embodiment of the present specification.

In another embodiment, the present specification describes a method of treating a genital dysfunction in a patient. This method is shown in FIG. 38 and comprises the following steps: providing a device comprising at least a first electrode and a second electrode operably connected to a stimulus generator configured to receive at least one stimulation signal from a controller in step 3801; implanting said device in the perineal tissue of the patient in step 3802; positioning said first electrode in electrical communication with a first target tissue within the perineal region of the patient in step 3803; positioning said second electrode in electrical communication with a second target tissue within the perineal region of the patient in step 3804, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3805. In step 3806, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein the first electrical stimulation pulse optimally stimulates the first target perineal tissues and said second electrical stimulation pulse optimally stimulates the second target perineal tissues.

In one embodiment, one of the perineal tissues is the perineal body. In another embodiment, one of the perineal tissues is the perineal sponge.

In various embodiments, the device is implanted under the skin proximate an anorectal structure or a urogenital structure. In various embodiments, the electrodes are in electrical communication with a described target structure and are able to electrically stimulate the desired structure without being in physical contact with the structure.

Figure 39:
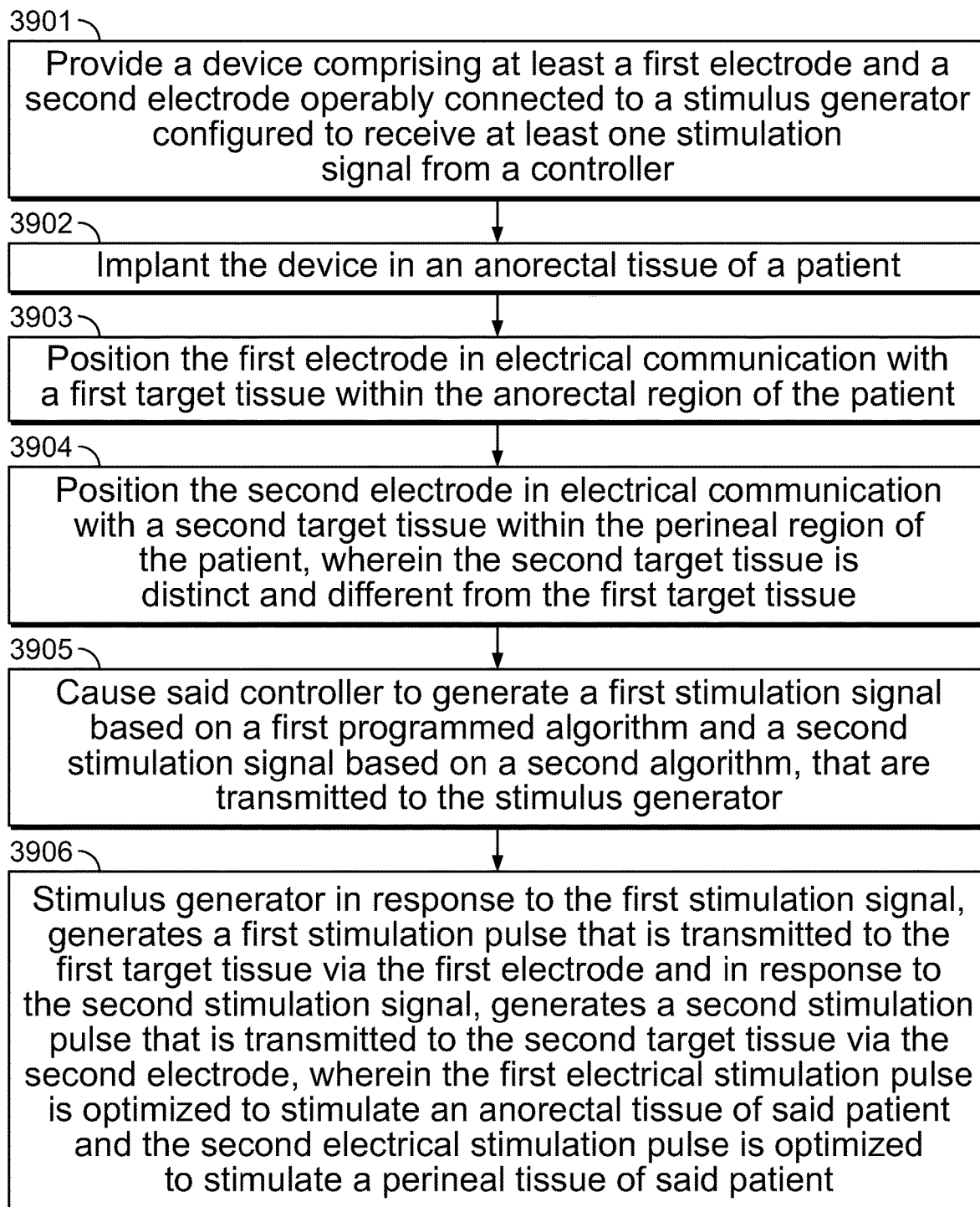
FIG. 39 is a flowchart illustrating a method of treating a urogenital dysfunction in a patient, according to an embodiment of the present specification.

In another embodiment, the present specification describes a method of treating a urogenital dysfunction in a patient. This method is shown in FIG. 39 and comprises the following steps: providing a device comprising at least a first electrode and a second electrode operably connected to a stimulus generator configured to receive at least one stimulation signal from a controller in step 3901; implanting said device in the anorectal tissue of the patient in step 3902; positioning said first electrode in electrical communication with a first target tissue within the anorectal region of the patient in step 3903; positioning said second electrode in electrical communication with a second target tissue within the perineal region of the patient in step 3904, wherein said second target tissue is distinct and different from said first target tissue; and causing said controller to generate a first stimulation signal based on a first programmed algorithm and a second stimulation signal based on a second programmed algorithm, that are transmitted to the stimulus generator in step 3905. In step 3906, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein the first electrical stimulation pulse optimally stimulates the anorectal tissues and the second electrical stimulation pulse optimally stimulates the perineal tissues.

In one embodiment, the perineal tissue is the pelvic plexus. In another embodiment, the perineal tissue is a nerve of the pelvic plexus. In yet another embodiment, the perineal tissue is the perineal nerve.

Figure 40:
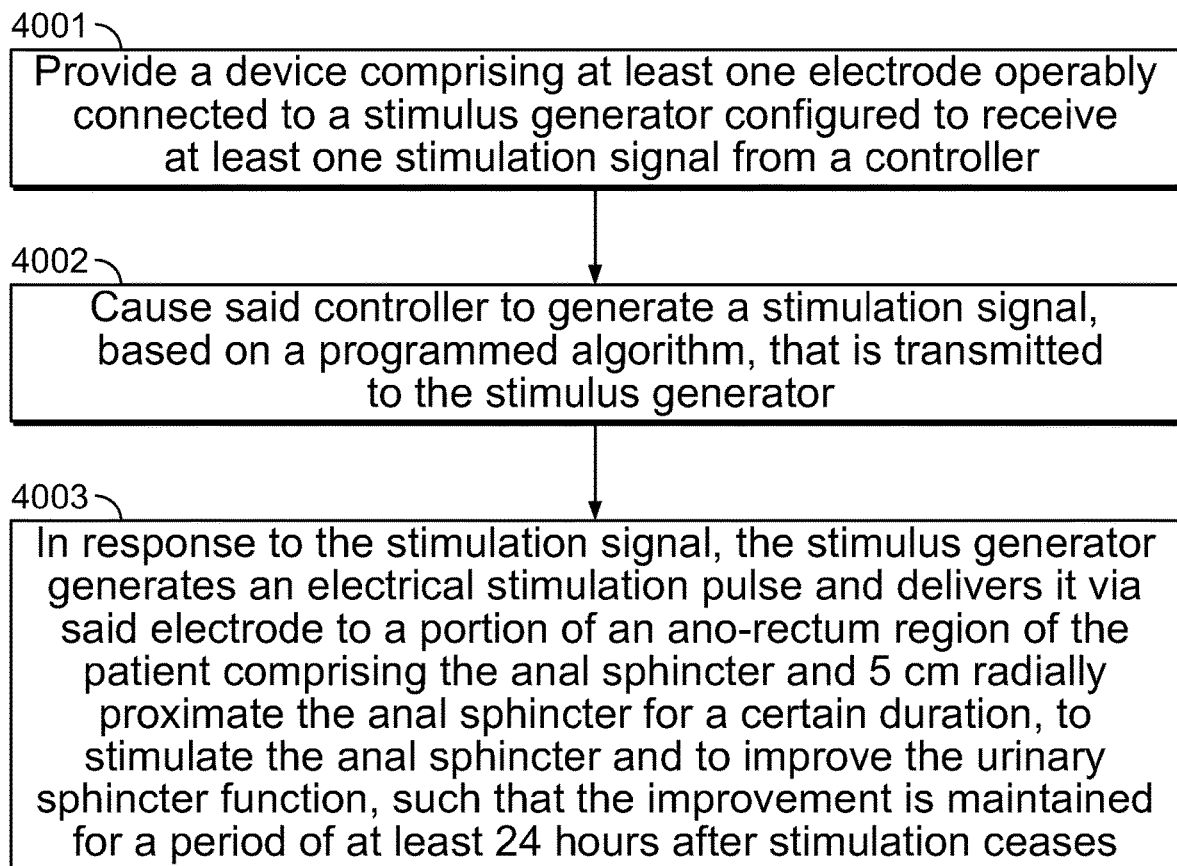
FIG. 40 is a flowchart illustrating a method of modulating urinary sphincter function in a subject in need thereof, in accordance with an embodiment of the present specification.

In another embodiment, the present specification describes a method of modulating urinary sphincter function in a subject in need thereof. This method is shown in FIG. 40 and comprises: providing a device comprising at least one electrode operably connected to a stimulus generator configured to receive at least one stimulation signal from a controller; and causing said controller to generate a stimulation signal, based on a programmed algorithm, that is transmitted to the stimulus generator in step 4002. In step 4003, in response to the stimulation signal, the stimulus generator generates an electrical stimulation pulse and delivers it via said at least one electrode to a portion of a region encompassing an ano-rectum of the subject for a certain duration, wherein said region comprises the anal sphincter and 5 cm radially proximate the anal sphincter, to stimulate the anal sphincter and to improve the urinary sphincter function, wherein said electrical stimulation pulse is adapted to cause said urinary sphincter function improvement to be maintained for a period of at least 24 hour after stimulation ceases.

Figure 41:
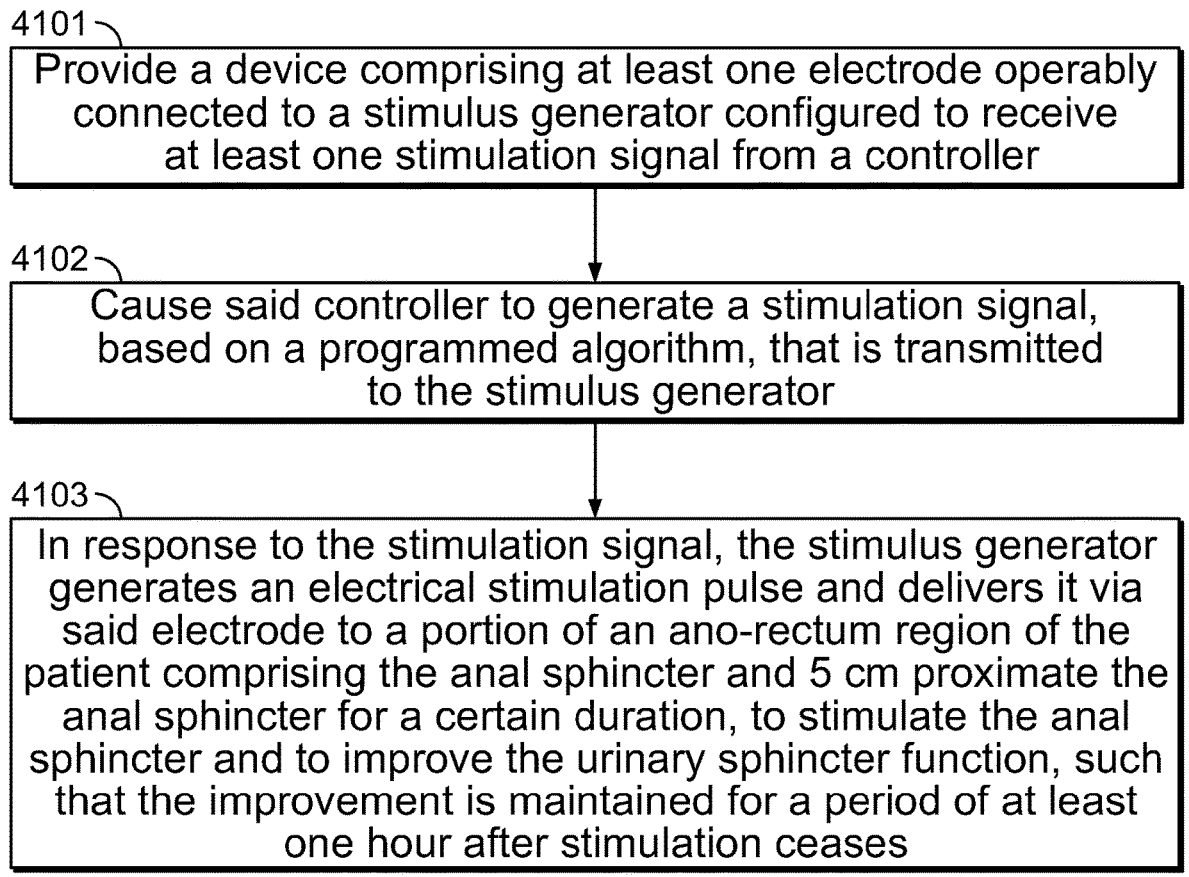
FIG. 41 is a flowchart illustrating a method of modulating urinary sphincter function in a subject in need thereof, according to another embodiment of the present specification.

In another embodiment, the present specification describes a method of modulating urinary sphincter function in a subject in need thereof. This method is shown in FIG. 41 and comprises: providing a device comprising at least one electrode operably connected to a stimulus generator configured to receive at least one stimulation signal from a controller; and causing said controller to generate a stimulation signal, based on a programmed algorithm, that is transmitted to the stimulus generator in step 4102. In step 4103, in response to the stimulation signal, the stimulus generator generates an electrical stimulation pulse and delivers it via said at least one electrode to a portion of a region encompassing an ano-rectum of the subject for a certain duration, wherein said region comprises the anal sphincter and 5 cm proximate the anal sphincter, to stimulate the anal sphincter and to improve the urinary sphincter function, wherein said electrical stimulation pulse is adapted to cause said urinary sphincter function improvement to be maintained for a period of at least one hour after stimulation ceases.

In the embodiments described above, the improvement may be maintained for a period greater than one hour or a period greater than 24 hours after stimulation ceases. In the embodiments described above, stimulation may be continuous or intermittent.

Figure 42:
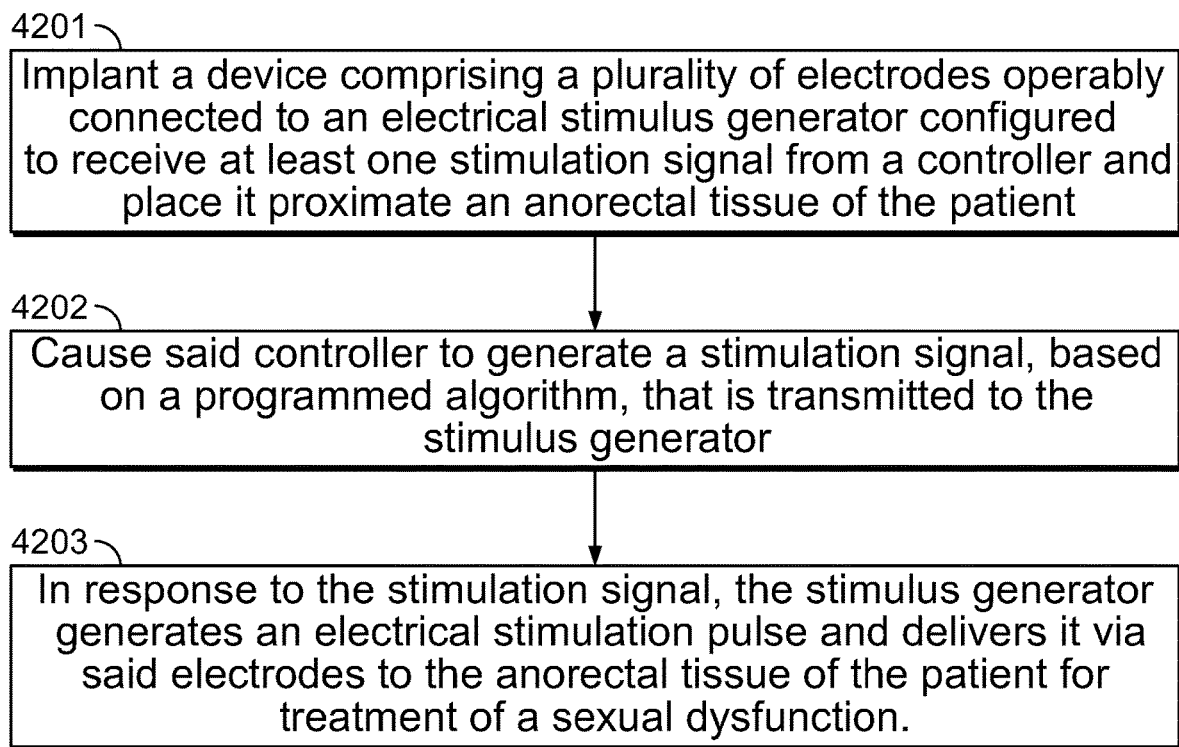
FIG. 42 is a flowchart illustrating a method of treating a sexual dysfunction in a patient, according to an embodiment of the present specification.

In another embodiment, the present specification describes a method of treating a sexual dysfunction in a patient. This method is shown in FIG. 42 and comprises the following steps: implanting a device comprising a plurality of electrodes operably connected to an electrical stimulus generator configured to receive at least one stimulation signal from a controller and placed proximate an anorectal tissue of the patient in step 4201; and causing said controller to generate a stimulation signal, based on a programmed algorithm, that is transmitted to the stimulus generator in step 4202. In step 4203, in response to the stimulation signal, said stimulus generator generates an electrical stimulation pulse and delivers said electrical stimulation pulse via said electrodes to the anorectal tissue of the patient to cause a stimulation of said anorectal tissue of the patient, wherein the delivery of said electrical stimulation pulse substantially treats a sexual dysfunction.

Figure 43:
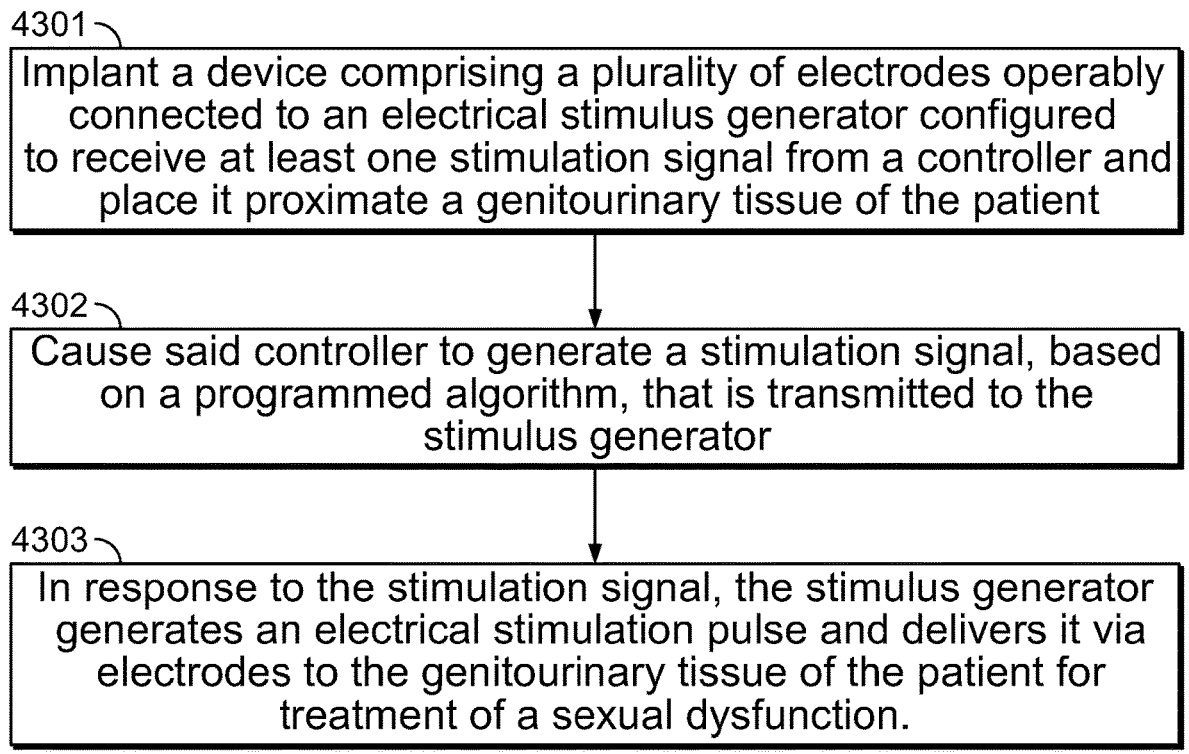
FIG. 43 is a flowchart illustrating a method of treating a sexual dysfunction in a patient, according to another embodiment of the present specification.

In another embodiment, the present specification describes a method of treating a sexual dysfunction in a patient. This method is shown in FIG. 43 and comprises the following steps: implanting a device comprising a plurality of electrodes operably connected to an electrical stimulus generator configured to receive at least one stimulation signal from a controller and placed proximate a genitourinary tissue of the patient in step 4301; and causing said controller to generate a stimulation signal, based on a programmed algorithm, that is transmitted to the stimulus generator in step 4302. In step 4303, in response to the stimulation signal, said stimulus generator generates an electrical stimulation pulse and delivers said electrical stimulation pulse via said electrodes to the genitourinary tissue of the patient to cause a stimulation of said genitourinary tissue of the patient in step 4302, wherein the delivery of said electrical stimulation pulse treats a sexual dysfunction.

Optionally, the stimulation is timed to a urinary function, a bowel function or a sexual function. Optionally, the stimulation is delivered independent of a urinary function, a bowel function or a sexual function and, after at least a single session of stimulation, results in improvement in at least one of the above mentioned functions that lasts beyond the duration of stimulation.

Optionally, the stimulation is delivered to instantaneously improve a urinary function, a bowel function or a sexual function. Optionally, the stimulation is delivered to slowly improve a urinary function, a bowel function or a sexual function over time. Optionally, the improvement in one of the above mentioned functions occurs at least 5 minutes after the initiation of stimulation.

Figure 44:
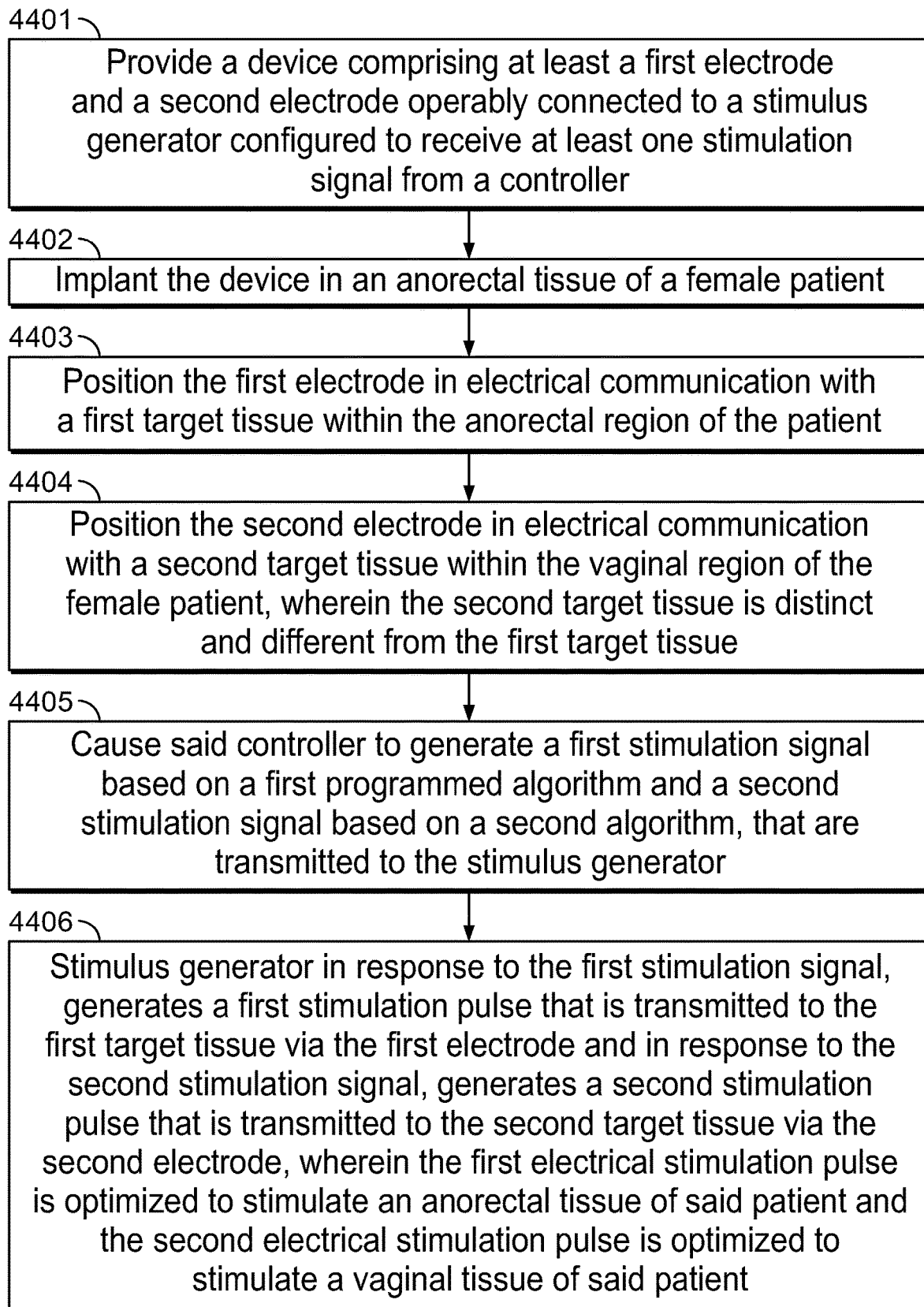
FIG. 44 is a flowchart illustrating a method of treating a urogenital dysfunction in a female patient, according to one embodiment of the present specification.

In another embodiment, the present specification describes a method of treating a urogenital dysfunction in a female patient. This method is shown in FIG. 44 and comprises the following steps: providing a device comprising at least a first electrode and a second electrode operably connected to a stimulus generator configured to receive at least one stimulation signal from a controller in step 4401; implanting said device in the anorectal tissue of the female patient in step 4402; positioning said first electrode in electrical communication with a first target tissue within the anorectal region of the patient in step 4403; positioning said second electrode in electrical communication with a second target tissue within the vaginal region of the female patient in step 4404, wherein said second target tissue is distinct and different from said first target tissue; and, causing said controller to generate a first stimulation signal based on a first programmed algorithm and a second stimulation signal based on a second programmed algorithm, that are transmitted to the stimulus generator in step 4405. In step 4406, the stimulus generator, in response to the first stimulation signal generates a first electrical stimulation pulse that is transmitted to said first target tissue via said first electrode, and in response to second stimulation signal generates a second electrical stimulation pulse that is transmitted to said second target tissue via said second electrode, wherein the first electrical stimulation pulse optimally stimulates the anorectal tissues and the second electrical stimulation pulse optimally stimulates the vaginal tissues.

Figure 11C:
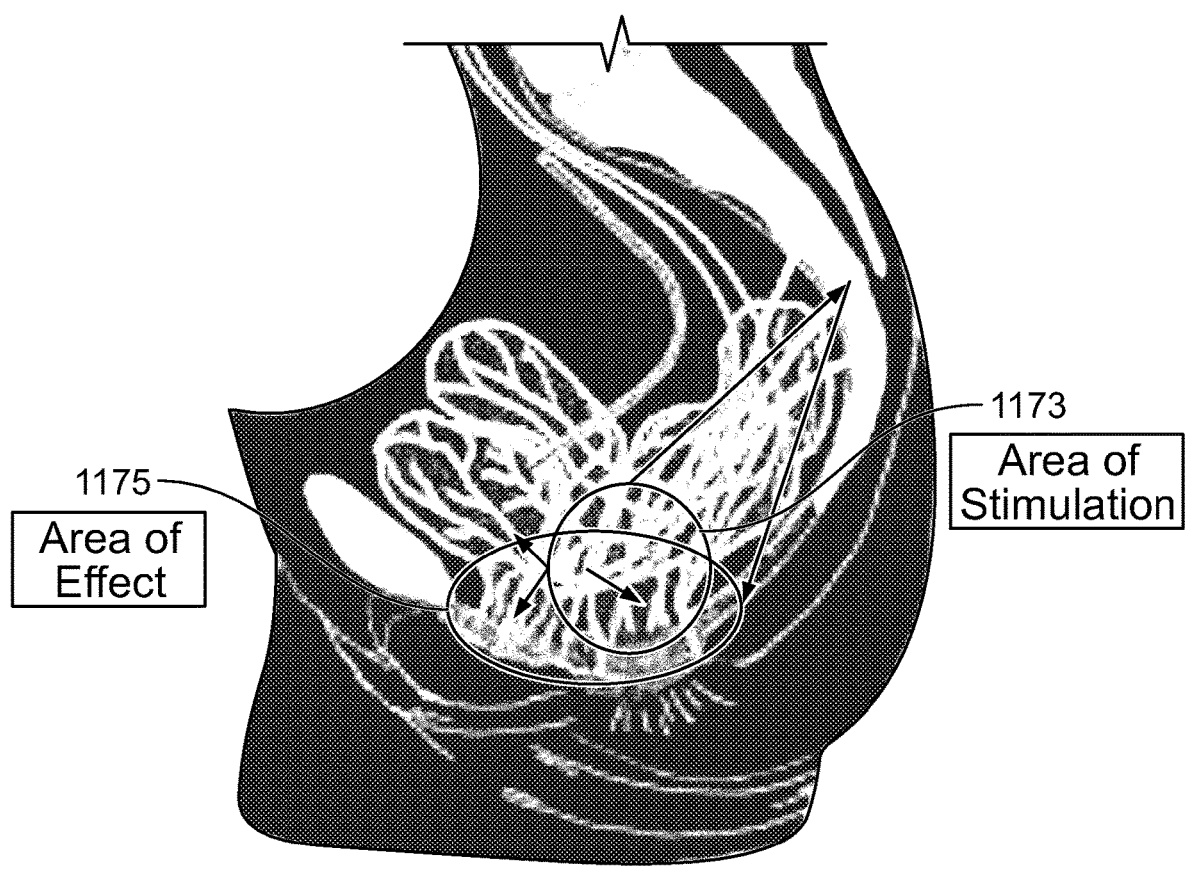
FIG. 11C is an illustration of the lower abdominal region and pelvic region of a patient, depicting a target area for electrical stimulation and an intended area of effect, in accordance with some embodiments of the present specification.

FIG. 11C is an illustration of the lower abdominal region and pelvic region of a patient, depicting a target area for electrical stimulation 1173 and an intended area of effect 1175, in accordance with some embodiments of the present specification. FIG. 11C illustrates that, according to some aspects of the present specification, specific areas of the anorectal and genitourinary regions may be stimulated electrically, either independently or cooperatively, to produce a desired therapeutic effect in either region or both regions, as described in a plurality of exemplary embodiments in Table 1 below:

TABLE 1

Electrode permutations and combinations for stimulating an anorectal and/or urogenital structure to modulate function of said structure and/or another structure.

| Example 1 | Anal Sphincter | Urinary Sphincter |
|---|---|---|
| Electrode 1 | + | − |
| Electrode 2 | − | + |
| Function | Anorectal/Genitourinary | Anorectal/Genitourinary |
| Example 2 | Anal Sphincter | Vaginal tissue |
| Electrode 1 | + | − |
| Electrode 2 | − | + |
| Function | Anorectal/Genitourinary | Anorectal/Genitourinary |
| Example 3 | Anal Sphincter | Perineal Tissue |
| Electrode 1 | + | − |
| Electrode 2 | − | + |
| Function | Anorectal/Genitourinary | Anorectal/Genitourinary |
| Example 4 | Vaginal Tissue | Vaginal Tissue |
| Electrode 1 | + | − |
| Electrode 2 | − | + |
| Function | Anorectal/Genitourinary | Anorectal/Genitourinary |
| Example 5 | Vaginal Tissue | Perineal Tissue |
| Electrode 1 | + | − |
| Electrode 2 | − | + |
| Function | Anorectal/Genitourinary | Anorectal/Genitourinary |
| Example 6 | Anal Sphincter | Urinary Sphincter |
| Electrode 1 | + | + |
| Electrode 2 | + | + |
| Function | Urinary Sphincter | Anal Sphincter |

In example 1, a first electrode is positioned to stimulate an anal sphincter while a second electrode is positioned to stimulate a urinary sphincter wherein the effect is to modulate the function of any anorectal and/or genitourinary structure. In example 2, a first electrode is positioned to stimulate an anal sphincter while a second electrode is positioned to stimulate a vaginal tissue wherein the effect is to modulate the function of any anorectal and/or genitourinary structure. In example 3, a first electrode is positioned to stimulate an anal sphincter while a second electrode is positioned to stimulate a perineal tissue wherein the effect is to modulate the function of any anorectal and/or genitourinary structure. In example 4, a first electrode is positioned to stimulate a first portion of vaginal tissue while a second electrode is positioned to stimulate a second portion of vaginal tissue distinct and separate from said first portion of vaginal tissue, wherein the effect is to modulate the function of any anorectal and/or genitourinary structure. In example 5, a first electrode is positioned to stimulate a vaginal tissue while a second electrode is positioned to stimulate a perineal tissue wherein the effect is to modulate the function of any anorectal and/or genitourinary structure. In example 6, a first electrode is positioned to stimulate both an anal sphincter and a urinary sphincter while a second electrode is positioned to stimulate said anal sphincter and said urinary sphincter, wherein the effect of said stimulation of both electrodes on said anal sphincter is to modulate the function of said urinary sphincter while the effect of said stimulation of both electrodes on said urinary sphincter is to modulate the function of said anal sphincter. While stimulating the anal sphincter to modulate anal sphincter function and stimulating the urinary sphincter to modulate urinary sphincter function has been described in the prior art, the present specification describes stimulating one to modulate the function of the other.

Figure 11D:
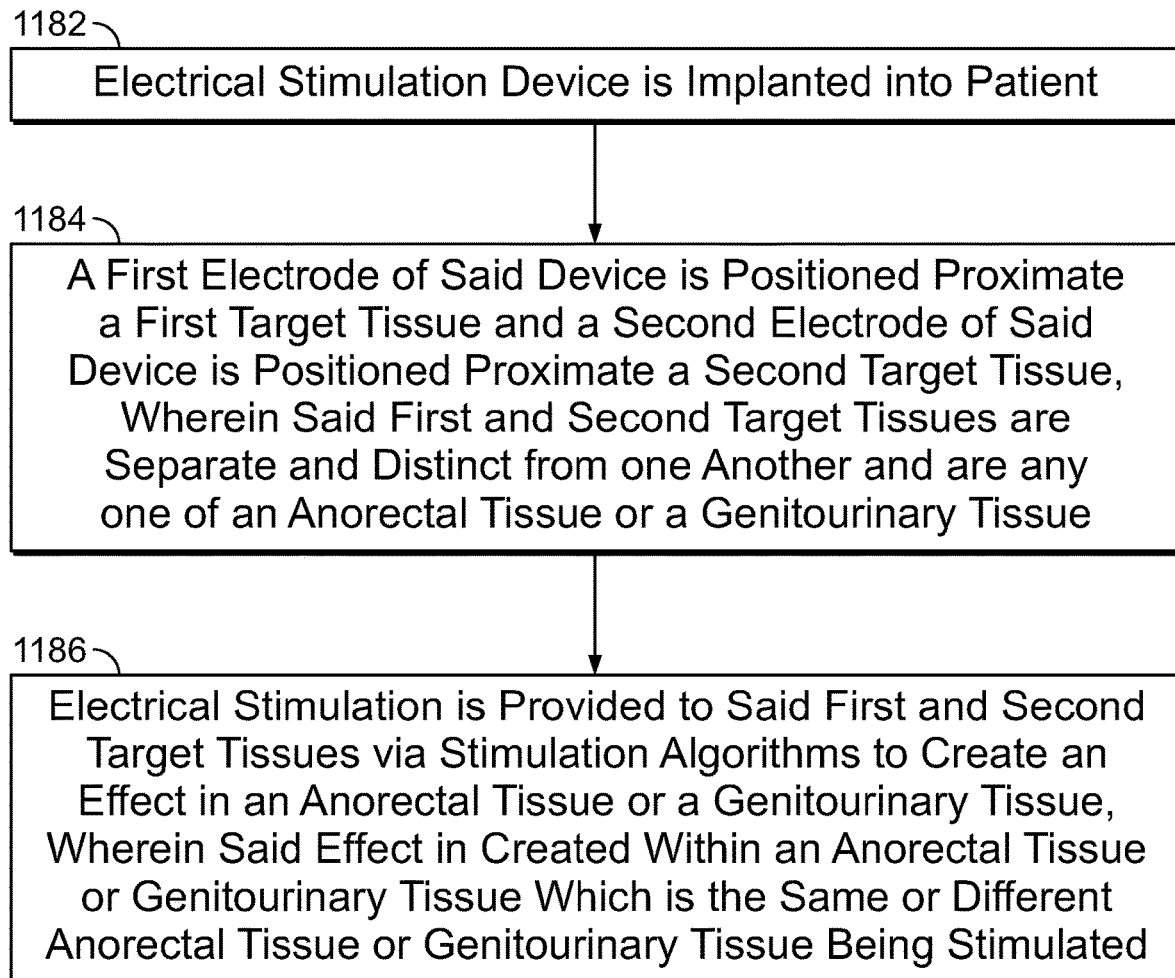
FIG. 11D is a flowchart illustrating the steps involved in some embodiments of providing stimulation to anorectal and/or genitourinary structures to create an effect in the same or different structures being stimulated.

FIG. 11D is a flowchart illustrating the steps involved in some embodiments of providing stimulation to anorectal and/or genitourinary structures to create an effect in the same or different structures being stimulated. At step 1182, an electrical stimulation device is implanted into a patient. Then, at step 1184, a first electrode of said device is positioned proximate a first target tissue and a second electrode of said device is positioned proximate a second target tissue, wherein said first and second target tissues are the same or separate and distinct from one another and are any one of an anorectal tissue or a genitourinary tissue. At step 1186, electrical stimulation is provided to said first and second target tissues via stimulation algorithms to create an effect in an anorectal tissue or a genitourinary tissue, wherein said effect in created within an anorectal tissue or genitourinary tissue which is the same as, or different from, the anorectal tissue or genitourinary tissue being stimulated. In some embodiments, the stimulation algorithm provided to the first electrode is the same as the stimulation algorithm provided to the second electrode. In other embodiments, the stimulation algorithms are different.

Figure 12C:
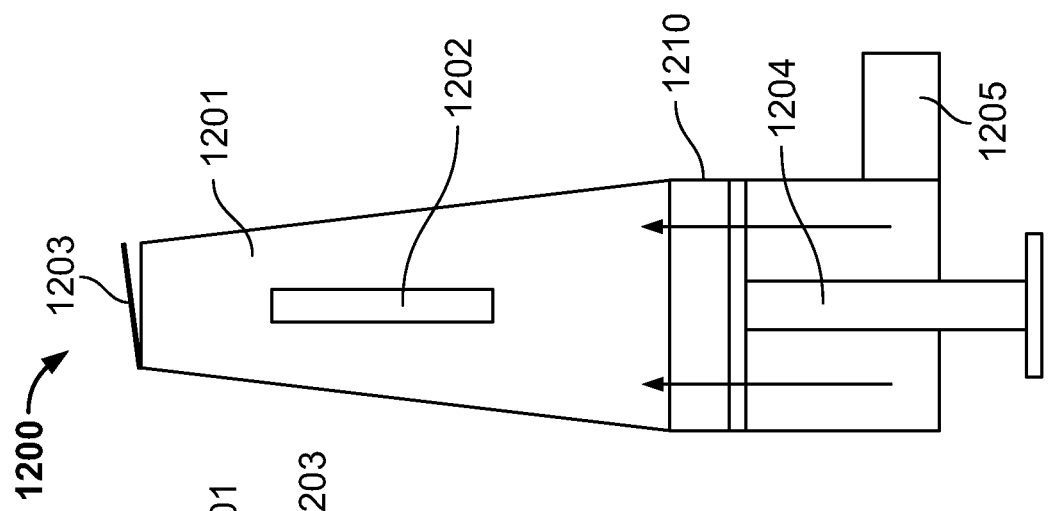
FIG. 12C is an illustration of the same embodiment of an exemplary insertion device of FIG. 12A, depicting the step of pushing the plunger of the insertion device upward to release anorectal tissue.
Figure 12B:
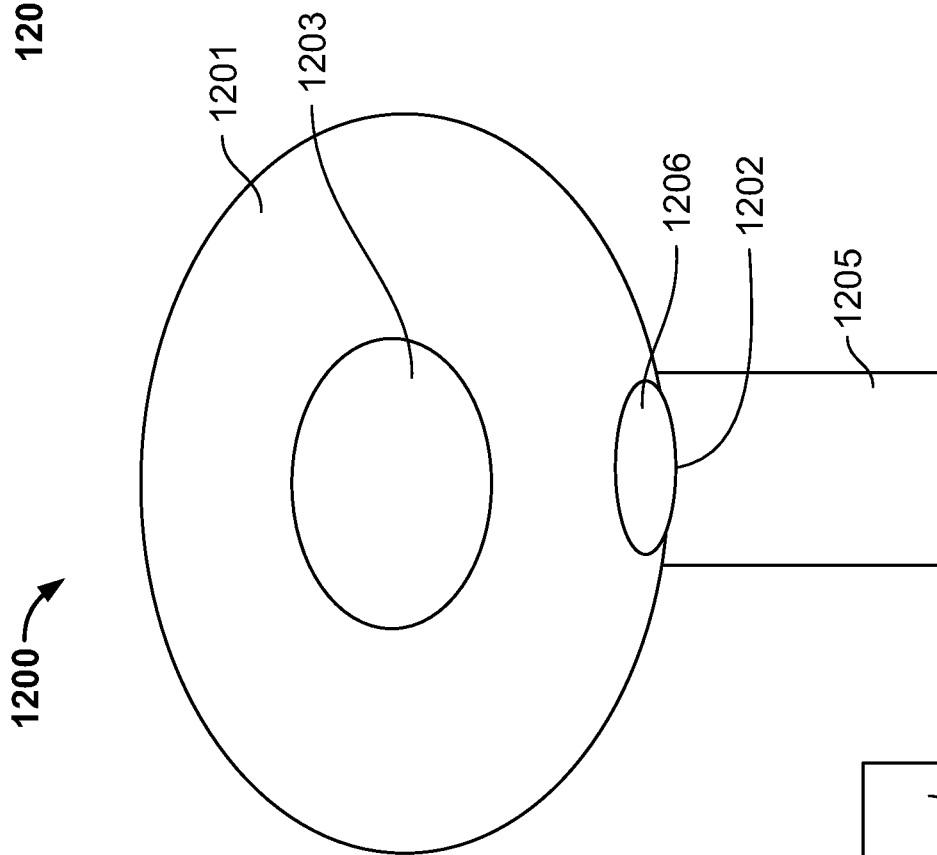
FIG. 12B is a top-down view illustration of the same embodiment of an exemplary insertion device of FIG. 12A, depicting a portion of anorectal tissue suctioned into the device.
Figure 12A:
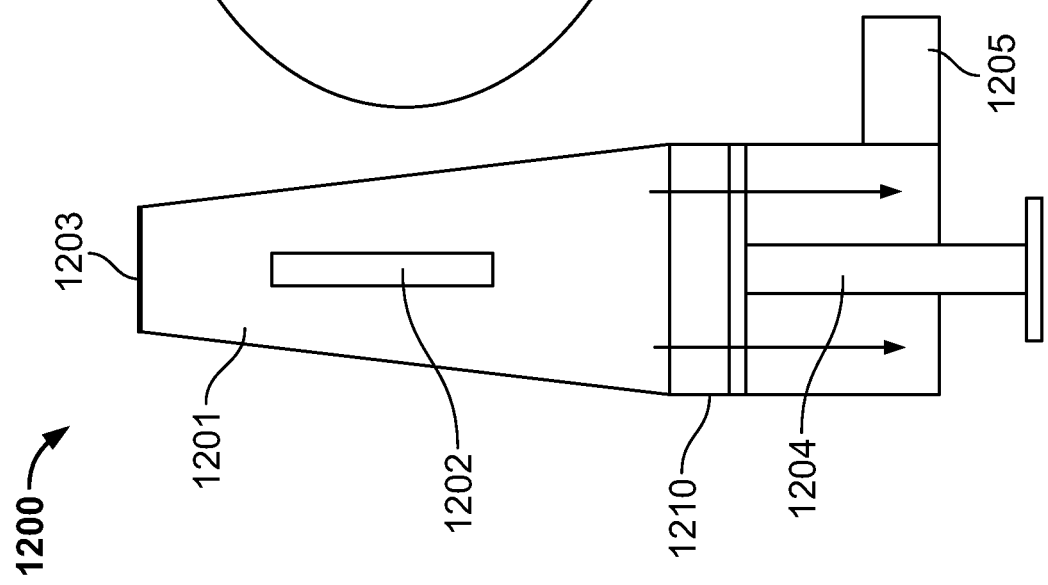
FIG. 12A is an illustration of one embodiment of an exemplary insertion device, depicting the step of pulling the plunger of the insertion device downward to create a vacuum thereby suctioning in a portion of anorectal tissue.

To facilitate quick, easy and comfortable implantation of the microdevice, the present specification further provides an insertion device and catheter. FIGS. 12A through 12C depict various configurations of an embodiment of the insertion device 1200. FIG. 12A is an illustration of one embodiment of an exemplary insertion device 1200, depicting the step of pulling the plunger 1204 of the insertion device downward to create a vacuum and suck in a portion of anorectal tissue. FIG. 12B is a top-down view illustration of the same embodiment of an exemplary insertion device 1200 of FIG. 12A, depicting a portion of anorectal tissue 1206 sucked into the device. FIG. 12C is an illustration of the same embodiment of an exemplary insertion device 1200 of FIG. 12A, depicting the step of pushing the plunger 1204 of the insertion device 1200 upward to release the anorectal tissue.

In one embodiment, the insertion device 1200 comprises a generally conical portion 1201 that has a slot 1202 at a distance from a circular opening at the top that, in one embodiment, is covered with an optional movable valve 1203. A plunger 1204 slides through the lower cylindrical portion 1210 that also includes handle 1205. In one embodiment, a generally cylindrical channel is pre-formed within the insertion device 1200 through which a catheter is passed to implant the microdevice into the rectal mucosa and submucosa which has been sucked-in through the slot 1202. FIG. 12A specifically depicts the plunger 1204 being pulled downward to create a vacuum (with the valve 1203 closing) to suck anorectal tissue 1206 (seen in FIG. 12B), such as rectal mucosa and submucosa, into the slot 1202 of the insertion device 1200. FIG. 12B shows a top view of the insertion device 1200 with a requisite portion of the rectal mucosa and submucosa 1206 sucked into the slot 1202. A microdevice can then be inserted into the sucked-in tissue 1206 using a catheter as discussed later below. As shown in FIG. 12C, pushing the plunger 1204 upward opens the optional valve 1203, releasing the vacuum and also releasing the sucked-in tissue 1206 after the microdevice has been implanted therein.

FIGS. 13A through 13E depict various configurations of an embodiment of an implantation catheter 1300. The catheter 1300 is designed to pass through a pre-formed channel within the insertion device. FIG. 13A is an illustration of one embodiment of an exemplary configuration of an implantation catheter 1300 with a pusher 1312 and attached microdevice 1310 arranged predominantly parallel to each other within said catheter 1300. The catheter 1300 comprises an outer sheath 1311 to restrain a pusher 1312 and a microdevice 1310. At the pre-deployment stage of FIG. 13A, the pusher 1312 and microdevice 1310 are arranged to be predominantly parallel to each other and restrained within the sheath 1311. To facilitate this arrangement, a flexible portion 1320 of the leading end of the pusher 1312 is bent back inwards to form a sharp needle-like edge 1315. The microdevice 1310 is held at the tip of the inwardly bent portion 1320 of the pusher 1312.

Figure 14B:
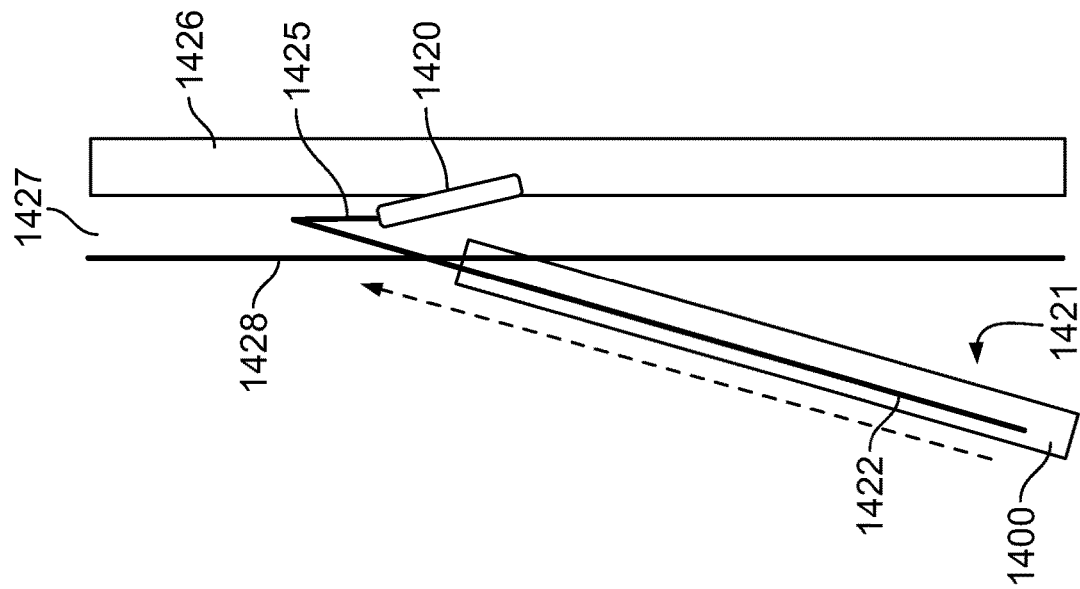
FIG. 14B is an illustration of the same embodiment of an exemplary configuration of an implantation catheter of FIG. 14A, depicting the step of a microdevice being pushed out of the catheter for implantation.
Figure 14A:
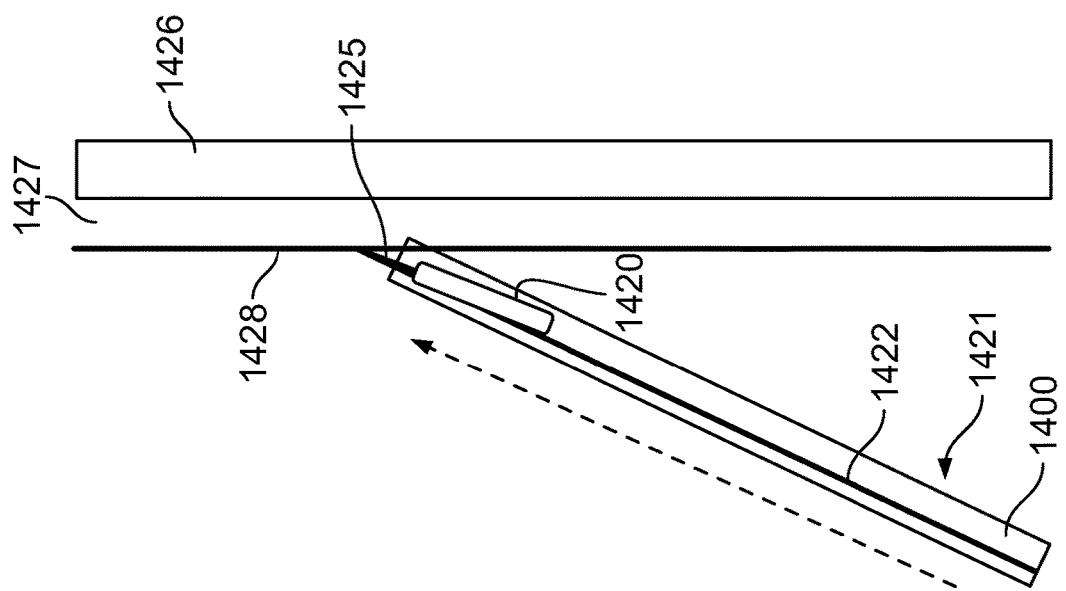
FIG. 14A is an illustration of one embodiment of an exemplary configuration of an implantation catheter, depicting said catheter positioned near the intestinal mucosa of a patient.
Figure 14C:
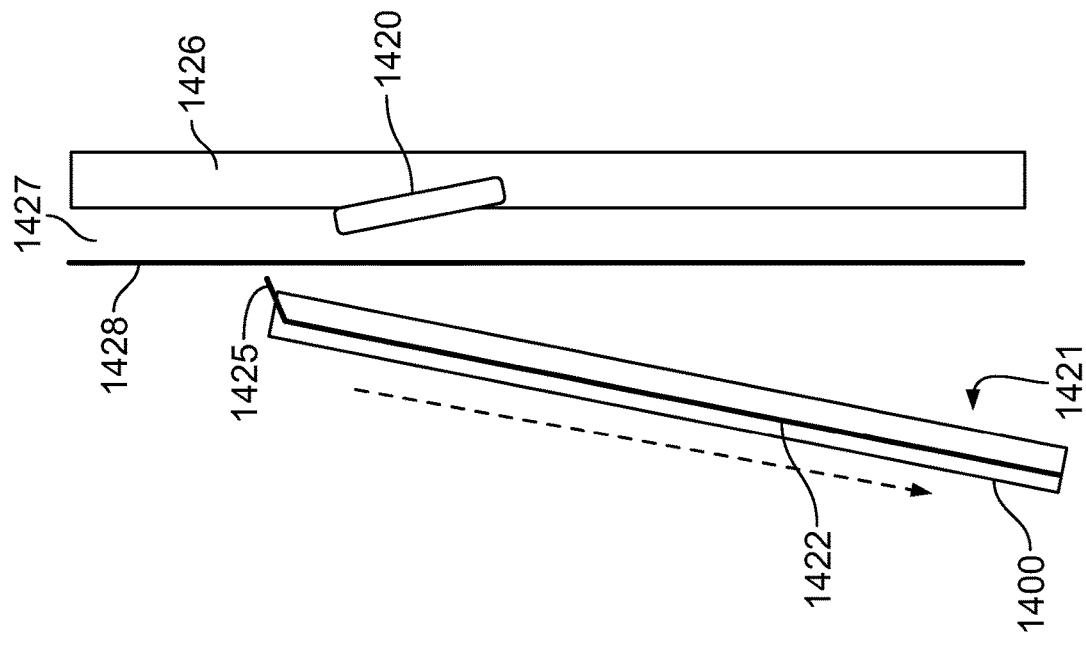
FIG. 14C is an illustration of the same embodiment of an exemplary configuration of an implantation catheter of FIG. 14A, depicting the step of the microdevice being deployed deeper into the tissue site due to straightening of the bent portion.
Figure 14D:
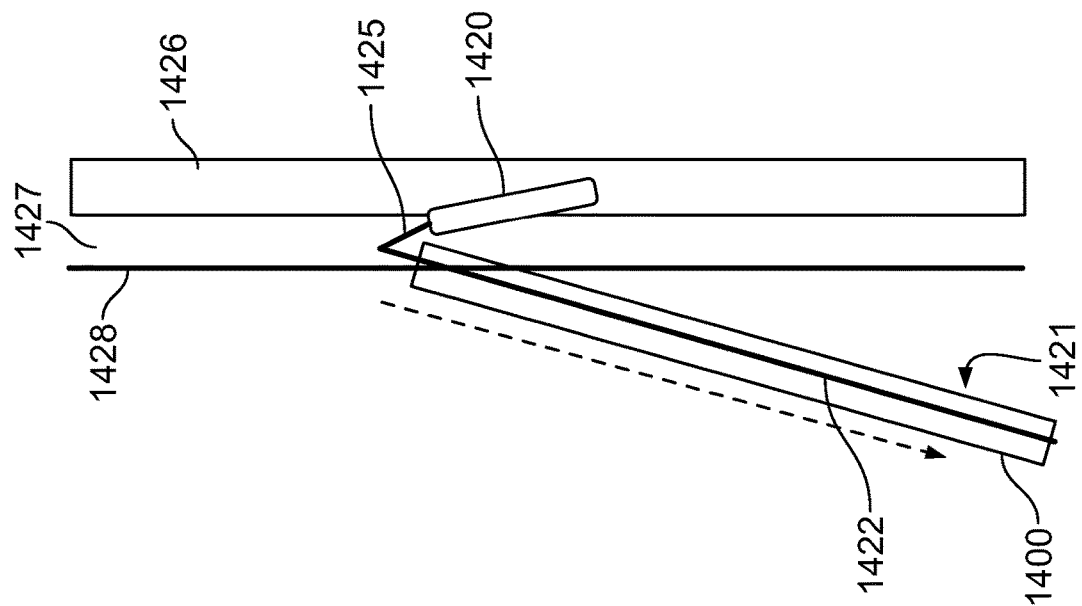
FIG. 14D is an illustration of the same embodiment of an exemplary configuration of an implantation catheter of FIG. 14A, depicting the step of the catheter being pulled away after releasing the microdevice at the tissue site.

FIG. 13B is an illustration of the same embodiment of an exemplary configuration of an implantation catheter 1300 in 13A, depicting the microdevice 1310 being pushed out of said catheter 1300 using the pusher 1312. During operation, as shown in FIG. 13B, the pusher 1312 begins to push the microdevice 1310 through the opening 1325 of the catheter deep into tissue. FIG. 13C is an illustration of the same embodiment of an exemplary configuration of an implantation catheter 1300 in 13A, depicting the microdevice 1310 fully pushed out of said catheter 1300. When the microdevice 1310 is fully pushed out of the sheath 1311, the bent portion 1320 springs outward (as a result of the recoil action due to the flexible bend) into a less acute angle, thereby separating the device 1310 from the sheath 1311. FIG. 13D is an illustration of the same embodiment of an exemplary configuration of an implantation catheter 1300 in 13A, depicting the pusher 1312 being pulled back into said catheter 1300. The pusher 1312 is pulled back into the sheath 1311, straightening the bent portion 1320 and consequently nudging the device 1310 deeper into the tissue. FIG. 13E is an illustration of the same embodiment of an exemplary configuration of an implantation catheter 1300 in 13A, depicting the pusher 1312 pulled back completely into said catheter 1300. Pulling the pusher 1312 completely into the sheath 1311 disconnects the device 1310 from the pusher 1312, thus releasing the device 1310 in the tissue site. FIGS. 14A through 14D are illustrations of the steps used for implantation of the microdevice 1420 into tissue such as mucosa 1428, submucosa 1427, and muscularis propria 1426. FIG. 14A is an illustration of one embodiment of an exemplary configuration of an implantation catheter 1400, depicting said catheter 1400 positioned near the intestinal mucosa 1428 of a patient. The catheter sheath 1421 is positioned near the mucosa 1428 of a patient. The pusher 1422 and microdevice 1420 are positioned within the sheath 1421. FIG. 14B is an illustration of the same embodiment of an exemplary configuration of an implantation catheter 1400 in 14A, depicting the step of a microdevice 1420 being pushed out of the catheter 1400 for implantation. The microdevice 1420 is pushed out of the sheath 1421 using the pusher 1422, causing the sharp edge created at the bent portion 1425 to pierce the tissue and implant the microdevice 1420. The microdevice 1420 is implanted such that one end of the microdevice 1420 is proximate the submucosa 1427 and the opposite end is proximate the muscularis propria 1426. FIG. 14C is an illustration of the same embodiment of an exemplary configuration of an implantation catheter 1400 in 14A, depicting the step of the microdevice 1420 being deployed deeper into the tissue site due to straightening of the bent portion 1425. The pusher 1422 is slowly pulled back, straightening the bent portion 1425 and deploying the device 1420 deeper into the tissue. FIG. 14D is an illustration of the same embodiment of an exemplary configuration of an implantation catheter 1400 in 14A, depicting the step of the catheter 1400 being pulled away after releasing the microdevice 1420 at the tissue site. The microdevice 1420 is released at the tissue site and the sheath 1421 is pulled away. In this embodiment, the tip can be shaped or designed with a cutting edge to facilitate with insertion. Additionally, injection of cushioning material such as saline can be used to create a larger submucosal pocket to accommodate a larger device.

Figure 15:
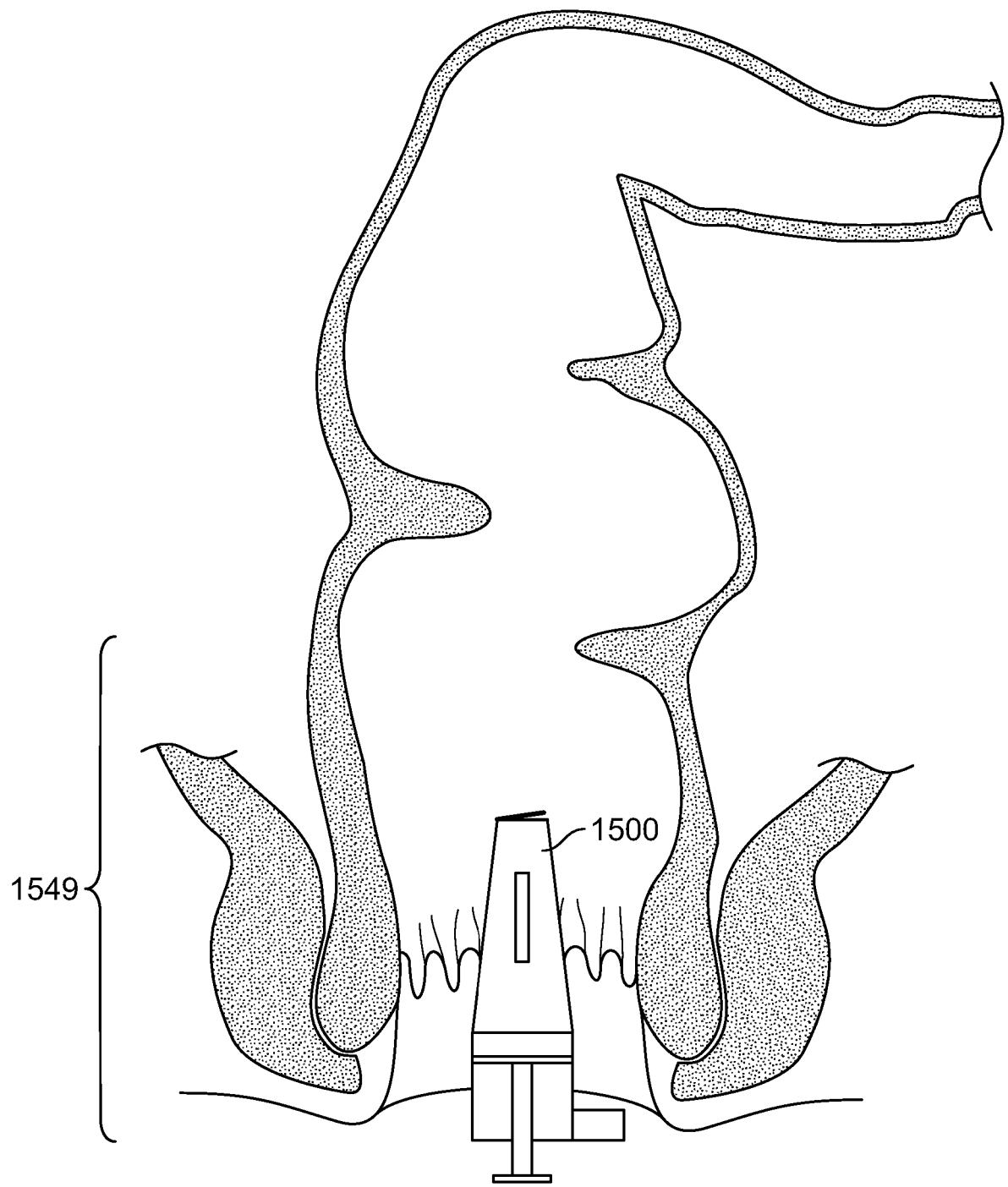
FIG. 15 is an illustration of one embodiment of an exemplary insertion device placed in the anorectal region of a patient for microdevice delivery.
Figure 16:
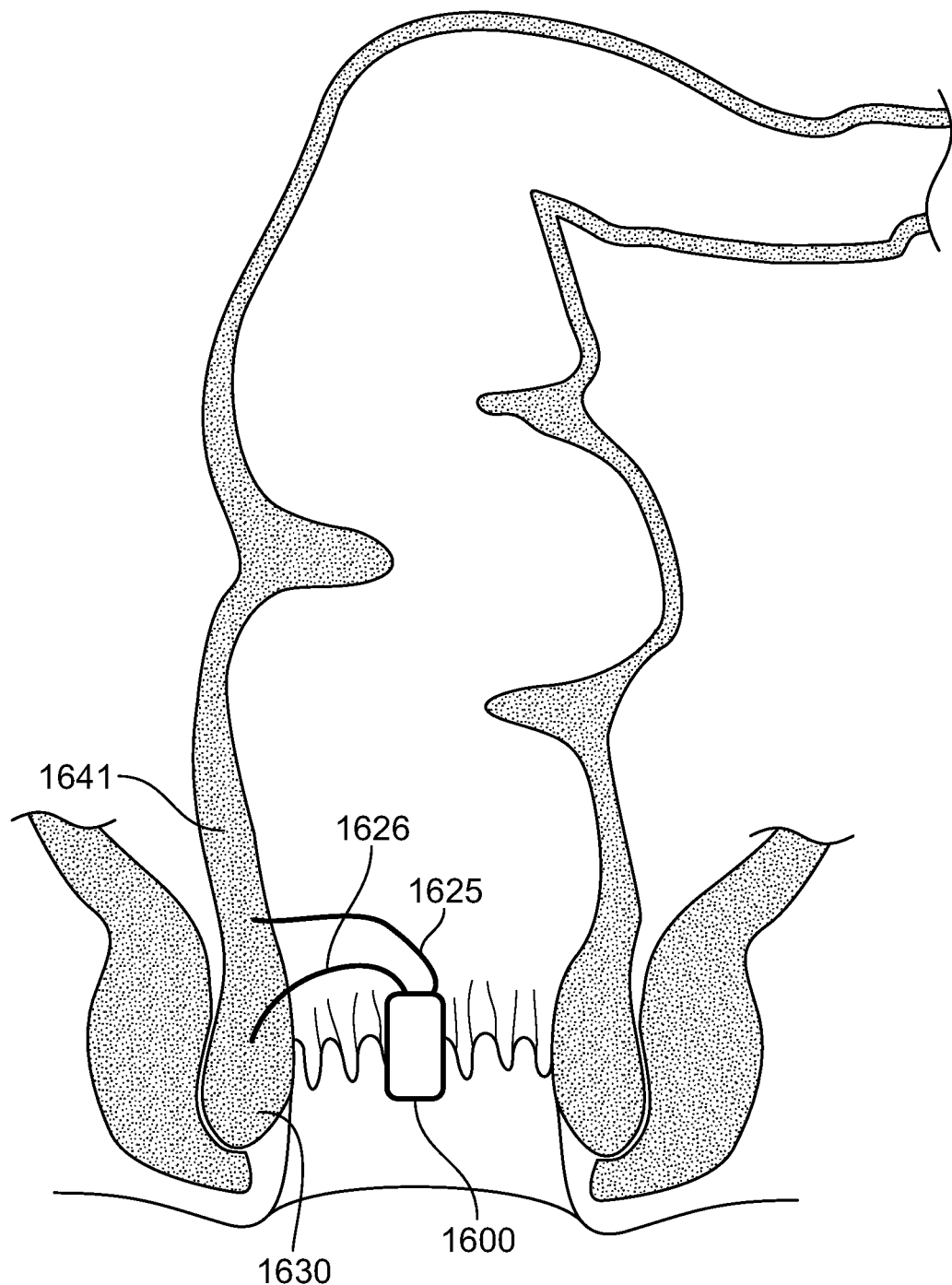
FIG. 16 is an illustration of one embodiment of a microdevice, with attached electrode set, implanted in the anorectal submucosa.

FIG. 15 is an illustration of one embodiment of an exemplary insertion device 1500 placed in the anorectal region 1549 of a patient for microdevice delivery. The insertion device 1500 is placed in the anorectal region 1549 of a patient for localization of appropriate site(s) and sucking-in tissue (as discussed with reference to FIGS. 12A through 12C). FIG. 16 is an illustration of one embodiment of a microdevice 1600 with attached electrode set 1625, 1626 implanted in the anorectal submucosa. The microdevice 1600 is implanted with a first electrode 1625 placed proximate the rectal circular muscle layer 1641 (is not circular muscle) and a second electrode 1626 placed proximate the internal anal sphincter 1630.

Figure 17:
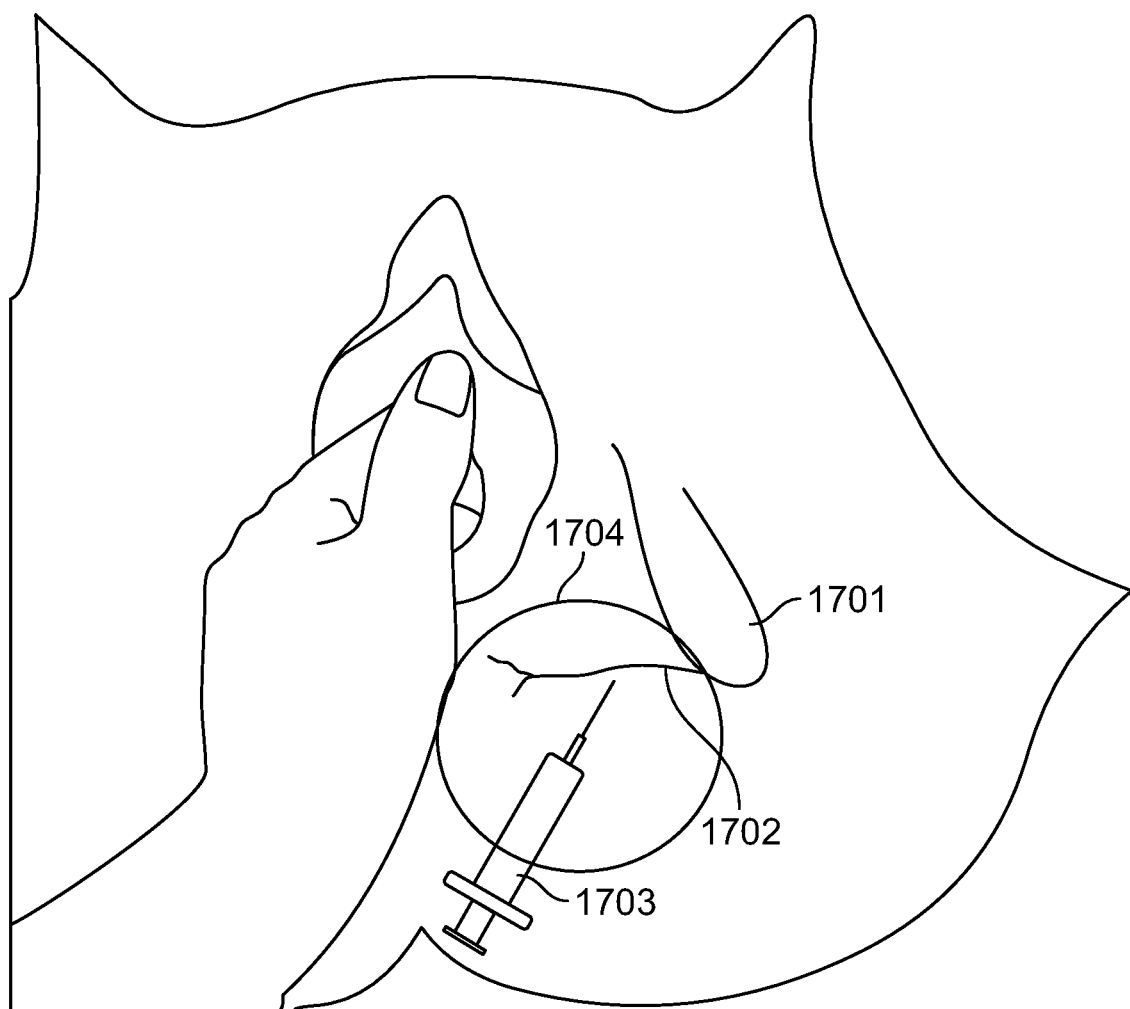
FIG. 17 is an illustration of one embodiment of the present specification depicting a method of implanting a microdevice in a female patient using a hypodermic needle.

FIG. 17 is an illustration of one embodiment of the present specification depicting a method of implanting a microdevice in a female patient using a hypodermic needle 1703. The ischial tuberosity 1701 is identified by pervaginal palpation and the microdevice is implanted percutaneously using the hypodermic needle 1703, proximate a pudendal nerve 1702. The circle 1704 depicts the preferred area for implantation of the microdevice in accordance with this embodiment.

In another embodiment, the microdevice is implanted perrectally to have one electrode of the device proximate to a pudendal nerve and the second electrode proximate an anorectal structure. The per-rectal or per vaginal implant could be further assisted by imaging such as ultrasound.

Figure 18A:
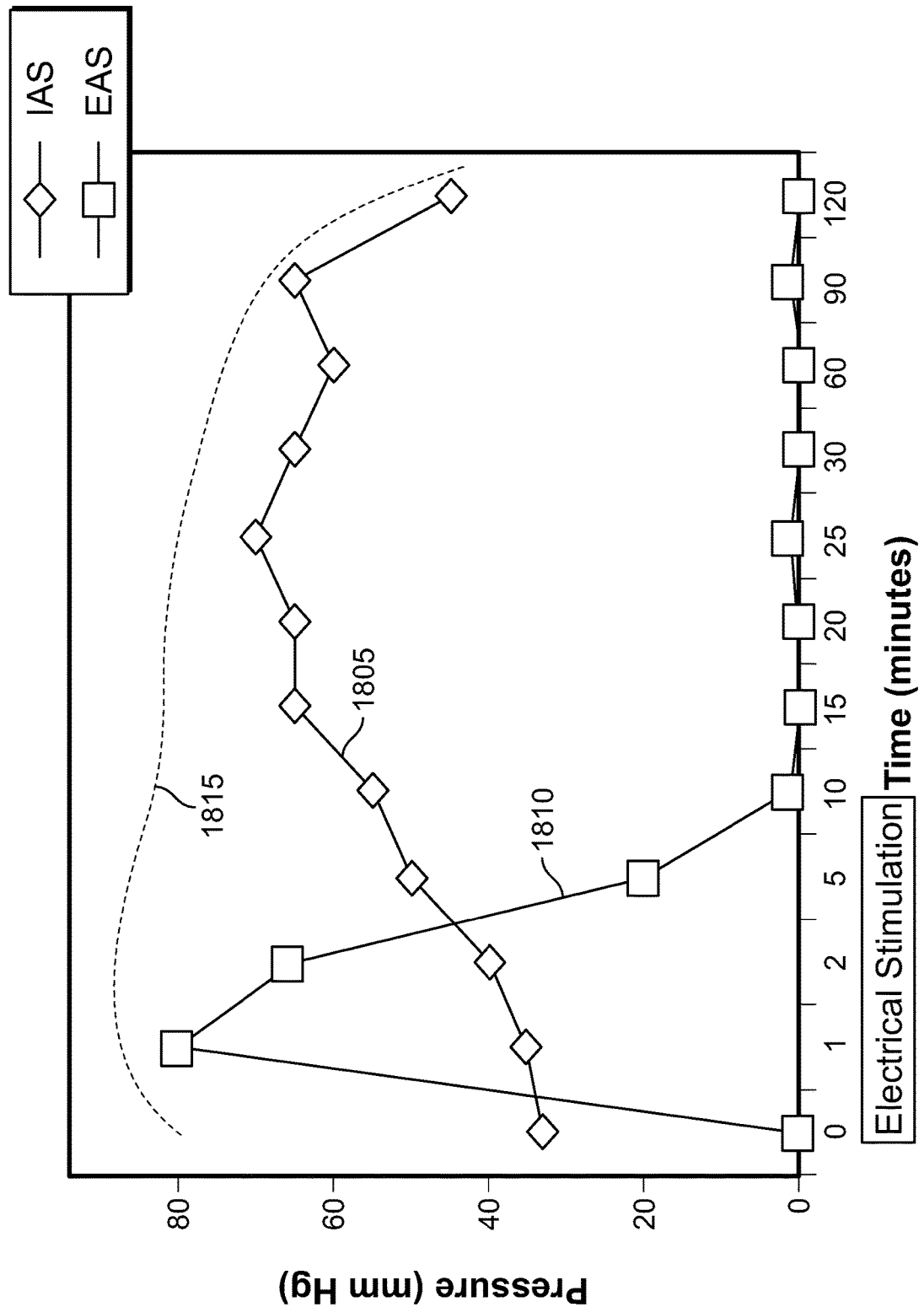
FIG. 18A is a graph depicting representative pressure curves obtained by exemplary selective stimulation of the internal anal sphincter (IAS) and external anal sphincter (EAS), in accordance with one embodiment of the present specification.

FIG. 18A is a graph depicting representative pressure curves 1805, 1810, 1815 obtained by exemplary selective stimulation of the internal anal sphincter (IAS) and external anal sphincter (EAS), in accordance with one embodiment of the present specification. Pressure curve 1805 was obtained by selective stimulation of the IAS only. The rise in IAS pressure is non-instantaneous and the improved IAS pressure exceeds the duration of electrical stimulation. Pressure curve 1810 was obtained by selective stimulation of the EAS only. The rise in EAS pressure is instantaneous and the improved EAS pressure subsides after a few minutes despite continued electrical stimulation. Pressure curve 1815 represents the cumulative pressure curve obtained by simultaneous stimulation of the IAS and EAS. The rise in the composite sphincter pressure is instantaneous and attributable predominantly to the contribution made by the EAS pressure and is sustained beyond the duration of stimulation and is attributable predominantly to the contribution made by the IAS pressure.

Figure 18B:
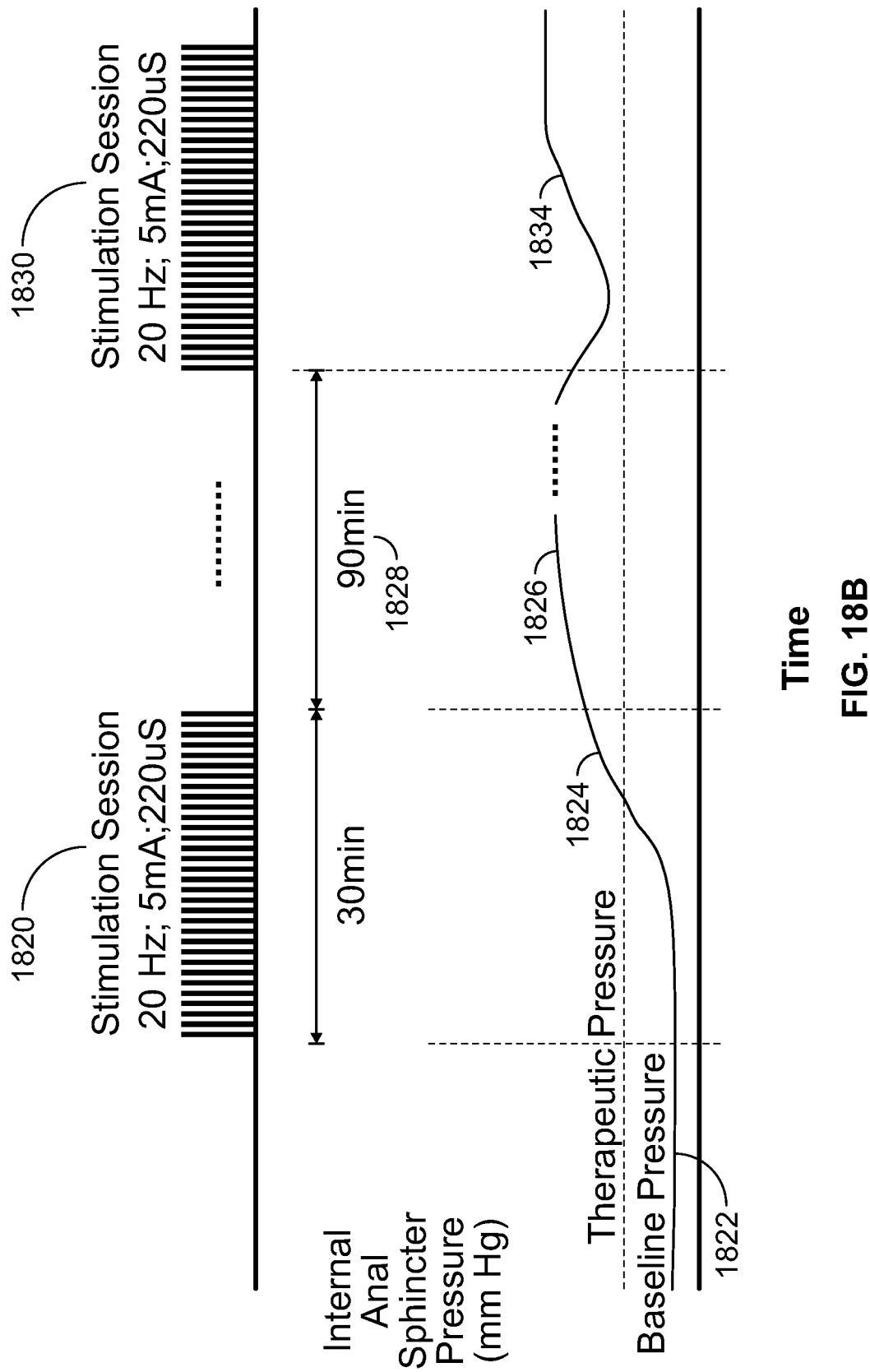
FIG. 18B is a graph depicting a rise in internal anal sphincter pressure beginning during a period of stimulation and continuing after stimulation has ceased, in accordance with one embodiment of the present specification.

FIG. 18B is a graph depicting a rise in internal anal sphincter pressure beginning during a period of stimulation and continuing after stimulation has ceased, in accordance with one embodiment of the present specification. A first stimulation period 1820 is delivered for 30 minutes. In one embodiment, the first stimulation period 1820 has a pulse frequency of 20 Hz, a pulse amplitude of 5 mA, and a pulse width of 220 μsec. The increase in internal anal sphincter pressure is delayed relative to the initiation of stimulation such that the pressure increases from a baseline pressure 1822 to a therapeutic pressure 1824 some time after stimulation has begun. Then, after the stimulation is removed, the pressure remains elevated at a maintained therapeutic pressure 1826 for an off period 1828 of 90 minutes. To prevent the pressure from returning to a level below a therapeutic pressure, a second 30 minute stimulation session 1830 is initiated at the end of the 90 minute off period 1828. In one embodiment, the second stimulation period 1820 has a pulse frequency of 20 Hz, a pulse amplitude of 5 mA, and a pulse width of 220 μsec. Electrical stimulation provided during the second stimulation period 1830 maintains the pressure at a therapeutic pressure level 1834. In some embodiments, a continuous cycle of on and off stimulation sessions is used to maintain a therapeutic internal anal sphincter pressure.

Figure 19C:
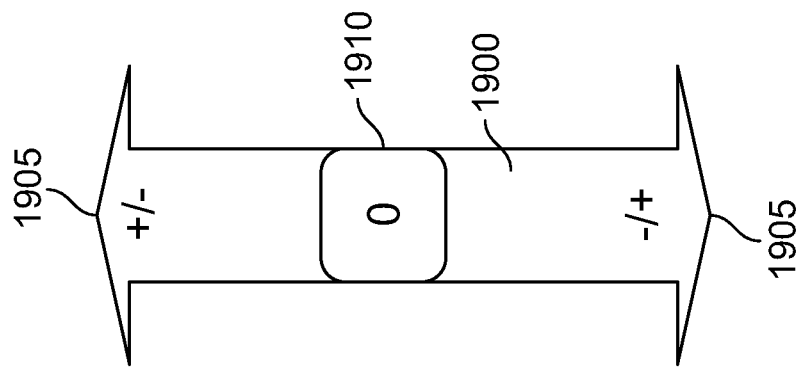
FIG. 19C is an illustration of one embodiment of a microdevice with end electrodes comprising an anode and a cathode and the center electrode comprising no polarity.
Figure 19B:
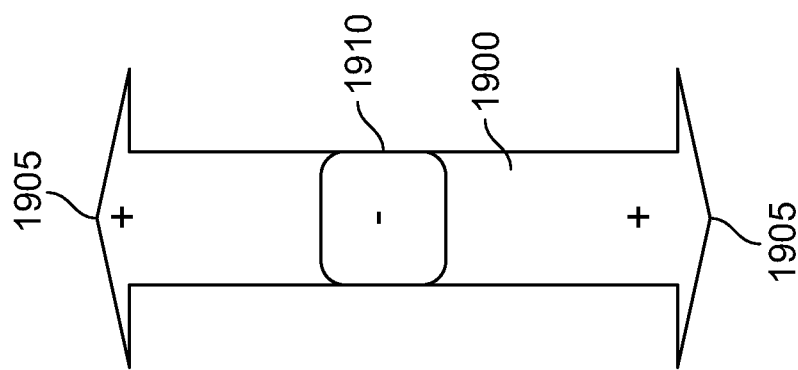
FIG. 19B is an illustration of one embodiment of a microdevice with end electrodes comprising cathodes and the center electrode comprising an anode.
Figure 19A:
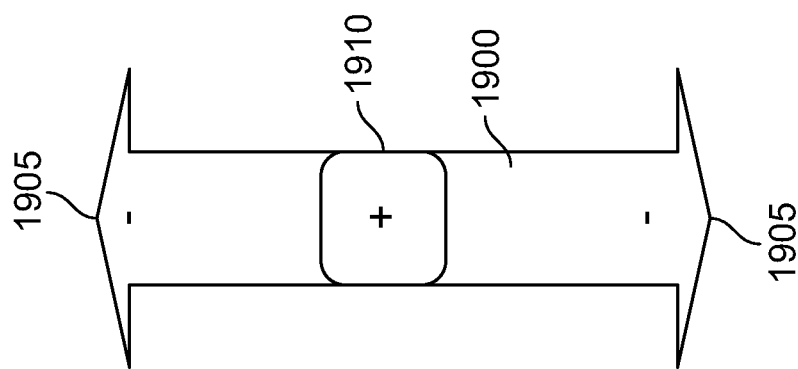
FIG. 19A is an illustration of one embodiment of a microdevice with end electrodes comprising anodes and the center electrode comprising a cathode.

FIGS. 19A through 19C depict further embodiments of the microdevice. FIG. 19A is an illustration of one embodiment of the microdevice 1900 with end electrodes 1905 as anodes and center electrode 1910 as cathode. FIG. 19B is an illustration of another embodiment of the microdevice 1900 with end electrodes 1905 as cathodes and center electrode 1910 as anode. FIG. 19C is an illustration of yet another embodiment of the microdevice 1900 with end electrodes 1905 as anode and cathode and center electrode 1910 with no polarity. The microdevice 1900 comprises three electrodes such that each pair of electrodes can be individually controlled to stimulate different anatomical structures using the same or different stimulation algorithms.

In one embodiment, a single microdevice is implanted into two contiguous anatomical structures (such as two proximate nerves or two proximate muscles or into a proximate nerve and muscle structure) with one electrode each in the two contiguous structures. Thereafter, the two contiguous structures are selectively stimulated, simultaneously or at separate times, by using the structure specific electrode, stimulation pulse patterns, waveforms, or algorithms. For example, the microdevice can be implanted proximate to a nerve and a muscle and a long-pulse (1 msec-1 sec) is used to stimulate the muscle structure while a short pulse (10 uSec-999 msec) is used to stimulate the nerve structure thus getting the benefits of both nerve and muscle stimulation from one microdevice implant. In another embodiment the electrode proximate to the desired structure could be used as a depolarizing electrode and electrode proximate to the other structure as the hyperpolarizing electrode to selectively stimulate the first structure.

In another embodiment the microdevice is implanted proximate a nerve structure comprising both afferent sensory and efferent motor nerves. At different times, based on patient input or a physiological sensory input, the single microdevice can stimulate the motor nerves using a low frequency (<100 Hz) and inhibit the sensory nerves using a high frequency (>100 Hz) or vice-versa depending on the desired physiological outcome. This will resulting in increasing the tone of the sphincter muscle while simultaneously blocking an urge sensation from the rectum. In another embodiment, the microdevice is implanted with one electrode each in a submucosal space and a muscle structure. The submucosal nerves are stimulated using a short pulse (<1 msec) and the muscle using a long pulse (≥1 mSec). Alternating between submucosal nerve stimulation and direct muscle stimulation eliminates the problem of tolerance or fatigue by continuous stimulation of only nerve or only muscle.

In one example, the microdevice is implanted with each end electrode in an internal and an external anal sphincter wherein the internal anal sphincter is stimulated using a more continuous stimulation pulse pattern or algorithm to maintain a continuous basal tone to prevent anal seepage while the external anal sphincter is stimulated more on-demand to prevent untimely defecation. In addition the internal anal sphincter is stimulated with a short-pulse to stimulate the nerves in or proximate the internal anal sphincter and the external anal sphincter is stimulated with a long-pulse to achieve direct muscle stimulation or vice-versa. The frequency of the pulse can also be varied to differentially stimulate nerves or muscles or to block the sensation being transmitted through a nerve.

In another embodiment of the present specification, the microdevice is implanted in the rectal submucosa with one electrode proximate the submucosal nerve plexus and the other electrode proximate the myenteric nerve plexus. The myenteric nerve plexus is stimulated with a low frequency pulse pattern or algorithm to stimulate the myenteric nerves whereas the submucosal plexus is stimulated with a high-frequency pulse pattern or algorithm to block the submucosal plexus or vice-versa. In another embodiment the two plexuses are stimulated with the same pattern or algorithm of pulses at different times to achieve a desired physiological effect.

In another embodiment, the microdevice is implanted in the anorectal wall with one electrode proximate the anorectal nerve plexus and the other electrode proximate a branch of the pudendal nerve or the sacral nerve. The anorectal nerve plexuses are stimulated in a more continuous fashion to maintain basal internal anal sphincter tone while the pudendal or the sacral nerves are stimulated in a more on demand fashion to generate external anal sphincter squeeze pressures to abort or prevent untimely defecation.

In another embodiment, the microdevice is implanted along the length of the pudendal or sacral nerve where the proximate pair of electrodes delivers a high-frequency blocking pulse to block the sensory afferent sensation to the brain and the distal pair of the electrode delivers a low-frequency stimulating pulse to stimulate one or both of the internal and external anal sphincters to maintain basal resting tone and/or generate squeeze pressures.

In another embodiment, the microdevice is implanted along the length of the pudendal or sacral nerve where the proximate pair of electrodes delivers a low-frequency stimulating pulse to stimulate the sensory afferent sensation to the brain and the distal pair of the electrode delivers a high-frequency blocking pulse to block one or both of the internal and external anal sphincters to eliminate the basal resting tone and/or eliminate the squeeze pressures thus initiating a bowel movement in a patient with defecatory disorders such as constipation.

In another embodiment, the microdevice is implanted with each end electrode in a deep part and a superficial part of the external anal sphincter wherein the two parts of the external anal sphincter are stimulated alternately, allowing one part to rest while the other is stimulated, hence increasing the duration of the squeeze pressure without the problem of tolerance or muscle fatigue. In addition, the two parts of the external anal sphincter can be stimulated alternately with a short-pulse to stimulate the nerves in or proximate the external anal sphincter and with a long-pulse to achieve direct external anal muscle stimulation, hence further increasing the duration of the squeeze pressure without the problem of tolerance or muscle fatigue.

In another embodiment, the microdevice is implanted with an electrode each in the inner circular muscle layer of the distal rectum and the internal anal sphincter wherein the two structures are simultaneously stimulated. This configuration allows both physiological structures to contract synchronously and synergistically increasing the length of the high pressure zone at the rectal outlet effectively increasing the functional length of the anal sphincter. This results in an increased effective competence of the sphincter even at the lower range of sphincter pressure. This embodiment allows maintaining sphincter competence even at low levels of electrical stimulation and hence decreasing the problem of tolerance or muscle fatigue which is usually observed at higher levels of electrical stimulation. In addition, the circular muscle of the rectum is enabled to work as a high pressure zone and a functional sphincter, thus maintaining continence in patients with a damaged sphincter such as those of women with traumatic delivery resulting in perineal tear and anal sphincter damage.

In another embodiment, the microdevice is implanted with an electrode each in the inner circular muscle layer of the distal rectum and the internal anal sphincter wherein the two structures are sequentially stimulated. This allows for the rectum to contract and the anal canal to relax resulting in defecation. This configuration enables treatment of outlet type constipation due to dyssynergic sphincter dysfunction.

Figure 20:
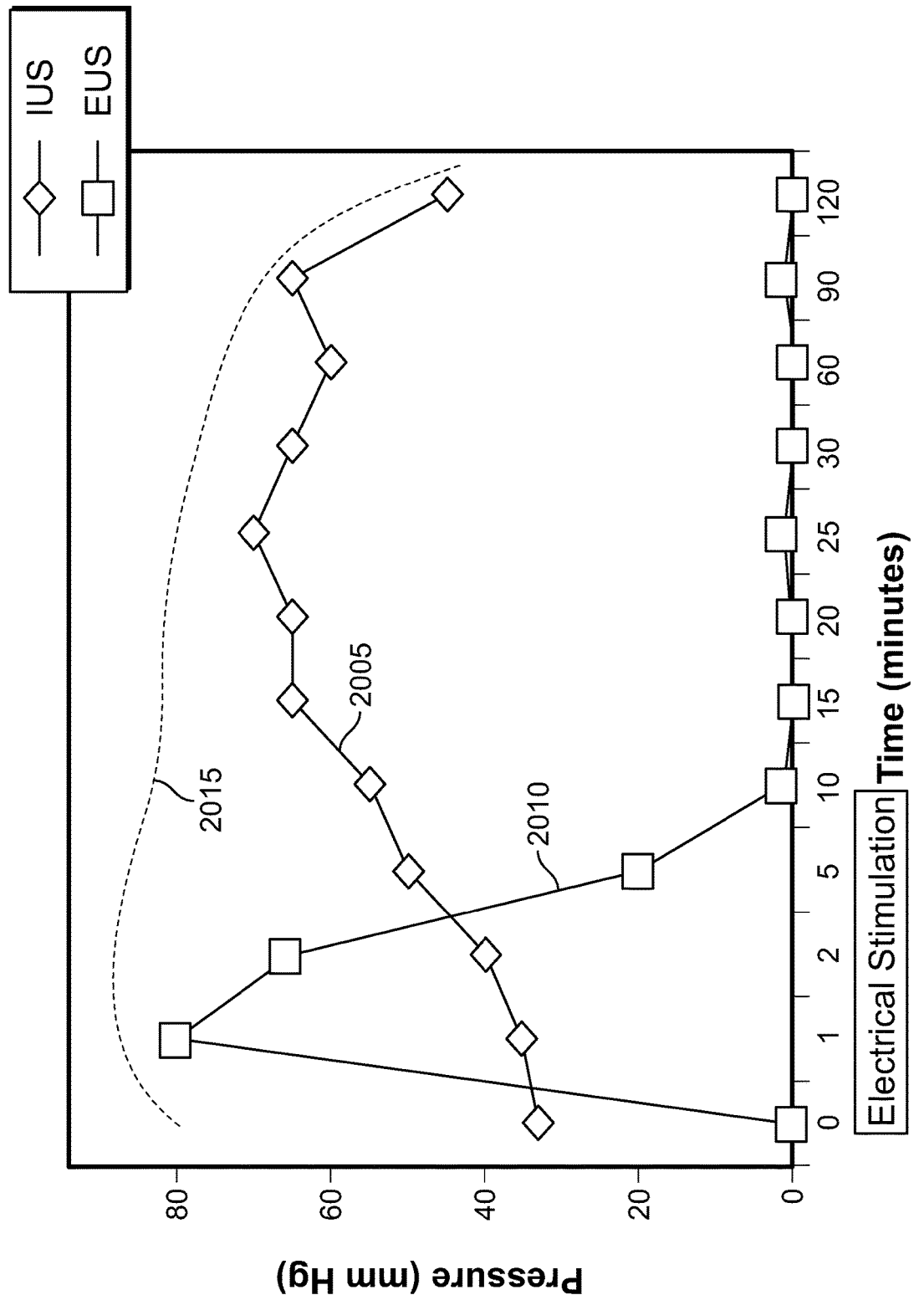
FIG. 20 is a graph depicting representative pressure curves obtained by exemplary selective stimulation of the internal urinary sphincter (IUS) and external urinary sphincter (EUS), in accordance with one embodiment of the present specification.

FIG. 20 is a graph depicting representative pressure curves 2005, 2010, 2015 obtained by exemplary selective stimulation of the internal urinary sphincter (IUS) and external urinary sphincter (EUS), in accordance with one embodiment of the present specification. Pressure curve 2005 was obtained by selective stimulation of the IUS only. The rise in IUS pressure is non-instantaneous and the improved IUS pressure exceeds the duration of electrical stimulation. Pressure curve 2010 was obtained by selective stimulation of the EUS only. The rise in EUS pressure is instantaneous and the improved EUS pressure subsides after a few minutes despite continued electrical stimulation. Pressure curve 2015 represents the cumulative pressure curve obtained by simultaneous stimulation of the IUS and EUS. The rise in the composite sphincter pressure is instantaneous and attributable predominantly to the contribution made by the EUS pressure and is sustained beyond the duration of stimulation and is attributable predominantly to the contribution made by the IUS pressure.

Urinary Dysfunction Therapeutic Endpoints

In various embodiments, the systems and methods of the present specification are configured to produce results consistent with the following urinary dysfunction therapeutic endpoints, particularly with regards to urinary incontinence. It should be appreciated that said configuration is achieved by modulating the various stimulation parameters, such as pulse frequency, pulse width, pulse shape, and pulse amplitude, for each individual patient until the therapeutic objectives disclosed herein are achieved. Furthermore, it should be appreciated that a specific endpoint is determined to have increased by X % or decreased by X % by calculating the difference between its newly measured amount (typically after a stimulation session) and its prior amount (typically before that stimulation session) and dividing that difference by the prior amount.

In various embodiments, treatment of urinary incontinence in a patient using the systems and methods of the present specification results in an increase in abdominal leak point pressure on urodynamic stress testing by at least 5% or at least 60 cm $H_2O$ compared to pretreatment values.

In various embodiments, treatment of urinary incontinence in a patient using the systems and methods of the present specification results in an increase in abdominal leak point volume on urodynamic stress testing by at least 5% or at least 50 cc compared to pretreatment values. In various embodiments, treatment of urinary incontinence in a patient using the systems and methods of the present specification results in an increase in cystometry on urodynamic stress testing by at least 5% compared to pretreatment values.

Cystometry is a technique of assessing the filling phase of bladder function. Much information can be gained during cystometry, including the diagnosis of bladder overactivity, bladder oversensitivity, sensory neuropathy, loss of compliance, and determination of bladder capacities.

The 4 recognized cystometric phases of bladder function are:

1. An initial small increase in intravesical pressure at the beginning of filling;
2. A stable pressure that comprises the majority of the filling phase;
3. A terminal pressure rise at bladder capacity, representing the limit of viscoelastic expansion (often not reached due to discomfort); and
4. A voiding phase with an inconsistently observed small increase in intravesical pressure.

Single channel cystometry consists of recording isolated intravesical pressures during filling with a single catheter. Multichannel cystometry is performed with a bladder catheter and a second catheter to approximate intraabdominal pressure. The second catheter is usually placed in the rectum, or at times in the vagina. The data output consists of a vesicle pressure channel, an abdominal pressure channel, and true detrusor pressure channel. The true detrusor pressure channel, also called the subtracted channel, is the bladder pressure minus the abdominal pressure. Depending on the individual set up, additional channels may accommodate simultaneous urethral pressure readings and continuous electromyography (EMG) readings. A liquid medium, usually saline, is preferred. Most testing is performed with room temperature solutions. The filling rate can vary and usually ranges from 10-100 ml per minute. Slower, more physiologic rates can be used if a suspected false-positive result is obtained at faster rates. Likewise, faster rates can be used to provoke subtle instability or can be used in patients with significant urgency who do not allow sufficient volumes to be infused at slower rates and longer infusion times.

In various embodiments, treatment of urinary incontinence in a patient using the systems and methods of the present specification results in an increase in abdominal (or Valsalva) leak point pressure on urodynamic stress testing by at least 5% compared to pretreatment values. The Valsalva leak-point pressure, or abdominal leak-point pressure (ALPP), is a test of the urethral sphincter resistance against increases in intraabdominal pressure. The overall assumption is that the lower the leak point pressure, the weaker the urethral sphincter and the more severe the stress incontinence. For the basic abdominal leak-point pressure test, intravesical and intra-rectal catheters are placed and the bladder is filled with 150-250 ml of fluid. The patient, who is in either the sitting or standing position, is asked to perform a Valsalva maneuver of slowly building intensity. The lowest pressure at which leakage from the urethral meatus is observed denotes the leak point pressure. If no leakage is produced or the patient is unable to perform the Valsalva maneuver properly, a cough leak-point pressure can be attempted. Leak point pressures below 60 cm water define intrinsic sphincter deficiency. The cough stress test can be performed with the bladder empty or with the patient's bladder filled up to 300 ml or to subjective fullness and then, while in an upright or lithotomy position, having the patient perform a series of forceful coughs.

In various embodiments, treatment of urinary incontinence in a patient using the systems and methods of the present specification results in an increase in post void residual urine volume determination on urodynamic stress testing by at least 5% compared to pretreatment values.

In various embodiments, treatment of urinary incontinence in a patient using the systems and methods of the present specification results in uroflowmetry on urodynamic stress testing by at least 5% compared to pretreatment values.

In various embodiments, treatment of urinary incontinence in a patient using the systems and methods of the present specification results in an increase in bladder compliance on urodynamic stress testing by at least 5% or at least 20 ml/cm $H_2O$ compared to pretreatment values.

In various embodiments, treatment of urinary incontinence in a patient using the systems and methods of the present specification results in an increase in detrusor leak point pressure (DLPP) on urodynamic stress testing by at least 5% or at least 40 cm $H_2O$ compared to pretreatment values.

In various embodiments, treatment of urinary incontinence in a patient using the systems and methods of the present specification results in an increase in first sensation volume on urodynamic stress testing by at least 5% or at least 50 ml compared to pretreatment values. The first sensation is described as the volume at which the patient first is aware of fluid in the bladder (reference range of 50-200 ml).

In various embodiments, treatment of urinary incontinence in a patient using the systems and methods of the present specification results in an increase in second sensation (full) volume on urodynamic stress testing by at least 5% or at least 200 ml compared to pretreatment values. The second sensation (full) has been described as the volume at which the individual normally would consider voiding due to an urge sensation (reference range of 200-400 ml).

In various embodiments, treatment of urinary incontinence in a patient using the systems and methods of the present specification results in an increase in maximum capacity on urodynamic stress testing by at least 5% or at least 400 ml compared to pretreatment values. Maximum capacity is when the patient is experiencing pain and does not allow continued filling (reference range of 400-600 ml). The average bladder holds 400-500 ml of urine. Any bladder contraction during filling is considered abnormal, a minimal contraction amplitude of 15 cm $H_2O$ over baseline is considered significant.

In various embodiments, treatment of urinary incontinence in a patient using the systems and methods of the present specification results in an increase in maximum detrusor pressure on urodynamic stress testing by at least 5% or at least 20 cm $H_2O$ compared to pretreatment values.

In various embodiments, treatment of urinary incontinence in a patient using the systems and methods of the present specification results in an increase in detrusor contractility on urodynamic stress testing by at least 5% but no greater than 25% compared to pretreatment values.

With respect to the above listed effects based on measurements gathered using urodynamic stress testing, urodynamics are a means of evaluating the pressure-flow relationship between the bladder and the urethra for the purpose of defining the functional status of the lower urinary tract. Urodynamic studies assess both the filling storage phase and the voiding phase of the urinary bladder, as well as urethral function. In addition, provocative tests can be added to try to recreate symptoms and to assess pertinent characteristics of urinary leakage.

Simple urodynamic tests involve performing a noninvasive uroflow study, obtaining a postvoid residual (PVR) urine measurement, and performing single channel cystometrography (CMG). A single channel CMG (i.e. simple CMG) is used to assess the first sensation of filling, fullness, and urge. Bladder compliance and the presence of uninhibited detrusor contractions (e.g., phasic contractions) can be noted during this filling CMG. A simple CMG is generally performed using water as the fluid medium.

Multichannel urodynamic studies are more complex than simple urodynamics and can be used to obtain additional information, including a noninvasive uroflow, PVR, filling CMG, abdominal leak-point pressure (ALPP), voiding CMG (pressure-flow), and electromyography (EMG). Water is the fluid medium used for multichannel urodynamics.

The most sophisticated study is videourodynamics, the criterion standard in the evaluation of a patient with incontinence. In this study, the following are obtained: noninvasive uroflow, PVR, and filling CMG, abdominal (or Valsalva) leak point pressure, voiding CMG (pressure-flow study), EMG, static cystography, and voiding cystourethrography. The fluid medium used for videourodynamics is radiographic contrast.

For testing, a patient is instructed to arrive at the urodynamic laboratory with a full bladder. A noninvasive uroflow, postvoid residual (PVR) urine test and a standing cough stress test is performed. To perform urodynamic testing, the patient is first placed in the dorsolithotomy position. Bladder filling is commenced using room temperature water or contrast. Cold fluid may evoke false positive detrusor contractions (i.e. phasic contractions). The bladder is filled at a medium rate (e.g., 60 ml/min). The volumes at which first sensation of bladder fullness and first sensation of urge to urinate occur are noted. Bladder compliance and the change in volume per change in pressure are monitored, and the presence of uninhibited detrusor contractions is marked. Ranges for bladder compliance are from 40 ml/cm $H_2O$ to 120 ml/cm $H_2O$, while values of 10 ml/cm $H_2O$ to 20 ml/cm $H_2O$ are abnormal. When the bladder fills to 250 ml, the abdominal leak-point pressure (ALPP) is measured to investigate for stress urinary incontinence. The patient is instructed to perform the Valsalva in gradients (i.e., mild, moderate, strong) followed by cough (i.e., mild, moderate, strong). Studies have suggested an ALPP under 60 cm $H_2O$ suggests intrinsic sphincter deficiency, while that over 90 cm $H_2O$ refutes this, and values between may be seen with either. DLPP is the pressure at which urine leakage occurs in the absence of a detrusor contraction or abdominal pressure increase. This should normally be less than 40 cm $H_2O$ and if it is higher than this, the kidneys are at risk for damage secondary to backpressure.

In various embodiments, treatment of urinary incontinence in a patient using the systems and methods of the present specification results in an improvement in voiding diaries (incontinent episodes) by at least 5% compared to pretreatment values, wherein said 5% improvement is defined as a 5% reduction in the number of incontinence episodes or a 5% reduction in the mean incontinence volume per episode. The voiding diary is a record of micturition behavior completed by the patient. It is among the best possible means of obtaining objective data on subjective symptoms. There are various terms used for voiding diaries, including micturition time or frequency charts, frequency volume charts, and bladder or urinary diaries. There are a number of different types of voiding diaries, including a frequency chart, which is the simplest type of voiding diary because the patient is asked to record only micturition and incontinence episodes. A frequency-volume chart requires the patient to record the amount of urine of each micturition, the time of each void, and incontinence episodes. Other parameters include the number of pads used and estimated fluid intake in cups or mugs. Urgency may be recorded as 0, +, or ++, or on a scale from 0-10, depending on the diary used. Urgency can also be evaluated in minutes, by asking the patient to estimate how long he or she could wait before voiding.

In various embodiments, treatment of urinary incontinence in a patient using the systems and methods of the present specification results in an increase in total voided volumes by at least 5% compared to pretreatment values.

In various embodiments, treatment of urinary incontinence in a patient using the systems and methods of the present specification results in an increase mean voided volumes by at least 5% compared to pretreatment values.

In various embodiments, treatment of urinary incontinence in a patient using the systems and methods of the present specification results in an increase in largest single voided volumes by at least 5% compared to pretreatment values.

In various embodiments, treatment of urinary incontinence in a patient using the systems and methods of the present specification results in an improvement in patient incontinence perception scores (visual analog scale score 1-100) by at least 5% compared to scores in the absence of treatment. A visual analog scale (VAS) is question-based assessment mechanism, where a visual measure is associated with each question and where answering the question requires selecting a quantifiable position within that visual measure, indicative of a particular level or degree. The scale is typically composed of lines (of varying length) with words anchored at each end, describing the extremes (that is, 'I am not incontinent at all' on the left to 'I am incontinent at all times' on the right). Patients are asked to make a mark across the line corresponding to their feelings. Quantification of the measurement is done by measuring the distance from the left end of the line to the mark. In some embodiments, VAS may be used to assess the severity of fecal incontinency, urinary incontinence or a sexual dysfunction.

In various embodiments, treatment of urinary incontinence in a patient using the systems and methods of the present specification results in an improvement in Stamey's incontinence score by at least 1 grade compared to pretreatment values. Stamey's incontinence scoring system comprises the following numerical grade scores and definitions: grade 0=no incontinence; grade 1=incontinence with coughing or straining; grade 2=incontinence with change in position or walking; and grade 3=total incontinence at all times.

In various embodiments, treatment of urinary incontinence in a patient using the systems and methods of the present specification results in an increase in urogenital distress inventory (UDI) for women by at least 5% compared to pretreatment values.

In various embodiments, treatment of urinary incontinence in a patient using the systems and methods of the present specification results in an increase in severity index for urinary incontinence in women by at least 5% or an improvement by at least 1 point compared to pretreatment values. The severity index for urinary incontinence in women comprises two parameters associated with findings which are then attributed a numerical point score. The point score of the first parameter finding is then multiplied by the point score of the second parameter finding to provide a severity index wherein a greater score indicates more severe incontinence. A first parameter asks the patient how often urine leakage is experienced, with the following findings and corresponding point scores: never=0; less than once a month=1; one to several times a month=2; one to several times a week=3; and every day and/or night=4. A second parameter asks the patient how much urine is lost each time, with the following findings and corresponding point scores: a few drops=1; a little=2; and more=3. The resultant severity index is defined by the following point scores: 1-2=slight; 3-6=moderate; 8-9=severe; and 12=very severe.

In various embodiments, treatment of urinary incontinence in a patient using the systems and methods of the present specification results in an increase in leakage index for women with stress incontinence by at least 5% compared to pretreatment values.

In various embodiments, treatment of urinary incontinence in a patient using the systems and methods of the present specification results in an improvement in pad testing (1 hour and 24 hour) results by at least 5% compared to pad testing in the absence of treatment, wherein a 5% improvement is defined as a 5% reduction in urine volume measured by weight gain of absorbent pads. Pad testing denotes a validated methodology to quantify urine loss by measuring the weight gain of absorbent pads during a test period. Pad testing can quantify urine loss. Short-term (<1, 1, 2 h) and long-term (24 h and longer) tests have been used. Short-term tests are done in the office setting while longer tests are done by the patient in her daily environment.

In various embodiments, treatment of urinary incontinence in a patient using the systems and methods of the present specification results in an increase in quality of life (SF6, SF12, Roger Goldberg scales) by at least 5% compared to pretreatment values. Health-related quality of life (HRQOL) is a composite health care outcome implying several subsets of function, often categorized into physical well-being, social function, mental health, societal role, and general health perception. HRQOL instruments are typically comprised of numerous patient completed questions, or items, arranged into several domains. SF-36 is the most common general HRQOL instrument, a self-administered tool organizing HRQOL into eight scales addressing physical function, social function, pain, emotional well-being, energy, general health perceptions, and role limitation due to physical and/or emotional problems.

Sexual Dysfunction Therapeutic Endpoints

In various embodiments, the systems and methods of the present specification are configured to produce results consistent with the following sexual dysfunction therapeutic endpoints. It should be appreciated that said configuration is achieved by modulating the various stimulation parameters, such as pulse frequency, pulse width, pulse shape, and pulse amplitude, for each individual patient until the therapeutic objectives disclosed herein are achieved. Furthermore, it should be appreciated that a specific endpoint is determined to have increased by X % or decreased by X % by calculating the difference between its newly measured amount (typically after a stimulation session) and its prior amount (typically before that stimulation session) and dividing that difference by the prior amount.

In various embodiments, treatment of sexual dysfunction in a patient using the systems and methods of the present specification results in an improvement in Golombok Rust Inventory of Sexual Satisfaction (GRISS) scores by at least 5% compared to pretreatment scores. The Golombok Rust Inventory of Sexual Satisfaction (GRISS) is a measure of sexual dysfunction which may be administered to heterosexual couples or individuals who have a current heterosexual relationship. It provides overall scores, for men and women separately, of the quality of sexual functioning within a relationship. In addition subscale scores of impotence, premature ejaculation, anorgasmia, vaginismus, infrequency, noncommunication, male dissatisfaction, female dissatisfaction, male nonsensuality, female nonsensuality, male avoidance, and female avoidance can be obtained and represented as a profile. A combination of norm referencing and criterion referencing yielded transformed scales that give a good indication of the existence and severity of any problems. Transformations are to a pseudo-stannine scale (area based, from 1 to 9) with a score of 5 or above indicating a problem.

In various embodiments, treatment of sexual dysfunction in a patient using the systems and methods of the present specification results in an improvement in International Index of Erectile Function (IIEF) scores by at least 5% compared to pretreatment scores.

In various embodiments, treatment of sexual dysfunction in a patient using the systems and methods of the present specification results in an improvement in quality of life (SF6, SF12) by at least 5% compared to pretreatment values. Quality of life is measured similarly as with urinary incontinence as described above.

In various embodiments, treatment of sexual dysfunction in a patient using the systems and methods of the present specification results in an improvement in patient perception score (visual analog scale score 1-100) by at least 5% compared to pretreatment scores. VAS is measured similarly as with urinary incontinence as described above.

In various embodiments, treatment of sexual dysfunction in a patient using the systems and methods of the present specification results in an improvement in sexual function questionnaire scores by at least 5% compared to pretreatment scores.

In various embodiments, treatment of sexual dysfunction in a patient using the systems and methods of the present specification results in an improvement in Sexual Dysfunction Questionnaire (SDQ) scores by at least 5% compared to pretreatment scores or an SDQ score of less than 45. Sexual Dysfunction Questionnaire (SDQ) is a 19-item questionnaire based on sexual experiences from the previous 12 months. The critical value (cut-off) was established at a score of 45 (corresponding to a probability of 0.5 of being in the dysfunctional group), above which the subject has characteristics of sexuality problems, of growing importance, thus increasing the score. FIG. 21 is a table for a Sexual Dysfunction Questionnaire (SDQ) listing a series of statements about a patient's sexuality 2102 with scores 2104 ranging from 1 to 5 wherein 1 indicates always and 5 indicates never.

In various embodiments, treatment of sexual dysfunction in a patient using the systems and methods of the present specification results in an improvement in a female sexual function index by at least 5% compared to pretreatment scores.

In various embodiments, treatment of sexual dysfunction in a patient using the systems and methods of the present specification results in an increase in sexual desire as measured in a patient daily diary by at least 5% compared to pretreatment values.

In various embodiments, treatment of sexual dysfunction in a patient using the systems and methods of the present specification results in an increase in the number of successful or satisfactory sexual events or encounters over time as measured in a patient daily diary by at least 5% compared to pretreatment values. Event logs or diary measures may provide sensitive and reliable measures of efficacy in studies of erectile dysfunction or premature ejaculation in men, or in other therapeutic areas with discrete and observable endpoints. These endpoints are based on the number of successful and satisfactory sexual events or encounters over time. The determination of successful and satisfactory are made by the woman participating, as opposed to her partner. Additional endpoints such as desire, arousal, orgasm or pain can also be studied using this tool. Furthermore, severity and frequency of these endpoints can be recorded. A count of these endpoints gives an objective measure of sexual dysfunction and a change in sexual dysfunction with an intervention.

In various embodiments, treatment of sexual dysfunction in a patient using the systems and methods of the present specification results in an increase in a brief index of sexual functioning by at least 5% compared to pretreatment values.

The PROMIS Sexual Function and Satisfaction Measures Brief Profile (PSxFBP) provides scores on 6 different subdomains of sexual function: Interest in Sexual Activity, Vaginal Discomfort (women only), Lubrication (women only), Erectile Function (men only), Orgasm, and Global Satisfaction with Sex Life.

After confirming all items in a given domain were answered without endorsing a "not applicable" response (identified by a score of 0), the response scores are summed to all items in that domain to provide a raw summed score for that domain. For example, for Global Satisfaction with Sex Life, the raw summed score can range from 2 (endorsed "Not at all" to both items) to 10 (endorsed "Very" or "Very much" to both items). For the single Orgasm item, no summed score is produced. This item is not scored using item response theory. Instead, raw responses can be used in analyses.

A T-score rescales the raw score into a standardized score with a mean of 50 and a standard deviation (SD) of 10. Therefore, a person with a T-score of 40 is one SD below the mean. The standardized T-score is reported as the final score for each participant for each domain. For example, for the Global Satisfaction with Sex Life domain, a raw summed score of 6 converts to a T-score of 48.15 with a standard error (SE) of 3.52. Thus, the 95% confidence interval around the observed score ranges from 41.25 to 55.04 (T-score+ (1.96*SE) or 48.15+(1.96*3.52).

Patients with irritable bowel syndrome commonly suffer from alternating constipation and diarrhea with symptoms of fecal urgency. In one embodiment, the electro-medical device of the present specification allows the patient to control the respective symptoms using different electrode combinations and different stimulation algorithms, as described above.

Fecal Incontinence Therapeutic Endpoints

In various embodiments, the systems and methods of the present specification are configured to produce results consistent with the following fecal dysfunction therapeutic endpoints, particularly with regards to fecal incontinence. It should be appreciated that said configuration is achieved by modulating various stimulation parameters, such as pulse frequency, pulse width, pulse shape, and pulse amplitude, for each individual patient until the therapeutic objectives disclosed herein are achieved. Furthermore, it should be appreciated that a specific endpoint is determined to have increased by X % or decreased by X %, by calculating the difference between its newly measured amount (typically after a stimulation session) and its prior amount (typically before that stimulation session) and dividing that difference by the prior amount.

FIG. 22 is a table summarizing the improvements achieved in the treatment of fecal incontinence in patients using the systems and methods of the present specification.

It may be noted that improvement may imply either an increase or decrease in the measured variable. Referring to FIG. 22, in various embodiments, treatment of fecal incontinence in a patient using the systems and methods of the present specification results in an improvement in patient incontinence perception scores (visual analog scale score 1-100) by at least 5% compared to scores in the absence of treatment, shown as 2201. As mentioned earlier with reference to urinary dysfunction, a visual analog scale (VAS) is a question-based assessment mechanism, where a visual measure is associated with each question and where answering the question requires selecting a quantifiable position within that visual measure, indicative of a particular level or degree. The scale is typically composed of lines (of varying length) with words anchored at each end, describing the extremes (that is, 'I am not incontinent at all' on the left to 'I am incontinent at all times' on the right). Patients are asked to make a mark across the line corresponding to their feelings. Quantification of the measurement is done by measuring the distance from the left end of the line to the mark. In some embodiments, VAS may be used to assess the severity of fecal incontinency, urinary incontinence or a sexual dysfunction.

In various embodiments, treatment of fecal incontinence in a patient using the systems and methods of the present specification results in an improvement on the Rothenberger incontinence scale by at least 5% compared to pretreatment values, as shown as 2202. In various embodiments, treatment of fecal incontinence in a patient using the systems and methods of the present specification results in an improvement on the Wexner incontinence scale by at least 5% compared to pretreatment values, as shown as 2203. In various embodiments, treatment of fecal incontinence in a patient using the systems and methods of the present specification results in an improvement on the Vaizey incontinence scale by at least 5% compared to pretreatment values, as shown as 2204.

In various embodiments, treatment of fecal incontinence in a patient using the systems and methods of the present specification results in an increase in severity index for fecal incontinence (FISI=Fecal Incontinence Severity Index) in patients by at least 5% compared to pretreatment values, as shown as 2205. The severity index for fecal incontinence in patients comprises several parameters associated with findings which are then attributed a numerical point score.

It may be noted that Rothenberger, Wexner, Vaizey and FISI are various incontinence scoring systems that provide a measure of a patient's fecal incontinence level by taking into account factors such as frequency of fecal incontinence, type of fecal incontinence and components impacting incidence of fecal incontinence. FIGS. 23A and 23B illustrate the methodology of various scoring systems. Referring to FIG. 23A, the various fecal incontinence indices 2300 consider frequency of incontinence 2301, which may range for example, from less than 1 per month to more than 2 per day. The indices also consider the type of fecal matter 2302 for the purpose of incontinence, such as solid, liquid, gas and mucous. The indices also consider the other factors impacting incontinence 2303, such as pad usage and lifestyle alteration.

FIG. 23B illustrates the scoring methodology of various indices. Referring to FIG. 23B, the scores 2310 for fecal incontinence range from 0-30 for Rothenberger, 0-20 for Wexner, 0-24 for Vaizey and 0-61 for FISI. Further, different scoring systems also accord varying weights 2312 to different types of incontinence, such as solid, liquid and gas incontinence and to impacting factors such as lifestyle alteration.

In various embodiments, treatment of fecal incontinence in a patient using the systems and methods of the present specification results in an improvement of at least 5% compared to pretreatment values in parameters measured by anorectal manometry. Anorectal manometry is a test involving placement of a rectal balloon in the patient. Typically, the rectal balloon is filled with 50 cc of warm water and various anal and rectal parameters are measured as the balloon is expelled by the patient while seated in privacy on a commode. The time required for subjects to expel a rectal balloon forms the basis of rectal balloon expulsion test. In various embodiments, the balloon is removed if the subject is not able to expel the balloon in 3 minutes.

For measurements using anorectal manometry, after 2 sodium phosphate enemas, anal pressures are assessed by a high resolution manometry catheter which comprises 10 circumferential sensors, 8 sensors at 6 mm intervals along the anal canal and 2 sensors in the rectal balloon. At each level, 36 circumferentially oriented pressure-sensing elements detect pressure over a length of 2.5 mm. Data are acquired at 35 Hz. The 36 sector pressures are then averaged to obtain a mean pressure measurement at each level. The response characteristics of each sensing element are such that they can record pressure transients in excess of 6,000 mm Hg/s and are accurate to within 1 mm Hg of atmospheric pressure for measurements obtained for at least the final 5 min of the study, immediately before thermal recalibration. During each study, parameters are assessed in the following chronological order: anorectal pressures at rest for a duration of 20 sec, during squeeze—3 attempts for a maximum duration of 20 sec each, and simulated evacuation before and after (50 ml) distending a rectal balloon.

Thereafter, the recto-anal inhibitory reflex and rectal sensation are simultaneously evaluated by progressively distending the rectal balloon in 20 ml increments from 0 to 200 ml and thereafter in 40 ml increments until a maximum volume of 400 ml is reached. Threshold volumes for first sensation, urgency, and maximum discomfort are recorded. These parameters are analyzed using commercially-available software. Rectal pressure is measured by the sensor in the rectal balloon. While anal pressures are recorded by several, generally 9, sensors, which straddle the anal canal, other options include reducing the data to a single value at every point in time. However, the calculations for deriving this single value vary among maneuvers. At rest, during squeeze, and rectal distention, such sensing identifies the highest of all pressures recorded by anal sensors at any point in time. This value is used to calculate the average anal resting and squeeze pressures over 20 seconds for each resting and all 3 squeeze maneuvers. The length of the high pressure zone (HPZ) is the length of the average pressure profile in the resting pressure frame defined as: {Rectal Pressure+([Anal Resting Pressure−Rectal Pressure]*0.25)}.

In contrast, during simulated evacuation, measuring a single value at every point in time identifies the most positive (or least negative) difference between rectal and anal (Rectal−Anal) pressure over a 20-second epoch. During rectal distention, anal relaxation percentage (%) is calculated as [(1−residual anal pressure/anal resting pressure)× 100]. The recto-anal inhibitory reflex is considered present if anal relaxation is greater than 25%.

Figure 24:
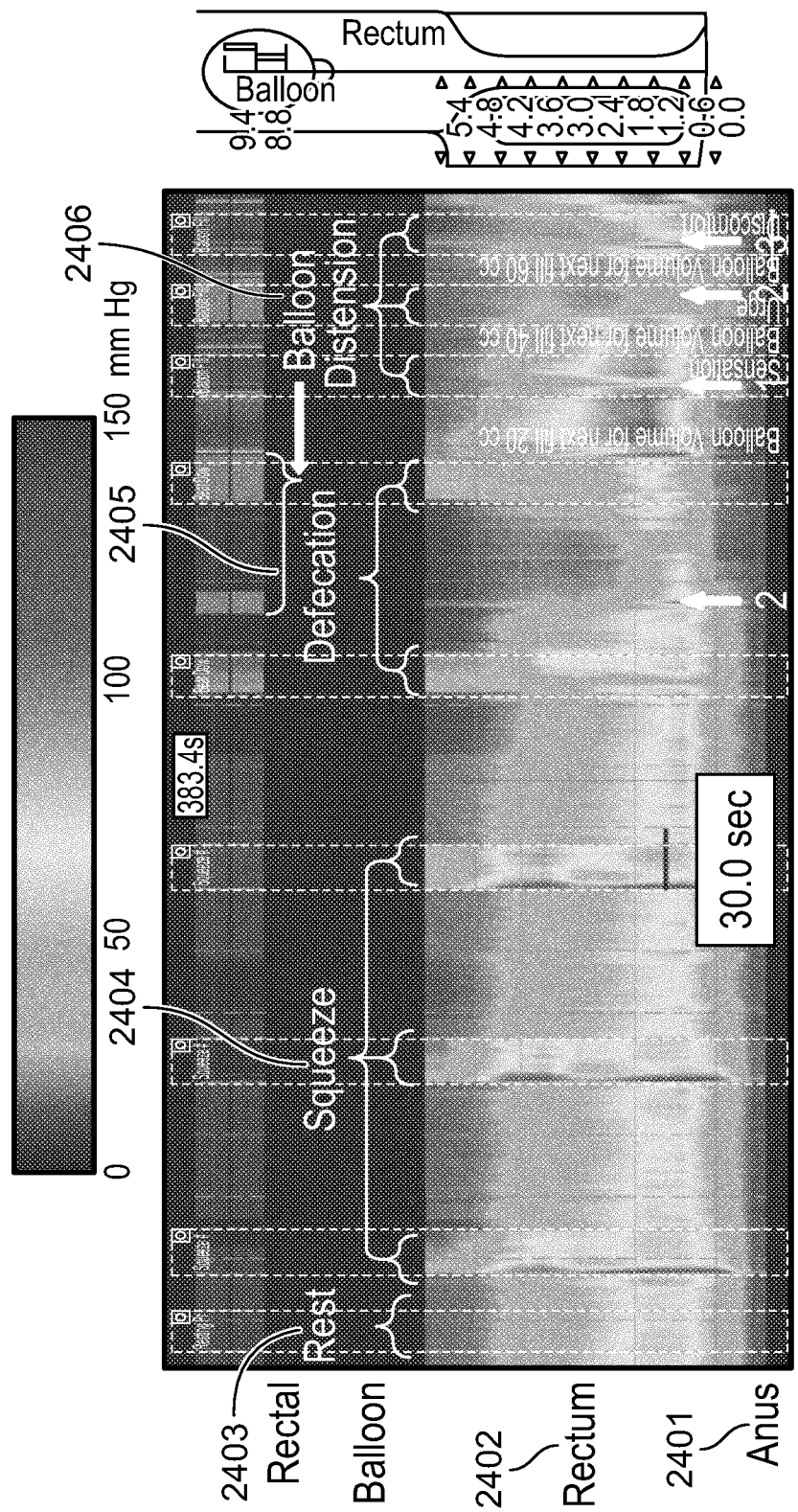
FIG. 24 is a representative image of high resolution anorectal manometry used for measuring fecal incontinence parameters.

FIG. 24 is a representative image of high resolution anorectal manometry. Referring to FIG. 24, the results of the procedure show the pressure measured in the anus 2401 and the rectum 2402 of a patient, during rest 2403, squeeze 2404, defecation 2405 and balloon distension 2406 phases of the procedure, as described above.

Referring back to FIG. 22, the various parameters measured by high resolution anorectal manometry are shown. In various embodiments, treatment of fecal incontinence in a patient using the systems and methods of the present specification results in an improvement of at least 5% compared to pretreatment values in the following parameters measured by anorectal manometry:

Internal Anal Sphincter resting pressure 2206—In various embodiments, this parameter shows an improvement of at least 5% or more than 33 mm Hg over pretreatment values. Internal Anal Sphincter pressure is defined as the difference between intra-rectal pressure and the highest recorded internal anal sphincter pressure at rest.

External Anal Sphincter resting pressure 2207—In various embodiments, this parameter shows an improvement of at least 5% over pretreatment values. External Anal Sphincter pressure is defined as the difference between intra-rectal pressure and the highest recorded external anal sphincter pressure at rest.

Anal Sphincter squeeze pressure 2208—In various embodiments, this parameter shows an improvement of at least 5% or more than 99 mm Hg over pretreatment values. Anal sphincter squeeze pressure is defined as the difference between the intra-rectal pressure and the highest pressure that is recorded at any level within the anal canal during a squeeze maneuver.

Stress testing (abdominal leak-point pressure) 2209—In various embodiments, this parameter shows an improvement of at least 5% or more than 60 cm $H_2O$ over pretreatment values.

Stress testing (abdominal leak-point volume) 2210—In various embodiments, this parameter shows an improvement of at least 5% or more than 50 cc over pretreatment values.

Anal high pressure zone 2211—In various embodiments, this parameter shows an improvement of at least 5% or more than 2.4 cm over pretreatment values.

Anal squeeze duration 2212—In various embodiments, this parameter shows an improvement of at least 5% or more than 3 seconds over pretreatment values.

First Sensation volume 2213—In various embodiments, this parameter shows an improvement of at least 5% or more than 20 ml over pretreatment values.

Desire to defecate volume 2214—In various embodiments, this parameter shows an improvement of at least 5% or more than 40 ml over pretreatment values.

Urgency Volume 2215—In various embodiments, this parameter shows an improvement of at least 5% or more than 60 ml over pretreatment values.

Balloon expulsion time 2216—In various embodiments, this parameter shows an improvement of at least 5% or less than 3 minutes over pretreatment values. A balloon expulsion test is used to assess recto-anal coordination during defecation. The test evaluates a patient's ability to expel a filled balloon from the rectum. Most normal subjects can expel the balloon within 1 minute.

Rectal pressure during evacuation 2217—In various embodiments, this parameter shows an improvement of at least 5% or more than 5 mm Hg over pretreatment values.

Anal pressure during evacuation 2218—In various embodiments, this parameter shows an improvement of at least 5% or less than 5 mm Hg over pretreatment values.

In various embodiments, treatment of fecal incontinence in a patient using the systems and methods of the present specification results in an increase in quality of life (SF6, SF12, Roger Goldberg scales) 2219 by at least 5% compared to pretreatment values. Health-related quality of life (HRQOL) is a composite health care outcome implying several subsets of function, often categorized into physical well-being, social function, mental health, societal role, and general health perception. HRQOL instruments are typically comprised of numerous patient completed questions, or items, arranged into several domains. SF-36 is the most common general HRQOL instrument, a self-administered tool organizing HRQOL into eight scales addressing physical function, social function, pain, emotional well-being, energy, general health perceptions, and role limitation due to physical and/or emotional problems.

The above examples are merely illustrative of the many applications of the system of the present invention. Although only a few embodiments of the present invention have been described herein, it should be understood that the present invention might be embodied in many other specific forms without departing from the spirit or scope of the invention. Specifically, the above invention can be embodied using a standard implantable pulse generator implanted surgically into a patient's body and the electrodes implanted proximate to the target tissue using standard lead implantation techniques. Therefore, the present examples and embodiments are to be considered as illustrative and not restrictive, and the invention may be modified within the scope of the appended claims.

We claim:

1. A method for improving a function of a urinary sphincter of a patient using a stimulation device, wherein the stimulation device comprises at least one electrode operably connected to a stimulus generator and a controller configured to transmit at least one stimulation signal to the stimulus generator, the method comprising:

implanting the device in an anorectal region of the patient;

positioning the electrode in electrical communication with a target tissue within said anorectal region of the patient, wherein the target tissue comprises at least one of a longitudinal muscle of a rectum, a circular muscle of the rectum, a muscularis mucosa of the rectum, a submucosa of the rectum, a pudendal nerve or a branch of the pudendal nerve, a conjoined longitudinal muscle, a superficial or deep part of an external anal sphincter, an internal anal sphincter, a muscularis mucosa of an anal canal, a subserosal plexus, a longitudinal intramuscular plexus, a circular intramuscular plexus, a periglandular plexus, a myenteric (Auerbach's) plexus, a submucosal (Meissner's) plexus of an anorectum, or perineal tissue;

generating a stimulation signal using said controller based on a plurality of programmatic instructions stored within said controller; and generating an electrical stimulation pulse, in response to said stimulation signal, using the stimulus generator, wherein said electrical stimulation pulse is transmitted to said target tissue within said anorectal region via said at least one electrode and wherein the electrical stimulation pulse comprises a pulse width having a range of 10 μsec to 500 msec, a pulse amplitude of 1 μAmp to 100 mAmp, and a pulse frequency of 0.02 Hz to 100 Hz; and modulating at least one of the pulse width, the pulse amplitude or pulse frequency in order improve the function of the urinary sphincter of the patient for at least 24 hours after stimulation ceases.

2. The method for improving a function of a urinary sphincter of a patient of claim 1, wherein said device further comprises at least one sensor configured to obtain data and said method further comprises modifying said electrical stimulation pulse based on the data from the at least one sensor.

3. The method for improving a function of a urinary sphincter of a patient of claim 2, wherein said at least one sensor comprises a pressure sensor, an electrical activity sensor, an impedance sensor, an accelerometer, or an inclinometer.

4. The method for improving a function of a urinary sphincter of a patient of claim 1, wherein, after an application of said electrical stimulation pulse, an abdominal leak point pressure increases by at least five percent or at least 60 cm $H_2O$ relative to an abdominal leak point pressure prior to said application of said electrical stimulation pulse.

5. The method for improving a function of a urinary sphincter of a patient of claim 1, wherein, after an application of said electrical stimulation pulse, an abdominal leak point volume increases by at least five percent or at least 50 cc relative to an abdominal leak point volume prior to said application of said electrical stimulation pulse.

6. The method for improving a function of a urinary sphincter of a patient of claim 1, wherein, after an application of said electrical stimulation pulse, a post void residual urine volume determination increases by at least five percent relative to a post void residual urine volume determination prior to said application of said electrical stimulation pulse.

7. The method for improving a function of a urinary sphincter of a patient of claim 1, wherein, after an application of said electrical stimulation pulse, uroflowmetry increases by at least five percent relative to uroflowmetry prior to said application of said electrical stimulation pulse.

8. The method for improving a function of a urinary sphincter of a patient of claim 1, wherein, after an application of said electrical stimulation pulse, a bladder compliance increases by at least five percent or at least 20 ml/cm $H_2O$ relative to a bladder compliance prior to said application of said electrical stimulation pulse.

9. The method for improving a function of a urinary sphincter of a patient of claim 1, wherein, after an application of said electrical stimulation pulse, a detrusor leak point pressure increases by at least five percent or at least 40 cm $H_2O$ relative to a detrusor leak point pressure prior to said application of said electrical stimulation pulse.

10. The method for improving a function of a urinary sphincter of a patient of claim 1, wherein, after an application of said electrical stimulation pulse, a first sensation volume increases by at least 5% or at least 50 ml relative to a first sensation volume prior to said application of said electrical stimulation pulse.

11. The method for improving a function of a urinary sphincter of a patient of claim 1, wherein, after an application of said electrical stimulation pulse, a second sensation (full) volume increases by at least 5% or at least 200 ml relative to a second sensation (full) volume prior to said application of said electrical stimulation pulse.

12. The method for improving a function of a urinary sphincter of a patient of claim 1, wherein, after an application of said electrical stimulation pulse, a bladder maximum capacity increases by at least 5% or at least 400 ml relative to a bladder maximum capacity prior to said application of said electrical stimulation pulse.

13. The method for improving a function of a urinary sphincter of a patient of claim 1, wherein, after an application of said electrical stimulation pulse, a maximum detrusor pressure increase by at least 5% or at least 20 cm $H_2O$ relative to a maximum detrusor pressure prior to said application of said electrical stimulation pulse.

14. The method for improving a function of a urinary sphincter of a patient of claim 1, wherein, after an application of said electrical stimulation pulse, a detrusor contractility increases by at least 5% but no greater than 25% relative to a detrusor contractility prior to said application of said electrical stimulation pulse.

15. The method for improving a function of a urinary sphincter of a patient of claim 1, wherein, after an application of said electrical stimulation pulse, a number of incontinence episodes or a mean incontinence volume per incontinence episode is decreased by at least 5% relative to a number of incontinence episodes or a mean incontinence volume per incontinence episode prior to said application of said electrical stimulation pulse.

16. The method for improving a function of a urinary sphincter of a patient of claim 1, wherein, after an application of said electrical stimulation pulse, a total voided volume increases by at least 5% relative to a total voided volume prior to said application of said electrical stimulation pulse.

17. The method for improving a function of a urinary sphincter of a patient of claim 1, wherein, after an application of said electrical stimulation pulse, patient incontinence perception scores on a visual analog scale improve by at least 5% relative to patient incontinence perception scores on a visual analog scale prior to said application of said electrical stimulation pulse.

18. The method for improving a function of a urinary sphincter of a patient of claim 1, wherein, after an application of said electrical stimulation pulse, a Stamey's incontinence score improves by at least 1 grade relative to a Stamey's incontinence score prior to said application of said electrical stimulation pulse.

* * * * *